(12) United States Patent
Kilburn et al.

(10) Patent No.: US 8,053,431 B2
(45) Date of Patent: Nov. 8, 2011

(54) PHARMACEUTICAL USE OF SUBSTITUTED AMIDES

(75) Inventors: John Paul Kilburn, Haslev (DK); Henrik Sune Andersen, Lyngby (DK); Gita Camilla Tejlgaard Kampen, Nærun (DK); Soren Ebdrup, Roskilde (DK)

(73) Assignee: High Point Pharmaceuticals, LLC, High Point, NC (US)

( * ) Notice: Subject to any disclaimer, the term of this patent is extended or adjusted under 35 U.S.C. 154(b) by 351 days.

(21) Appl. No.: 12/092,223

(22) PCT Filed: Nov. 1, 2006

(86) PCT No.: PCT/EP2006/068017
§ 371 (c)(1), (2), (4) Date: Oct. 23, 2008

(87) PCT Pub. No.: WO2007/051811
PCT Pub. Date: May 10, 2007

(65) Prior Publication Data
US 2009/0118259 A1 May 7, 2009

(30) Foreign Application Priority Data
Nov. 1, 2005 (EP) .................................. 05110226

(51) Int. Cl.
*C07D 231/54* (2006.01)
*A61K 31/4184* (2006.01)
*A61P 9/12* (2006.01)
*A61P 3/10* (2006.01)
*A61P 25/28* (2006.01)
*A61P 3/04* (2006.01)

(52) U.S. Cl. .................. 514/228.2; 514/234.2; 514/394; 514/322; 514/381; 548/453; 548/250; 546/199; 544/58.5; 544/116

(58) Field of Classification Search .................. None
See application file for complete search history.

(56) References Cited

U.S. PATENT DOCUMENTS

| | | |
|---|---|---|
| 2,913,454 A | 1/1959 | Petersen et al. |
| 3,723,442 A | 3/1973 | Nakanishi et al. |
| 3,784,551 A | 1/1974 | Nakanishi et al. |
| 4,350,696 A | 9/1982 | Cross et al. |
| 4,482,555 A | 11/1984 | Doria et al. |
| 4,851,423 A | 7/1989 | Girijavallabhan et al. |
| 4,963,590 A | 10/1990 | Backstrom et al. |
| 5,001,133 A | 3/1991 | Richardson et al. |
| 5,049,695 A | 9/1991 | Abraham et al. |
| 5,112,861 A | 5/1992 | Backstrom et al. |
| 5,122,539 A | 6/1992 | Abraham et al. |
| 5,169,850 A | 12/1992 | Dusza et al. |
| 5,225,402 A | 7/1993 | Ogawa et al. |
| 5,258,407 A | 11/1993 | Washburn et al. |
| 5,260,325 A | 11/1993 | Markwalder et al. |
| 5,272,167 A | 12/1993 | Girijavallabhan et al. |
| 5,274,104 A | 12/1993 | Arnaud et al. |
| 5,290,803 A | 3/1994 | Abraham et al. |
| 5,314,880 A | 5/1994 | Whittaker et al. |
| 5,356,904 A | 10/1994 | Freidinger et al. |
| 5,382,680 A | 1/1995 | Abraham et al. |
| 5,426,105 A | 6/1995 | Manning et al. |
| 5,432,191 A | 7/1995 | Abraham et al. |
| 5,436,254 A | 7/1995 | Ogawa et al. |
| 5,446,194 A | 8/1995 | Backstrom et al. |
| 5,459,144 A | 10/1995 | Girijavallabhan et al. |
| 5,585,394 A | 12/1996 | Di Malta et al. |
| 5,591,892 A | 1/1997 | Abraham et al. |
| 5,596,020 A | 1/1997 | Morris et al. |
| 5,602,137 A | 2/1997 | Ruhter et al. |
| 5,648,375 A | 7/1997 | Abraham et al. |
| 5,650,513 A | 7/1997 | Langhals et al. |
| 5,652,247 A | 7/1997 | Ogawa et al. |
| 5,674,879 A | 10/1997 | Manning et al. |
| 5,677,330 A | 10/1997 | Abraham et al. |
| 5,705,521 A | 1/1998 | Abraham et al. |
| 5,731,454 A | 3/1998 | Abraham et al. |
| 5,750,532 A | 5/1998 | Girijavallabhan et al. |
| 5,786,379 A | 7/1998 | Bernardon |
| 5,795,907 A | 8/1998 | Kalindjian et al. |
| 5,872,282 A | 2/1999 | Abraham et al. |

(Continued)

FOREIGN PATENT DOCUMENTS

| | | |
|---|---|---|
| CN | 1736485 | 2/2006 |
| DE | 4338784 | 5/1995 |
| FR | 2456731 | 12/1980 |
| GB | 825514 | 11/1956 |
| JP | 08-048662 | 2/1996 |
| JP | 09-221476 | 8/1997 |
| JP | 11-152269 | 6/1999 |
| JP | 2001 139574 | 5/2001 |
| JP | 2003-286171 | 10/2003 |
| JP | 2007-231005 | 9/2007 |

(Continued)

OTHER PUBLICATIONS

Fotsch C. et al., "11 [beta]-Hydroxysteroid dehydrogenase-1 as a therapeutic target for metabolic diseases" Expert Opinion on Therapeutic Patents, Ashley Publications, GB, vol. 15, No. 3, 2005, pp. 289-303.

(Continued)

*Primary Examiner* — Susanna Moore
(74) *Attorney, Agent, or Firm* — Robert S. Dailey

(57) ABSTRACT

The use of substituted amides for modulating the activity of 11-hydroxysteroid dehydrogenase type 1 (11HSD1) and the use of these compounds as pharmaceutical compositions, are described. Also a novel class of substituted amides, their use in therapy, pharmaceutical compositions comprising the compounds, as well as their use in the manufacture of medicaments are described. The present compounds are modulators and more specifically inhibitors of the activity of 11HSD1 and may be useful in the treatment, prevention and/or prophylaxis of a range of medical disorders where a decreased intracellular concentration of active glucocorticoid is desirable.

8 Claims, No Drawings

U.S. PATENT DOCUMENTS

| | | |
|---|---|---|
| 5,912,260 A | 6/1999 | Kalindjian et al. |
| 5,919,829 A | 7/1999 | Kalindjian et al. |
| 5,927,283 A | 7/1999 | Abraham et al. |
| 5,932,569 A | 8/1999 | Janssens et al. |
| 5,939,437 A | 8/1999 | Kalindjian et al. |
| 6,001,879 A | 12/1999 | Seitz et al. |
| 6,096,736 A | 8/2000 | Ogawa et al. |
| 6,124,289 A | 9/2000 | He et al. |
| 6,458,803 B1 | 10/2002 | Sikorski et al. |
| 6,506,783 B1 * | 1/2003 | Camden .................. 514/388 |
| 6,521,641 B1 | 2/2003 | Klein et al. |
| 6,548,549 B1 | 4/2003 | Seitz et al. |
| 6,613,803 B1 | 9/2003 | Wang et al. |
| 6,638,947 B2 | 10/2003 | Wang et al. |
| 6,696,442 B2 | 2/2004 | Wang et al. |
| 6,833,371 B2 | 12/2004 | Atkinson et al. |
| 7,129,242 B2 | 10/2006 | Satoh et al. |
| 7,157,490 B2 | 1/2007 | Colandrea et al. |
| 7,186,735 B2 | 3/2007 | Strobel et al. |
| 7,265,122 B2 | 9/2007 | Wu et al. |
| 7,358,238 B2 | 4/2008 | Andersen et al. |
| 7,501,405 B2 | 3/2009 | Kampen et al. |
| 7,557,110 B2 | 7/2009 | Kataoka et al. |
| 7,700,583 B2 | 4/2010 | Gundertofte et al. |
| 7,723,323 B2 | 5/2010 | Andersen et al. |
| 2002/0006932 A1 | 1/2002 | Galley et al. |
| 2002/0115671 A1 | 8/2002 | Goehring |
| 2003/0144256 A1 | 7/2003 | Klein et al. |
| 2004/0142922 A1 | 7/2004 | Alanine et al. |
| 2004/0186102 A1 | 9/2004 | Wu et al. |
| 2005/0009871 A1 | 1/2005 | Ramesh et al. |
| 2005/0054850 A1 | 3/2005 | Wu et al. |
| 2005/0080087 A1 | 4/2005 | Pendri et al. |
| 2005/0154202 A1 | 7/2005 | Hagmann et al. |
| 2005/0261302 A1 | 11/2005 | Hoff et al. |
| 2006/0009918 A1 | 1/2006 | Mallik et al. |
| 2006/0079506 A1 | 4/2006 | Linders et al. |
| 2006/0094699 A1 | 5/2006 | Kampen et al. |
| 2006/0111366 A1 | 5/2006 | Andersen et al. |
| 2006/0149070 A1 | 7/2006 | Rohde et al. |
| 2006/0281773 A1 | 12/2006 | Patel et al. |
| 2007/0054882 A1 | 3/2007 | Klein et al. |
| 2007/0270408 A1 | 11/2007 | Andersen et al. |
| 2008/0108598 A1 | 5/2008 | Andersen et al. |
| 2009/0105289 A1 | 4/2009 | Kilburn et al. |
| 2009/0124598 A1 | 5/2009 | Andersen et al. |
| 2009/0137574 A1 | 5/2009 | Kampen et al. |
| 2009/0264412 A1 | 10/2009 | Kampen et al. |
| 2009/0264414 A1 | 10/2009 | Andersen et al. |
| 2009/0306048 A1 | 12/2009 | Kilburn et al. |
| 2009/0325932 A1 | 12/2009 | Ebdrup et al. |
| 2010/0056600 A1 | 3/2010 | Ebdrup et al. |
| 2010/0076041 A1 | 3/2010 | Kilburn et al. |
| 2010/0087543 A1 | 4/2010 | Ebdrup et al. |
| 2010/0120743 A1 | 5/2010 | Gundertofte et al. |
| 2010/0137377 A1 | 6/2010 | Petersen et al. |
| 2010/0168083 A1 | 7/2010 | Ebdrup |
| 2010/0197658 A1 | 8/2010 | Andersen et al. |
| 2010/0292215 A1 | 11/2010 | Ebdrup et al. |
| 2010/0331366 A1 | 12/2010 | Ebdrup |
| 2011/0003852 A1 | 1/2011 | Ebdrup |
| 2011/0003856 A1 | 1/2011 | Ebdrup |
| 2011/0039853 A1 | 2/2011 | Ebdrup |

FOREIGN PATENT DOCUMENTS

| | | |
|---|---|---|
| WO | WO 94/01113 | 1/1994 |
| WO | WO 94/18193 | 8/1994 |
| WO | WO 97/07789 | 3/1997 |
| WO | WO 97/22588 | 6/1997 |
| WO | WO 97/24328 | 7/1997 |
| WO | WO 98/46559 | 10/1998 |
| WO | WO 99/30699 | 6/1999 |
| WO | WO 99/61013 | 12/1999 |
| WO | WO 00/12074 | 3/2000 |
| WO | WO 00/46197 | 8/2000 |
| WO | WO 00/47558 | 8/2000 |
| WO | WO 00/63165 | 10/2000 |
| WO | WO 00/73283 | 12/2000 |
| WO | WO 01/02385 | 1/2001 |
| WO | WO 01/22969 | 4/2001 |
| WO | WO 01/32621 | 5/2001 |
| WO | WO 01/44213 | 6/2001 |
| WO | WO 01/64676 | 9/2001 |
| WO | WO 01/90090 | 11/2001 |
| WO | WO 01/90091 | 11/2001 |
| WO | WO 01/90092 | 11/2001 |
| WO | WO 01/90093 | 11/2001 |
| WO | WO 01/90094 | 11/2001 |
| WO | WO 02/00626 | 1/2002 |
| WO | WO 02/02797 | 1/2002 |
| WO | WO 02/10191 | 2/2002 |
| WO | WO 02/072084 | 9/2002 |
| WO | WO 02/076435 | 10/2002 |
| WO | WO 02/089781 | 11/2002 |
| WO | WO 02/094799 | 11/2002 |
| WO | WO 02/100819 | 12/2002 |
| WO | WO 03/000649 | 1/2003 |
| WO | WO 03/028641 | 4/2003 |
| WO | WO 03/028730 | 4/2003 |
| WO | WO 03/029245 | 5/2003 |
| WO | WO 03/037274 | 5/2003 |
| WO | WO 03/037900 | 5/2003 |
| WO | WO 03/065983 | 8/2003 |
| WO | WO 03/070732 | 8/2003 |
| WO | WO 03/086410 | 10/2003 |
| WO | WO 2004/024896 | 3/2004 |
| WO | WO 2004/024897 | 3/2004 |
| WO | WO 2004/033427 | 4/2004 |
| WO | WO 2004/052461 | 6/2004 |
| WO | WO 2004/056744 | 7/2004 |
| WO | WO 2004/056745 | 7/2004 |
| WO | WO 2004/065351 | 8/2004 |
| WO | WO 2004/075823 | 9/2004 |
| WO | WO 2004/087159 | 10/2004 |
| WO | WO 2004/089380 | 10/2004 |
| WO | WO 2004/089415 | 10/2004 |
| WO | WO 2004/089416 | 10/2004 |
| WO | WO 2004/089470 | 10/2004 |
| WO | WO 2004/089471 | 10/2004 |
| WO | WO 2004/089896 | 10/2004 |
| WO | WO 2004/091610 | 10/2004 |
| WO | WO 2005/013950 | 2/2005 |
| WO | WO 2005/028438 | 3/2005 |
| WO | WO 2005/032484 | 4/2005 |
| WO | WO 2005/035534 | 4/2005 |
| WO | WO 2005/085202 | 9/2005 |
| WO | WO 2005/095397 | 10/2005 |
| WO | WO 2005/115975 | 12/2005 |
| WO | WO 2006/009835 | 1/2006 |
| WO | WO 2006/014012 | 2/2006 |
| WO | WO 2006/028958 | 3/2006 |
| WO | WO 2006/040329 | 4/2006 |
| WO | WO 2006/044645 | 4/2006 |
| WO | WO 2006/048330 | 5/2006 |
| WO | WO 2006/055752 | 5/2006 |
| WO | WO 2006/094633 | 9/2006 |
| WO | WO 2006/105127 | 10/2006 |
| WO | WO 2006/113261 | 10/2006 |
| WO | WO 2006/136402 | 12/2006 |
| WO | WO 2007/046001 | 4/2007 |
| WO | WO 2007/051810 | 5/2007 |
| WO | WO 2007/058960 | 5/2007 |
| WO | WO 2007/059905 | 5/2007 |
| WO | WO 2007/066784 | 6/2007 |
| WO | WO 2007/107550 | 9/2007 |
| WO | WO 2007/109160 | 9/2007 |
| WO | WO 2007/115935 | 10/2007 |
| WO | WO 2007/144394 | 12/2007 |
| WO | WO 2008/002244 | 1/2008 |
| WO | WO 2008/006702 | 1/2008 |
| WO | WO 2008/006703 | 1/2008 |
| WO | WO 2008/101885 | 8/2008 |
| WO | WO 2008/101886 | 8/2008 |
| WO | WO 2008/101907 | 8/2008 |
| WO | WO 2008/101914 | 8/2008 |
| WO | WO 2008/110196 | 9/2008 |

| | | |
|---|---|---|
| WO | WO 2008/119017 | 10/2008 |
| WO | WO 2008/127924 | 10/2008 |
| WO | WO 2008/134221 | 11/2008 |
| WO | WO 2009/126863 | 10/2009 |
| WO | WO 2010/057126 | 5/2010 |
| WO | WO 2010/059618 | 5/2010 |

OTHER PUBLICATIONS

PCT International Search Report for Application No. PCT/EP2006/068017 dated Nov. 30, 2007.
Andrew et al., J. Clin. Endocrinol. Metab. vol. 87, pp. 277-285 (2002).
Andrews et al., J. Clin. Endocrinol. Metab. vol. 88, pp. 285-291 (2003).
Barf T et al: "Recent progress in 11-[beta]-hydroxysteroid dehydrogenase type 1 (11-[beta]-HSD1) inhibitor development" Drugs of the Future 2006 Spain, vol. 31, No. 3, Mar. 2006, pp. 231-243.
Bird et al., J. Physiology vol. 585, pp. 187-201 (2007).
Brem et al., Hypertension vol. 31, pp. 459-462 (1998).
Brindley et al., Progress Lipid Res. vol. 30, pp. 349-360 (1991).
Bujalska et al., Endocrinology vol. 140, pp. 3188-3196 (1999).
Carruthers et al., J. Chem. Soc. Perkin Trans. 1 vol. 10, pp. 2854-2856 (1990).
Cooper et al., Bone vol. 27, pp. 375-381 (2000).
Coppola et al., J. Med. Chem. vol. 48, pp. 6696-6712 (2005).
Davani et al., J. Biol. Chem. vol. 275, pp. 34841-34844 (2000).
Demchenko, Chem. Hetero. Comp. vol. 36, pp. 985-988 (2000).
Desai et al., Tetrahedron Lett. vol. 34, pp. 7685-7688 (1993).
Donohue et al., J. Comb. Chem. vol. 4, pp. 23-32 (2002).
Evans et al., J. Med. Chem. vol. 35, pp. 3919-3927 (1992).
Ganguly A.K. et al.; "Sythesis of heterocyclic compounds using radical reactions" Tetrahedron Letters, Elsevier, Amsterdam, NL, vol. 43, No. 38, Sep. 16, 2002, pp. 6865-6868.
Giacomelli et al. Eur. J. Org. Chem. vol. 3, pp. 537-541 (2003).
Hashigaki et al., Chem. Pharm. Bull. vol. 32, pp. 3561-3568 (1984).
Hosfield et al., J Biol. Chem. vol. 280, pp. 4639-4648 (2005).
Ignatova Irena D. et al.: "Tumor necrosis factor-alpha upregultes 11 beta-hydroxysteroid dehydrogenase type 1 expression by CCAAT/enhancer binding protein-beta in HepG2 cells" American Journal of Physiology—endocrinology and Metabolism, vol. 296, No. 2, Feb. 2009, pp. F367-F377.
International Preliminary Report on Patentability for PCT International Patent Application No. PCT/EP2006/068017, dated May 15, 2008.
Johnson et al., J. Org. Chem. vol. 35, pp. 622-626 (1970).
Kondo et al., "Characterization of Orally Active Nonpeptide Vasopressin V2 Receptor Agonist" Journal of Medicinal Chemistry, vol. 45, No. 17, 2002, pp. 3805-3808.
Kondo et al: "Novel Design of Nonpeptide AVP V2 Receptor Agonists: Structural Requirements for and Agonist Having 1-(4-Aminobenzoyl)-2,3,4,5,-tetrahydro-1H-1-benezazepine as a Template" Journal of Medicinal Chemistry, vol. 43, No. 23, 2000, pp. 4388-4397.
Koteletsev et al., Proc. Nat'l Acad. Sci. vol. 94, pp. 14924-14929 (1997).
Leyendecker et al., Nouveau J. de Chimie vol. 9, pp. 13-19 (1985).
Mariani et al., Farmaco vol. 38, pp. 653-663 (1983).
Massa et al., J. Heterocycl. Chem. vol. 27, pp. 1805-1808 (1990).
Masuzaki et al., J. Clin. Invest. vol. 112, pp. 83-90 (2003).
Masuzaki et al., Science vol. 294, pp. 2166-2170 (2001).

McCullough et al., J. Chem. Soc. Perkin Trans. 1 vol. 20, pp. 2553-2560 (1996).
Moisan et al., Endocrinology, vol. 127, pp. 1450-1455 (1990).
Morton et al., J. Biol. Chem. vol. 276, pp. 41293-41300 (2001).
Nankervis et al.: "Calcium sensitizazion as a positive inotropic mechanism. . ." Journal of Cardiovascular Pharmacology, vol. 24, No. 4, 1994, pp. 612-617.
Nieczypor et al., Eu. J. Org. Chem. vol. 2004, pp. 812-819 (2004).
Pending Claims for U.S. Appl. No. 11/665,103, filed Mar. 24, 2011.
Pending Claims for U.S. Appl. No. 12/092,230, filed Mar. 25, 2011.
Pending Claims for U.S. Appl. No. 12/293,709, filed Mar. 25, 2011.
Pending Claims for U.S. Appl. No. 12/304,501, filed Mar. 25, 2011.
Pending Claims for U.S. Appl. No. 12/307,999, filed May 23, 2011.
Pending Claims for U.S. Appl. No. 12/308,000, filed Mar. 28, 2011.
Pending Claims for U.S. Appl. No. 12/528,227, filed Mar. 28, 2011.
Pending Claims for U.S. Appl. No. 12/528,229, filed Mar. 29, 2011.
Pending Claims for U.S. Appl. No. 12/528,231, filed Mar. 28, 2011.
Pending Claims for U.S. Appl. No. 12/528,233, filed Mar. 29, 2011.
Pending Claims for U.S. Appl. No. 12/529,956, filed Mar. 29, 2011.
Pending Claims for U.S. Appl. No. 12/593,456, filed Mar. 29, 2011.
Pending Claims for U.S. Appl. No. 12/595,310, filed Mar. 29, 2011.
Pending Claims for U.S. Appl. No. 12/597,129, filed Mar. 29, 2011.
Pending Claims for U.S. Appl. No. 13/078,221, filed Apr. 1, 2011.
Pending Claims for U.S. Appl. No. 13/128,045, filed May 6, 2011.
Rauz et al., Invest. Opthalmol. Vis. Sci. vol. 42, pp. 2037-2042 (2001).
Reed et al., Scand. J. Gastroentreol. vol. 15, pp. 51-56 (1980).
Schwartz et al., Nature vol. 404, pp. 661-671 (2000).
Seefelter et al., Chemische Berichte vol. 96, pp. 3243-3253 (1963).
Skowronska-Ptasinska et al: "Effect of Different Dialkylamino Groups on the Regioselectivity of Lithiation of 0-Protected 3-(Dialkylamino)phenols" Journal of Organic Chemistry, vol. 50, No. 15, 1985, pp. 2690-2698.
Sohar R et al: "Conformational Analysis of N-Acylazabycyclooctanes," Magnetic Resonance in Chemistry, John Wiley, Chichester, GB, vol. 23, No. 7, Jan. 1, 1985, pp. 506-513.
Souness et al., Steroids vol. 67, pp. 195-201 (2002).
Tabuchi, S. et al.: "Novel Potent Antagonists of Human Neuropeptide Y Y5 Receptor. Part 1: 2-Oxobenzothiazolin-3-acetic Acid Derivatives" Bioorganic & Medicinal Chemistry Letters, vol. 12, 2002, pp. 1171-1175.
Tannin et al., J. Biol. Chem. vol. 266, pp. 16653-16658 (1991).
Tomlinson et al., J. Clin. Endocrinol. Metab. vol. 87, pp. 57-62 (2002).
Villani, F.J. et al.; "Derivatives of 2-Azabicyclo[2.2.2]octane" Journal of Medicinal Chemistry, 1966, pp. 264-265.
Walker et al., J. Clin. Endocrinol. Metab. vol. 80, pp. 3155-3159 (1995).
Whitworth et al., J. Hypertens. vol. 20, pp. 1035-1043 (2002).
Whorwood et al., J. Clin. Endocrinol. Metab. vol. 86, pp. 2296-2308 (2001).
Willoughby C A et al: "Solid Phase Synthesis of Aryl Amines" Tetrahedron Letters, Elsevier, Amsterdam, NL, vol. 37, No. 40, Sep. 30, 1996, pp. 7181-7184 XP004030858 ISSN: 0040-4039 table 2; compound 1.
Wu et al., Toxicology vol. 236, pp. 1-6 (2007).
Yang et al., Bioorg. Med. Chem. Lett. vol. 8, pp. 107-112 (1998).
Yau et al., Proc. Nat'l Acad. Sci. vol. 98, pp. 4716-4721 (2001).
Yudt et al., Mol. Endocrinol. vol. 16, pp. 1719-1726 (2002).

* cited by examiner

PHARMACEUTICAL USE OF SUBSTITUTED AMIDES

CROSS-REFERENCE TO RELATED APPLICATIONS

This application is the United States national stage application, pursuant to 35 U.S.C. 371, of PCT/EP2006/068017, filed Nov. 1, 2006 which claims benefit of European Patent Application No. 05110226.7, filed Nov. 1, 2005.

FIELD OF INVENTION

The present invention relates to use of substituted amides and pharmaceutical compositions comprising the same for treating disorders where it is desirable to modulate the activity of 11β-hydroxysteroid dehydrogenase type 1 (11βHSD1). The present invention also relates to novel substituted amides, to their use in therapy, to pharmaceutical compositions comprising the same, to the use of said compounds in the manufacture of medicaments, and to therapeutic methods comprising the administration of the compounds. The present compounds modulate the activity of 11β-hydroxysteroid dehydrogenase type 1 (11βHSD1) and are accordingly useful in the treatment of diseases in which such a modulation is beneficial, such as the metabolic syndrome.

BACKGROUND OF THE INVENTION

The metabolic syndrome is a major global health problem. In the US, the prevalence in the adult population is currently estimated to be approximately 25%, and it continues to increase both in the US and worldwide. The metabolic syndrome is characterised by a combination of insulin resistance, dyslipidemia, obesity and hypertension leading to increased morbidity and mortality of cardiovascular diseases. People with the metabolic syndrome are at increased risk of developing frank type 2 diabetes, the prevalence of which is equally escalating.

In type 2 diabetes, obesity and dyslipidemia are also highly prevalent and around 70% of people with type 2 diabetes additionally have hypertension once again leading to increased mortality of cardiovascular diseases.

In the clinical setting, it has long been known that glucocorticoids are able to induce all of the cardinal features of the metabolic syndrome and type 2 diabetes.

11β-hydroxysteroid dehydrogenase type 1 (11βHSD1) catalyses the local generation of active glucocorticoid in several tissues and organs including predominantly the liver and adipose tissue, but also e.g. skeletal muscle, bone, pancreas, endothelium, ocular tissue and certain parts of the central nervous system. Thus, 11βHSD1 serves as a local regulator of glucocorticoid actions in the tissues and organs where it is expressed (Tannin et al., *J. Biol. Chem.*, 266, 16653 (1991); Bujalska et al., *Endocrinology*, 140, 3188 (1999); Whorwood et al., *J Clin Endocrinol Metab.*, 86, 2296 (2001); Cooper et al., *Bone*, 27, 375 (2000); Davani et al., *J. Biol. Chem.*, 275, 34841 (2000); Brem et al., *Hypertension*, 31, 459 (1998); Rauz et al., *Invest Opthalmol. Vis. Sci.*, 42, 2037 (2001); Moisan et al., *Endocrinology*, 127, 1450 (1990)).

The role of 11βHSD1 in the metabolic syndrome and type 2 diabetes is supported by several lines of evidence. In humans, treatment with the non-specific 11βHSD1 inhibitor carbenoxolone improves insulin sensitivity in lean healthy volunteers and people with type 2 diabetes. Likewise, 11βHSD1 knock-out mice are resistant to insulin resistance induced by obesity and stress. Additionally, the knock-out mice present with an anti-atherogenic lipid profile of decreased VLDL triglycerides and increased HDL-cholesterol. Conversely, mice that overexpress 11βHSD1 in adipocytes develop insulin resistance, hyperlipidemia and visceral obesity, a phenotype that resembles the human metabolic syndrome (Andrews et al., *J. Clin. Endocrinol. Metab.*, 88, 285 (2003); Walker et al., *J. Clin. Endocrinol. Metab.*, 80, 3155 (1995); Morton et al., *J. Biol. Chem.*, 276, 41293 (2001); Kotelevtsev et al., *Proc. Natl. Acad. Sci. USA*, 94, 14924 (1997); Masuzaki et al., *Science*, 294, 2166 (2001)).

The more mechanistic aspects of 11βHSD1 modulation and thereby modulation of intracellular levels of active glucocorticoid have been investigated in several rodent models and different cellular systems. 11βHSD1 promotes the features of the metabolic syndrome by increasing hepatic expression of the rate-limiting enzymes in gluconeogenesis, namely phosphoenolpyuvate carboxykinase and glucose-6-phosphatase, promoting the differentiation of preadipocytes into adipocytes thus facilitating obesity, directly and indirectly stimulating hepatic VLDL secretion, decreasing hepatic LDL uptake and increasing vessel contractility (Kotelevtsev et al., *Proc. Natl. Acad. Sci. USA*, 94, 14924 (1997); Morton et al., *J. Biol. Chem.* 276, 41293 (2001); Bujalska et al., *Endocrinology*, 140, 3188 (1999); Souness et al., *Steroids*, 67, 195 (2002), Brindley & Salter, *Prog. Lipid Res.*, 30, 349 (1991)).

WO 01/90090, WO 01/90091, WO 01/90092, WO 01/90093 and WO 01/90094 discloses various thiazol-sulfonamides as inhibitors of the human 11β-hydroxysteroid dehydrogenase type 1 enzyme, and further states that said compounds may be useful in treating diabetes, obesity, glaucoma, osteoporosis, cognitive disorders, immune disorders and depression.

We have now found substituted amides that modulate the activity of 11βHSD1 leading to altered intracellular concentrations of active glucocorticoid. More specifically, the present compounds inhibit the activity of 11βHSD1 leading to decreased intracellular concentrations of active glucocorticoid. Thus, the present compounds can be used to treat disorders where a decreased level of active intracellular glucocorticoid is desirable, such as e.g. the metabolic syndrome, type 2 diabetes, impaired glucose tolerance (IGT), impaired fasting glucose (IFG), dyslipidemia, obesity, hypertension, diabetic late complications, cardiovascular diseases, arteriosclerosis, atherosclerosis, myopathy, muscle wasting, osteoporosis, neurodegenerative and psychiatric disorders, and adverse effects of treatment or therapy with glucocorticoid receptor agonists.

One object of the present invention is to provide compounds, pharmaceutical compositions and use of compounds that modulate the activity of 11βHSD1.

DEFINITIONS

In the following structural formulas and throughout the present specification, the following terms have the indicated meaning. The examples provided in the definitions present in this application are non-inclusive unless otherwise stated. They include but are not limited to the recited examples.

The term "halo" includes fluorine, chlorine, bromine, and iodine.

The term "trihalomethyl" includes trifluoromethyl, trichloromethyl, tribromomethyl, and triiodomethyl.

The term "trihalomethoxy" includes trifluorometoxy, trichlorometoxy, tribromometoxy, and triiodometoxy.

The term "alkyl" includes $C_1$-$C_8$ straight chain saturated and methylene aliphatic hydrocarbon groups and $C_3$-$C_8$ branched saturated hydrocarbon groups having the specified number of carbon atoms. For example, this definition includes methyl (Me), ethyl (Et), propyl (Pr), butyl (Bu), pentyl, hexyl, isopropyl (i-Pr), isobutyl (i-Bu), tert-butyl (t-Bu), sec-butyl (s-Bu), isopentyl, and neopentyl.

The term "alkenyl" includes $C_2$-$C_6$ straight chain unsaturated aliphatic hydrocarbon groups and branched $C_3$-$C_6$ unsaturated aliphatic hydrocarbon groups having the specified number of carbon atoms. For example, this definition includes ethenyl, propenyl, butenyl, pentenyl, hexenyl, methylpropenyl, and methylbutenyl.

The term "alkynyl" includes $C_2$-$C_6$ straight chain unsaturated aliphatic hydrocarbon groups and $C_4$-$C_6$ branched unsaturated aliphatic hydrocarbon groups having the specified number of carbon atoms. For example, this definition includes ethynyl, propynyl, butynyl, pentynyl, hexynyl, and methylbutynyl.

The term "saturated or partially saturated monocyclic, bicyclic, or tricyclic ring system" represents but is not limited to aziridinyl, azepanyl, azocanyl, pyrrolinyl, pyrrolidinyl, 2-imidazolinyl, imidazolidinyl, 2-pyrazolinyl, morpholinyl, piperidinyl, thiomorpholinyl, piperazinyl, phthalimide, 1,2,3,4-tetrahydro-quinolinyl, 1,2,3,4-tetrahydro-isoquinolinyl, 1,2,3,4-tetrahydro-quinoxalinyl, indolinyl, 1,6-aza-bicyclo[3.2.1]octane, 2-aza-bicyclo[4.1.1]octane, 2-aza-bicyclo[3.2.1]octanyl, 7-aza-bicyclo[4.1.1]octanyl, 9-aza-bicyclo[3.3.2]decanyl, 4-aza-tricyclo[4.3.1.1$^{3,8}$]undecanyl, 9-aza-tricyclo[3.3.2.0$^{3,7}$]decanyl.

The term "saturated or partially saturated ring" represents cyclopropyl, cyclobutyl, cyclopentyl, cyclohexyl, cyclobutenyl, cyclopentenyl, cyclohexenyl, cycloheptenyl, cyclooctenyl, cyclononenyl, cyclodecenyl, tetrahydrofuranyl, and tetrahydropyranyl.

The term "saturated or partially saturated aromatic ring" represents cyclopentyl, cyclohexyl, cyclobutenyl, cyclopentenyl, cyclohexenyl, cycloheptenyl, cyclooctenyl, cyclononenyl, cyclodecenyl, tetrahydrofuranyl, tetrahydropyranyl, phenyl, pyridyl, and pyrimidinyl.

The term "cycloalkyl" represents a saturated, mono-, bi-, tri- or spirocarbocyclic group having the specified number of carbon atoms (e.g., cyclopropyl, cyclobutyl, cyclopentyl, cyclohexyl, cycloheptyl, cyclooctyl, cyclononyl, cyclodecyl, bicyclo[3.2.1]octyl, spiro[4.5]decyl, norpinyl, norbonyl, norcaryl, and adamantyl).

The term "cycloalkylalkyl" represents a cycloalkyl group as defined above attached through an alkyl group having the indicated number of carbon atoms or substituted alkyl group as defined above (e.g., cyclopropylmethyl, cyclobutylethyl, and adamantylmethyl).

The term "cycloalkenyl" represents a partially saturated, mono-, bi-, tri- or spirocarbocyclic group having the specified number of carbon atoms (e.g., cyclobutenyl, cyclopentenyl, cyclohexenyl, cycloheptenyl, cyclooctenyl, cyclononenyl, and cyclodecenyl).

The term "cycloalkylcarbonyl" represents a cycloalkyl group as defined above having the indicated number of carbon atoms attached through a carbonyl group (e.g., cyclopropylcarbonyl and cyclohexylcarbonyl).

The term "cycloalkylalkylcarbonyl" represents a cycloalkyl group as defined above attached through an alkyl group having the indicated number of carbon atoms or substituted alkyl group as defined above (e.g., cyclohexylmethylcarbonyl and cycloheptylethylcarbonyl).

The term "hetcycloalkyl" represents a saturated mono-, bi-, tri-, or spirocarbocyclic group having the specified number of atoms with 1-4 of the specified number being heteroatoms or groups selected from nitrogen, oxygen, sulphur, SO, and $SO_2$ (e.g., tetrahydrofuranyl, tetrahydropyranyl, tertahydrothiopyranyl, piperidine, and pyridazine).

The term "hetcycloalkylalkyl" represents a hetcycloalkyl group as defined above attached through an alkyl group having the indicated number of carbon atoms (e.g., tetrahydrofuranylmethyl, tetrahydropyranylethyl, and tertahydrothiopyranylmethyl).

The term "hetcycloalkylcarbonyl" represents a hetcycloalkyl group as defined above having the indicated number of carbon atoms attached through a carbonyl group (e.g., 1-piperidin-4-yl-carbonyl and 1-(1,2,3,4-tetrahydro-isoquinolin-6-yl)carbonyl).

The term "alkyloxy" represents an alkyl group having the indicated number of carbon atoms attached through an oxygen bridge (e.g., methoxy, ethoxy, propyloxy, allyloxy, and cyclohexyloxy).

The term "alkyloxyalkyl" represents an alkyloxy group as defined above attached through an alkyl group having the indicated number of carbon atoms (e.g., methyloxymethyl).

The term "aryl" includes a carbocyclic aromatic ring that is monocyclic, bicyclic, or polycyclic, such as phenyl, biphenyl, naphthyl, anthracenyl, phenanthrenyl, fluorenyl, indenyl, pentalenyl, azulenyl, and biphenylenyl. Aryl also includes the partially hydrogenated derivatives of the carbocyclic aromatic enumerated above. Examples of partially hydrogenated derivatives include 1,2,3,4-tetrahydronaphthyl and 1,4-dihydronaphthyl.

The term "aryl1" includes phenyl, biphenyl, naphthyl, anthracenyl, phenanthrenyl, and fluorenyl.

The term "aryl2" includes phenyl, biphenyl, and naphthyl.

The term "hetaryl" includes pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), isoxazolyl (3-isoxazolyl, 4-isoxazolyl, 5-isoxazolyl), thiazolyl (2-thiazolyl, 4-thiazolyl, 5-thiazolyl), thiophenyl (2-thiophenyl, 3-thiophenyl, 4-thiophenyl, 5-thiophenyl), furanyl (2-furanyl, 3-furanyl, 4-furanyl, 5-furanyl), pyridyl (2-pyridyl, 3-pyridyl, 4-pyridyl, 5-pyridyl), 5-tetrazolyl, pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo-[b]furanyl), 6-(2,3-dihydro-benzo-[b]furanyl), 7-(2,3-dihydro-benzo[b]furanyl)), 1,4-benzodioxin (2-(1,4-benzodioxin), 3-(1,4-benzodioxin), 5-(1,4-benzodioxin), 6-(1,4-benzodioxin)), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl (2-(2,3-dihydro-benzo[b]thiophenyl), 3-(2,3-dihydro-benzo[b]thiophenyl), 4-(2,3-dihydrobenzo[b]thiophenyl), 5-(2,3-dihydro-benzo[b]thiophenyl), 6-(2,3-dihydro-benzo[b]thiophenyl), 7-(2,3-dihydro-benzo[b]thiophenyl)), 4,5,6,7-tetrahydro-benzo[b]thiophenyl (2-(4,5,6,7-tetrahydro-benzo[b]thiophenyl), 3-(4,5,6,7-tetrahydro-benzo[b]thiophenyl), 4-(4,5,6,7-tetrahydro-benzo[b]thiophenyl), 5-(4,5,6,7-tetrahydro-benzo[b]thiophenyl), 6-(4,5,6,7-tetrahydro-benzo[b]thiophenyl), 7-(4,5,6,7-tetrahydro-benzo[b]thiophenyl)), thieno[2,3-b]thiophenyl, 4,5, 6,7-tetrahydro-thieno[2,3-c]pyridyl (4-(4,5,6,7-tetrahydro-thieno[2,3-c]pyridyl), 5-(4,5,6,7-tetrahydro-thieno[2,3-c]pyridyl), 6-(4,5,6,7-tetrahydro-thieno[2,3-c]pyridyl), 7-(4,5,6,7-tetrahydro-thieno[2,3-c]pyridyl)), indolyl (1-indolyl, 2-indolyl, 3-indolyl, 4-indolyl, 5-indolyl, 6-indolyl, 7-indolyl), isoindolyl (1-isoindolyl, 2-isoindolyl, 3-isoindolyl, 4-isoindolyl, 5-isoindolyl, 6-isoindolyl, 7-isoindolyl), 1,3-dihydro-isoindolyl (1-(1,3-dihydro-isoindolyl), 2-(1,3-dihydro-isoindolyl), 3-(1,3-dihydro-isoindolyl), 4-(1,3-dihydro-isoindolyl), 5-(1,3-dihydro-isoindolyl), 6-(1,3-dihydro-isoindolyl), 7-(1,3-dihydro-isoindolyl)), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benz-oxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), benzo-[1,2,5]oxadiazolyl, (4-benzo[1,2,5]oxadiazole, 5-benzo[1,2,5]oxadiazole), carbazolyl (1-carbazolyl, 2-carbazolyl, 3-carbazolyl, 4-carbazolyl), piperidinyl (2-piperidinyl, 3-piperidinyl, 4-piperidinyl), and pyrrolidinyl (1-pyrrolidinyl, 2-pyrrolidinyl, 3-pyrrolidinyl).

The term "arylalkyl" represents an aryl group as defined above attached through an alkyl group having the indicated number of carbon atoms (e.g., benzyl, phenylethyl, 3-phenylpropyl, 1-naphtylmethyl, and 2-(1-naphtyl)ethyl).

The term "hetarylalkyl" or "hetaralkyl" represents a hetaryl group as defined above attached through an alkyl group having the indicated number of carbon atoms (e.g., (2-furyl)methyl, (3-furyl)methyl, (2-thienyl)methyl, (3-thienyl)methyl, (2-pyridyl)methyl, and 1-methyl-1-(2-pyrimidyl)ethyl).

The term "aryloxyhetaryl" represents an aryloxy group as defined above attached through a hetaryl group (e.g., 2-phenoxy-pyridyl).

The term "aryloxy" represents an aryl group as defined above attached through an oxygen bridge (e.g., phenoxy and naphthyloxy).

The term "hetaryloxy" represents a hetaryl group as defined above attached through an oxygen bridge (e.g., 2-pyridyloxy).

The term "arylalkyloxy" represents an arylalkyl group as defined above attached through an oxygen bridge (e.g., phenethyloxy and naphthylmethyloxy).

The term "hetarylalkyloxy" represents a hetarylalkyl group as defined above attached through an oxygen bridge (e.g., 2-pyridylmethyloxy).

The term "alkyloxycarbonyl" represents an alkyloxy group as defined above attached through a carbonyl group (e.g., methylformiat and ethylformiat).

The term "aryloxycarbonyl" represents an aryloxy group as defined above attached through a carbonyl group (e.g., phenylformiat and 2-thiazolylformiat).

The term "arylalkyloxycarbonyl" represents an "arylalkyloxy" group as defined above attached through a carbonyl group (e.g., benzylformiat and phenyletylformiat).

The term "alkylthio" represents an alkyl group having the indicated number of carbon atoms attached through a sulphur bridge (e.g., methylthio and ethylthio).

The term "arylthio" represents an aryl group as defined above attached through a sulphur bridge (e.g., benzenthiol and naphthylthiol).

The term "hetarylthio" represents a hetaryl group as defined above attached through a sulphur bridge (e.g., pyridine-2-thiol and thiazole-2-thiol).

The term "arylthioalkyl" represents an arylthio group as defined above attached through an alkyl group having the indicated number of carbon atoms (e.g., methylsulfanyl benzene, and ethylsulfanyl naphthalene).

The term "hetarylthioalkyl" represents a hetarylthio group as defined above attached through an alkyl group having the indicated number of carbon atoms (e.g., 2-methylsulfanylpyridine and 1-ethylsulfanyl-isoquinoline).

The term "hetaryloxyaryl" represents a hetaryloxy group as defined above attached through an aryl group as defined above (e.g., 1-phenoxy-isoquinolyl and 2-phenoxypyridyl).

The term "hetaryloxyhetaryl" represents a hetaryloxy group as defined above attached through a hetaryl group as defined above (e.g., 1-(2-pyridyloxy-isoquinoline) and 2-(imidazol-2-yloxy-pyridine)).

The term "aryloxyalkyl" represents an aryloxy group as defined above attached through an alkyl group having the indicated number of carbon atoms (e.g., phenoxymethyl and naphthyloxyethyl).

The term "aryloxyaryl" represents an aryloxy group as defined above attached through an aryl group as defined above (e.g., 1-phenoxy-naphthalene and phenyloxyphenyl).

The term "arylalkyloxyalkyl" represents an arylalkyloxy group as defined above attached through an alkyl group having the indicated number of carbon atoms (e.g., ethoxymethyl-benzene and 2-methoxymethyl-naphthalene).

The term "hetaryloxyalkyl" represents a hetaryloxy group as defined above attached through an alkyl group having the indicated number of carbon atoms (e.g., 2-pyridyloxymethyl and 2-quinolyloxyethyl).

The term "hetarylalkyloxyalkyl" represents a hetarylalkyloxy group as defined above attached through an alkyl group having the indicated number of carbon atoms (e.g., 4-methoxymethyl-pyrimidine and 2-methoxymethyl-quinoline).

The term "alkylcarbonyl" represents an alkyl group as defined above having the indicated number of carbon atoms attached through a carbonyl group (e.g., octylcarbonyl, pentylcarbonyl, and 3-hexenylcarbonyl).

The term "arylcarbonyl" represents an aryl group as defined above attached through a carbonyl group (e.g., benzoyl).

The term "hetarylcarbonyl" represents a hetaryl group as defined above attached through a carbonyl group (e.g., 2-thiophenylcarbonyl, 3-methoxy-anthrylcarbonyl, and oxazolylcarbonyl).

The term "carbonylalkyl" represents a carbonyl group attached through an alkyl group having the indicated number of carbon atoms (e.g., acetyl).

The term "alkylcarbonylalkyl" represents an alkylcarbonyl group as defined above attached through an alkyl group having the indicated number of carbon atoms (e.g., propan-2-one and 4,4-dimethyl-pentan-2-one).

The term "arylcarbonylalkyl" represents a arylcarbonyl group as defined above attached through an alkyl group having the indicated number of carbon atoms (e.g., 1-phenylpropan-1-one and 1-(3-chloro-phenyl)-2-methyl-butan-1-one).

The term "hetarylcarbonylalkyl" represents a hetarylcarbonyl group as defined above attached through an alkyl group having the indicated number of carbon atoms (e.g., 1-pyridin-2-yl-propan-1-one and 1-(1-H-imidazol-2-yl)-propan-1-one).

The term "arylalkylcarbonyl" represents an arylalkyl group as defined above having the indicated number of carbon atoms attached through a carbonyl group (e.g., phenylpropylcarbonyl and phenylethylcarbonyl).

The term "hetarylalkylcarbonyl" represents a hetarylalkyl group as defined above wherein the alkyl group is in turn attached through a carbonyl (e.g., imidazolylpentylcarbonyl).

The term "alkylcarbonylamino" represents an "alkylcarbonyl" group as defined above wherein the carbonyl is in turn attached through the nitrogen atom of an amino group (e.g., methylcarbonylamino, cyclopentylcarbonyl-aminomethyl, and methylcarbonylaminophenyl). The nitrogen atom may itself be substituted with an alkyl or aryl group.

The term "alkylcarbonylaminoalkyl" represents an "alkylcarbonylamino" group attached through an alkyl group having the indicated number of carbon atoms (e.g. N-propylacetamide and N-butyl-propionamide).

The term "arylalkylcarbonylamino" represents an "arylalkylcarbonyl" group as defined above attached through an amino group (e.g., phenylacetamide and 3-phenyl-propionamide).

The term "arylalkylcarbonylaminoalkyl" represents an "arylalkylcarbonylamino" group attached through an alkyl group having the indicated number of carbon atoms (e.g., N-ethyl-phenylacetamide and N-butyl-3-phenyl-propionamide).

The term "arylcarbonylamino" represents an "arylcarbonyl" group as defined above attached through an amino group (e.g., benzamide and naphthalene-1-carboxylic acid amide).

The term "arylcarbonylaminoalkyl" represents an "arylcarbonylamino" group attached through an alkyl group having the indicated number of carbon atoms (e.g., N-propylbenzamide and N-Butyl-naphthalene-1-carboxylic acid amide).

The term "alkylcarboxy" represents an alkylcarbonyl group as defined above wherein the carbonyl is in turn attached through an oxygen bridge (e.g., heptylcarboxy, cyclopropyl-carboxy, and 3-pentenylcarboxy).

The term "arylcarboxy" represents an arylcarbonyl group as defined above wherein the carbonyl is in turn attached through an oxygen bridge (e.g., benzoic acid).

The term "alkylcarboxyalkyl" represents an alkylcarboxy group as defined above wherein the oxygen is attached via an alkyl bridge (e.g., heptylcarboxymethyl, propylcarboxy tert-butyl, and 3-pentylcarboxyethyl).

The term "arylalkylcarboxy" represents an arylalkylcarbonyl group as defined above wherein the carbonyl is in turn attached through an oxygen bridge (e.g., benzylcarboxy and phenylpropylcarboxy).

The term "arylalkylcarboxyalkyl" represents an arylalkylcarboxy group as defined above wherein the carboxy group is in turn attached through an alkyl group having the indicated number of carbon atoms (e.g., benzylcarboxymethyl and phenylpropylcarboxypropyl).

The term "hetarylcarboxy" represents a hetarylcarbonyl group as defined above wherein the carbonyl is in turn attached through an oxygen bridge (e.g., pyridine-2-carboxylic acid).

The term "hetarylalkylcarboxy" represents a hetarylalkylcarbonyl group as defined above wherein the carbonyl is in turn attached through an oxygen bridge (e.g., (1-H-imidazol-2-yl)-acetic acid and 3-pyrimidin-2-yl-propionic acid).

The term "alkylSO$_m$" represents an alkyl group having the number of indicated carbon atoms, wherein the alkyl group is in turn attached through a sulphur bridge wherein the sulphur is substituted with m oxygen atoms (e.g., ethylsulfonyl and ethylsulfinyl).

The term "arylSO$_m$" represents an aryl group as defined above, wherein the aryl group is in turn attached through a sulphur bridge wherein the sulphur is substituted with m oxygen atoms (e.g., phenylsulfinyl and naphthyl-2-sulfonyl).

The term "hetarylSO$_m$" represents a hetaryl group as defined above, wherein the hetaryl group is in turn attached through a sulphur bridge wherein the sulphur is substituted with m oxygen atoms (e.g., thiazol-2-sulfinyl and pyridine-2-sulfonyl).

Certain of the above defined terms may occur more than once in the structural formulae, and upon such occurrence each term shall be defined independently of the other.

The term "optionally substituted" as used herein means that the groups in question are either unsubstituted or substituted with one or more of the substituents specified. When the groups in question are substituted with more than one substituent, the substituents may be the same or different.

The term "treatment" or "treating" is defined as the management and care of a patient for the purpose of combating or alleviating the disease, condition, or disorder, and the term includes the administration of the active compound to prevent or delay the onset of the symptoms or complications; alleviating (both temporary and permanent) the symptoms or complications; and/or eliminating the disease, condition, or disorder. Thus, "treatment" or "treating" includes prevention and/or prophylaxis of the disease, condition, or disorder.

The term "pharmaceutically acceptable" is defined as being suitable for administration to humans without adverse events.

The term "prodrug" is defined as a chemically modified form of the active drug, said prodrug being administered to the patient and subsequently being converted to the active drug. Techniques for development of prodrugs are well known in the art.

DETAILED DESCRIPTION OF THE INVENTION

[1] Thus in an embodiment, the present invention provides for the novel use of a substituted amide, a prodrug thereof, or a salt thereof with a pharmaceutically acceptable acid or base, or any optical isomer or mixture of optical isomers, including a racemic mixture or any tautomeric forms, wherein the substituted amide or a prodrug thereof is of formula I:

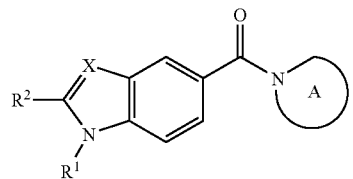

wherein:
X is selected from $CR^5$ and nitrogen;
$R^1$ is selected from H and $C_1$-$C_6$alkyl-$R^6$, wherein the alkyl group is substituted with 0-3 $R^7$;
$R^2$ is selected from hydrogen, halo, $C_1$-$C_6$alkyl, and —C(=O)$R^{13}$;
alternatively, $R^1$ and $R^2$ are, independently,

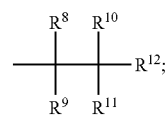

Ring A is a saturated or partially saturated bicyclic or tricyclic ring consisting of the shown nitrogen, 4-10 carbon atoms, and 0-2 additional heteroatoms selected from nitrogen, oxygen, and sulphur;

Ring A is substituted with 0-3 groups selected from $C_1$-$C_8$alkyl, halo, hydroxy, oxo, cyano, $C_1$-$C_6$alkyloxy, $C_1$-$C_6$alkyloxy$C_1$-$C_6$alkylene, and $C_1$-$C_6$alkylcarbonyl, wherein each alkyl/alkylene group is substituted with 0-3 $R^{14}$;

$R^5$ is selected from hydrogen, $C_1$-$C_6$alkyl, —C(═O)$R^{13}$, and cyano;

$R^6$ is selected from cyano, $C_3$-$C_{10}$cycloalkyl, 3-10 membered hetcycloalkyl, aryl, hetaryl, —C(═O)$R^{13}$, —S(═O)$_n R^{13}$, —S(═O)$_n$N$R^{18}R^{19}$, —N($R^{18}$)S(═O)$_n R^{13}$, —N($R^{23}$)C(═Y)N$R^{18}R^{19}$, —C(═N$R^{15}$)N$R^{15}$, —N($R^{18}$)C(═O)$R^{13}$, —N($R^{18}$)C(═O)—$C_3$-$C_{10}$cycloalkyl, —N($R^{18}$)C(═O)-3-10 membered hetcycloalkyl, —N($R^{18}$)C(═O)-aryl, —N($R^{18}$)C(═O)-hetaryl, wherein the cycloalkyl, hetcycloalkyl, aryl, and hetaryl groups are substituted with 0-3 $R^{16}$;

$R^7$ is selected from halo, hydroxy, oxo, cyano, and $C_1$-$C_8$alkyl;

$R^8$, $R^9$, $R^{10}$ and $R^{11}$ are each independently selected from hydrogen, $C_1$-$C_8$alkyl, F, trihalomethyl, trihalomethoxy, hydroxy, and $C_1$-$C_6$alkyloxy, wherein the $C_1$-$C_8$alkyl and $C_1$-$C_6$alkyloxy are substituted with 0-3 $R^{17}$;

alternatively, $R^1$ and $R^9$ together with the carbon atom to which they are attached form a saturated or partially saturated ring consisting of the carbon atom shown, 2-5 additional carbon atoms, and 0-2 heteroatoms selected from nitrogen, oxygen, and sulphur, wherein this ring is substituted with 0-3 groups selected from halo, trihalomethyl, $C_1$-$C_6$alkyl, aryl, hetaryl, aryl$C_1$-$C_6$alkylene, hetaryl$C_1$-$C_6$alkylene, hydroxy, oxo, $C_1$-$C_6$alkyloxy, aryloxy, aryl$C_1$-$C_6$alkyloxy or hetaryl$C_1$-$C_6$alkyloxy;

alternatively, $R^{10}$ and $R^{11}$ together with the carbon atom to which they are attached form a saturated or partially saturated ring consisting of the carbon atom shown, 2-5 additional carbon atoms, and 0-2 heteroatoms selected from nitrogen, oxygen, and sulphur, wherein this ring is substituted with 0-3 groups selected from halo, trihalomethyl, $C_1$-$C_6$alkyl, aryl, hetaryl, aryl$C_1$-$C_6$alkylene, hetaryl$C_1$-$C_6$alkylene, hydroxy, oxo, $C_1$-$C_6$alkyloxy, aryloxy, aryl$C_1$-$C_6$alkyloxy or hetaryl$C_1$-$C_6$alkyloxy;

alternatively, $R^8$ and $R^{10}$ together with the two carbon atoms to which they are attached form a saturated or partially saturated ring consisting of the two shown carbon atoms, 1-4 additional carbon atoms, and 0-2 heteroatoms selected from nitrogen, oxygen, and sulphur, wherein this ring is substituted with 0-3 groups selected from halo, trihalomethyl, $C_1$-$C_6$alkyl, aryl, hetaryl, aryl$C_1$-$C_6$alkylene, hetaryl$C_1$-$C_6$alkylene, hydroxy, oxo, $C_1$-$C_6$alkyloxy, aryloxy, aryl$C_1$-$C_6$alkyloxy, and hetaryl$C_1$-$C_6$alkyloxy;

$R^{12}$ is selected from H, OH, N$R^{18}R^{19}$, $C_3$-$C_{10}$cycloalkyl, 3-10 membered hetcycloalkyl, —C(═O)$R^{13}$, —S(O)$R^{13}$, S(═O)N$R^{18}R^{19}$, —N($R^{18}$)S(═O)$_n R^{13}$, and —C(═N$R^{15}$)N$R^{16}$; wherein the cycloalkyl and hetcycloalkyl groups are substituted with 0-3 $R^{17}$;

$R^{13}$ is selected from OH, $C_1$-$C_8$alkyl, $C_1$-$C_8$alkyloxy, $C_1$-$C_8$alkyloxy$C_1$-$C_4$alkylene, aryl, hetaryl, aryloxy, hetaryloxy, and N$R^{18}R^{19}$;

$R^{14}$ is selected from halo, hydroxy, oxo, and cyano;

$R^{15}$ and $R^{16}$ are independently selected from H, $C_1$-$C_8$alkyl, 3-10 membered cycloalkyl, halo, OH, cyano, —C(═O)$R^{13}$, —S(═O)$_n R^{13}$, S(═O)$_n$N$R^{18}R^{19}$, —N($R^{18}$)S(═O)$_n R^{13}$, aryl, and hetaryl, wherein the alkyl and cycloalkyl groups are substituted with 0-3 $R^{20}$;

$R^{17}$ is selected from halo, OH, oxo, nitro, cyano, —C(═O)$R^{18}$, —S(═O)$_n R^{13}$, S(═O)$_n$N$R^{18}R^{19}$, —N($R^{18}$)S(═O)$_n R^{13}$, N$R^{18}R^{19}$, $C_1$-$C_8$alkyl, $C_1$-$C_6$alkyloxy, and aryloxy;

$R^{18}$ and $R^{19}$ are independently selected from H, $C_1$-$C_8$alkyl, $C_1$-$C_8$alkyloxy, aryl, hetaryl, aryl$C_1$-$C_6$alkylene, and hetaryl$C_1$-$C_6$alkylene, wherein the alkyl/alkylene, aryl, and hetaryl groups are independently substituted with 0-3 $R^{20}$;

alternatively, $R^{18}$ and $R^{19}$, together with the nitrogen atom to which they are attached, form a saturated or partially saturated monocyclic, bicyclic, or tricyclic ring consisting of the shown nitrogen, 4-10 carbon atoms, and 0-2 additional heteroatoms selected from nitrogen, oxygen, and sulfur, wherein this ring is substituted with 0-3 $C_1$-$C_8$alkyl, aryl, hetaryl, aryl$C_1$-$C_6$alkylene, hetaryl$C_1$-$C_6$alkylene, hydroxy, oxo, $C_1$-$C_6$alkyloxy, aryl$C_1$-$C_6$alkyloxy, hetaryl$C_1$-$C_6$alkyloxy, $C_1$-$C_6$alkyloxy$C_1$-$C_6$alkyl, $C_1$-$C_6$alkylcarbonyl, arylcarbonyl, hetarylcarbonyl, aryl$C_1$-$C_6$alkylcarbonyl, hetaryl$C_1$-$C_6$alkylcarbonyl, $C_1$-$C_6$alkylcarboxy, arylcarboxy, hetarylcarboxy, aryl$C_1$-$C_6$alkyl-carboxy, and hetaryl$C_1$-$C_6$alkylcarboxy;

$R^{20}$ is selected from H, OH, oxo, halo, cyano, nitro, $C_1$-$C_6$alkyl, $C_1$-$C_6$alkyloxy, N$R^{21}R^{22}$, methylendioxo, dihalomethylendioxo, trihalomethyl, and trihalomethyloxy;

$R^{21}$ and $R^{22}$ are independently selected from H, $C_1$-$C_8$alkyl, and aryl$C_1$-$C_6$alkyl;

$R^{23}$ is selected from H and $C_1$-$C_6$alkyl;

n is selected from 0, 1, and 2;

Y is selected from O and S;

or a salt thereof with a pharmaceutically acceptable acid or base, or any optical isomer or mixture of optical isomers, including a racemic mixture, or any tautomeric forms.

[2] In another embodiment, the present invention provides the novel use of compounds of formula I, wherein:

$R^1$ is selected from H and $C_1$-$C_4$alkyl-$R^6$, wherein the alkyl group is substituted with 0-1 $R^7$;

$R^2$ is selected from hydrogen, $C_1$-$C_6$alkyl, and —C(═O)$R^{13}$;

alternatively, $R^1$ and $R^2$ are, independently, $$\begin{array}{c} R^8 \quad R^{10} \\ |\quad\quad| \\ -\!\!\!-\!\!\!-\!\!\!-\!\!\!-\!\!\!-R^{12}; \\ |\quad\quad| \\ R^9 \quad R^{11} \end{array}$$

Ring A is a saturated or partially saturated bicyclic or tricyclic ring consisting of the shown nitrogen and 7-10 carbon atoms;

Ring A is substituted with 0-3 groups selected from $C_1$-$C_4$alkyl, halo, hydroxy, and $C_1$-$C_6$alkyloxy;

$R^5$ is selected from hydrogen and $C_1$-$C_4$alkyl;

$R^6$ is selected from cyano, $C_3$-$C_6$cycloalkyl, 3-6 membered hetcycloalkyl, aryl, hetaryl, —C(═O)$R^{13}$, —S(═O)$_n R^{13}$, —S(═O)$_n$N$R^{18}R^{19}$, —N($R^{18}$)S(═O)$_n R^{13}$, —N($R^{23}$)C(═Y)N$R^{18}R^{19}$, —C(═N$R^{15}$)N$R^{15}$, —N($R^{18}$)C(═O)$R^{13}$, —N($R^{18}$)C(═O)—$C_3$-$C_6$cycloalkyl, —N($R^{18}$)C(═O)-3-6 membered hetcycloalkyl, —N($R^{18}$)C(═O)-aryl, —N($R^{18}$)C(═O)-hetaryl, wherein the cycloalkyl, hetcycloalkyl, aryl, and hetaryl groups are substituted with 0-3 $R^{16}$;

$R^7$ is selected from halo and $C_1$-$C_4$alkyl;

$R^8$, $R^9$, $R^{10}$ and $R^{11}$ are each independently selected from hydrogen and $C_1$-$C_4$alkyl;

alternatively, $R^8$ and $R^{10}$ together with the two carbon atoms to which they are attached form a saturated or partially saturated ring consisting of the two shown carbon atoms and 1-4 additional carbon atoms, wherein this ring is substituted with 0-1 groups selected from halo, trihalomethyl, hydroxyl, and $C_1$-$C_6$alkyl;

$R^{12}$ is selected from H, OH, and $NR^{18}R^{19}$;

$R^{13}$ is selected from OH, $C_1$-$C_4$alkyl, $C_1$-$C_4$alkyloxy, $C_1$-$C_4$alkyloxy$C_1$-$C_4$alkylene, aryl, hetaryl, aryloxy, hetaryloxy, and $NR^{18}R^{19}$;

$R^{15}$ and $R^{16}$ are independently selected from H, $C_1$-$C_4$alkyl, 3-6 membered cycloalkyl, halo, OH, cyano, —C(=O)$R^{13}$, —S(=O)$_n R^{13}$, S(=O)$_n NR^{18}R^{19}$, —N($R^{18}$)S(=O)$_n R^{13}$, aryl, and hetaryl, wherein the alkyl and cycloalkyl groups are substituted with 0-1 $R^{20}$;

$R^{18}$ and $R^{19}$ are independently selected from H, $C_1$-$C_4$alkyl, $C_1$-$C_4$alkyloxy, aryl, hetaryl, aryl$C_1$-$C_4$alkylene, and hetaryl$C_1$-$C_4$alkylene, wherein the alkyl/alkylene, aryl, and hetaryl groups are independently substituted with 0-1 $R^{20}$;

alternatively, $R^{18}$ and $R^{19}$, together with the nitrogen atom to which they are attached, form a saturated or partially saturated monocyclic, bicyclic, or tricyclic ring consisting of the shown nitrogen, 4-5 carbon atoms, and 0-1 additional heteroatoms selected from nitrogen, oxygen, and sulfur, wherein this ring is substituted with 0-1 $C_1$-$C_4$alkyl, aryl, hetaryl, aryl$C_1$-$C_4$alkylene, hetaryl$C_1$-$C_4$alkylene, hydroxy, and $C_1$-$C_4$alkyloxy;

$R^{20}$ is selected from H, OH, oxo, halo, cyano, nitro, $C_1$-$C_4$alkyl, $C_1$-$C_4$alkyloxy, $NR^{21}R^{22}$, trihalomethyl, and trihalomethyloxy;

$R^{21}$ and $R^{22}$ are independently selected from H, $C_1$-$C_4$alkyl, and aryl$C_1$-$C_4$alkyl;

$R^{23}$ is selected from H and $C_1$-$C_6$alkyl;

n is selected from 0, 1, and 2; and,

Y is selected from O and S.

[3] In another embodiment, the present invention provides the novel use of compounds wherein the substituted amide or prodrug thereof is of formula IA:

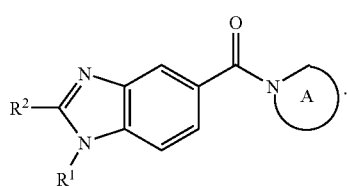

IA

[4] In another embodiment, the present invention provides the novel use of compounds wherein the substituted amide or prodrug thereof is of formula IB:

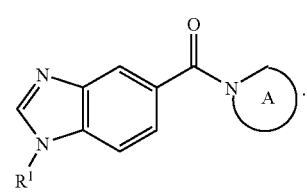

IB

[5] In another embodiment, the present invention provides the novel use of compounds wherein the substituted amide or prodrug thereof is of formula IC:

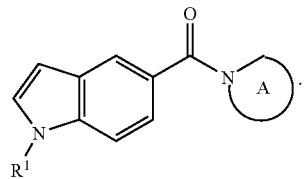

IC

[6] In another embodiment, the present invention provides the novel use of compounds wherein the substituted amide or prodrug thereof is of formula ID:

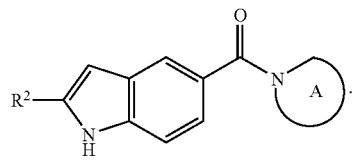

ID

[7] In another embodiment, the present invention provides the novel use of compounds of formula I, wherein:

Ring A is selected from:

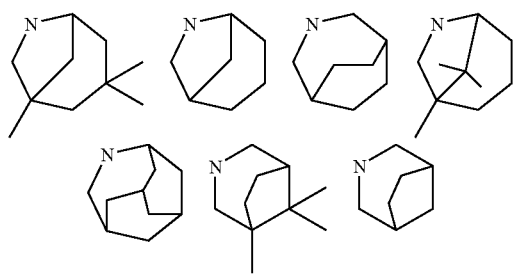

Ring A is substituted with 0-2 $R^{24}$; and, $R^{24}$ is selected from $C_1$-$C_8$alkyl, halo, hydroxy, oxo, cyano, and $C_1$-$C_6$alkyloxy.

[8] In another embodiment, the present invention provides the novel use of compounds of formula I, wherein:

Ring A is

[9] In another embodiment, the present invention provides the novel use of compounds of formula I, wherein the substituted amide or a prodrug thereof is of the selected from the group:

1 Furan-2-carboxylic acid {2-[5-(1,3,3-trimethyl-6-aza-bicyclo[3.2.1]octane-6-carbonyl)-benzoimidazol-1-yl]-ethyl}-amide 1-1 1-Acetyl-piperidine-4-carboxylic acid {2-[5-(1,3,3-trimethyl-6-aza-bicyclo[3.2.1]octane-6-carbonyl)-benzoimidazol-1-yl]-ethyl}-amide 1-2 2-Methoxy-N-{2-[5-(1,3,3-trimethyl-6-aza-bicyclo[3.2.1]octane-6-carbonyl)benzoimidazol-1-yl]-ethyl}-acetamide 1-3 N-{2-[5-(1,3,3-Trimethyl-6-aza-bicyclo[3.2.1]octane-6-carbonyl)benzoimidazol-1-yl]-ethyl}-isonicotinamide 1-4 N-{2-[5-(1,3,3-Trimethyl-6-aza-bicyclo[3.2.1]octane-6-carbonyl)benzoimidazol-1-yl]-ethyl}-acetamide 1-5 {2-[5-(1,3,3-Trimethyl-6-aza-bicyclo[3.2.1]octane-6-carbonyl)-benzoimidazol-1-yl]-ethyl}-carbamic acid tert-butyl ester 1-6 Isoxazole-5-carboxylic acid {2-[5-(1,3,3-trimethyl-6-aza-bicyclo[3.2.1]octane-6-carbonyl)-benzoimidazol-1-yl]-ethyl}-amide 1-7 N-{2-[5-(1,3,3-Trimethyl-6-aza-bicyclo[3.2.1]octane-6-carbonyl)benzoimidazol-1-yl]-ethyl}-benzamide 2 3-[2-Ethyl-5-(1,3,3-trimethyl-6-aza-bicyclo[3.2.1]octane-6-carbonyl)benzimidazol-1-yl]-propionic acid ethyl ester 3 3-[2-Ethyl-5-(1,3,3-trimethyl-6-aza-bicyclo[3.2.1]octane-6-carbonyl)benzimidazol-1-yl]-propionic acid 4 2-[5-(1,3,3-Trimethyl-6-aza-bicyclo[3.2.1]octane-6-carbonyl)-1H-benzimidazol-2-yl]-cyclopropanecarboxylic acid ethyl ester 5 2-[5-(1,3,3-Trimethyl-6-aza-bicyclo[3.2.1]octane-6-carbonyl)-1H-benzimidazol-2-yl]-cyclopropanecarboxylic acid 5-1 3-[2-Methyl-5-(1,3,3-trimethyl-6-aza-bicyclo[3.2.1]octane-6-carbonyl)benzimidazol-1-yl]-propionic acid ethyl ester 5-2 2-[1-Ethyl-5-(1,3,3-trimethyl-6-aza-bicyclo[3.2.1]octane-6-carbonyl)-1H-benzimidazol-2-yl]-cyclopropanecarboxylic acid ethyl ester 5-3 3-[2-Methyl-5-(1,3,3-trimethyl-6-aza-bicyclo[3.2.1]octane-6-carbonyl)-benzimidazol-1-yl]-propionic acid 5-4 2-[1-Ethyl-5-(1,3,3-trimethyl-6-aza-bicyclo[3.2.1]octane-6-carbonyl)-1H-benzimidazol-2-yl]-cyclopropanecarboxylic acid 6 3-[5-(1,3,3-Trimethyl-6-aza-bicyclo[3.2.1]octane-6-carbonyl)-indol-1-yl]-propionic acid ethyl ester 7 3-[5-(1,3,3-Trimethyl-6-aza-bicyclo[3.2.1]octane-6-carbonyl)-indol-1-yl]-propionic acid 7-1 [5-(1,3,3-Trimethyl-6-aza-bicyclo[3.2.1]octane-6-carbonyl)-indol-1-yl]-acetic acid tert-butyl ester 7-2 [5-(1,3,3-Trimethyl-6-aza-bicyclo[3.2.1]octane-6-carbonyl)-indol-1-yl]-acetic acid 7-3 1-Morpholin-4-yl-3-[5-(1,3,3-trimethyl-6-aza-bicyclo[3.2.1]octane-6-carbonyl)indol-1-yl]-propan-1-one 7-4 1-Morpholin-4-yl-2-[5-(1,3,3-trimethyl-6-aza-bicyclo[3.2.1]octane-6-carbonyl)indol-1-yl]-ethanone 7-5 2,2-Dimethyl-3-[5-(1,3,3-trimethyl-6-aza-bicyclo[3.2.1]octane-6-carbonyl)indol-1-yl]-propionic acid ethyl ester 7-6 2,2-Dimethyl-3-[5-(1,3,3-trimethyl-6-aza-bicyclo[3.2.1]octane-6-carbonyl)indol-1-yl]-propionic acid 7-7 2-Methyl-3-[5-(1,3,3-trimethyl-6-aza-bicyclo[3.2.1]octane-6-carbonyl)-indol-1-yl]-propionic acid methyl ester 7-8 3-[5-(1,3,3-Trimethyl-6-aza-bicyclo[3.2.1]octane-6-carbonyl)-indol-1-yl]-butyric acid methyl ester 7-9 3-[5-(1,3,3-Trimethyl-6-aza-bicyclo[3.2.1]octane-6-carbonyl)-indol-1-yl]-butyric acid 7-10 2-Methyl-3-[5-(1,3,3-trimethyl-6-aza-bicyclo[3.2.1]octane-6-carbonyl)-indol-1-yl]-propionic acid 7-11 3-[5-(1,3,3-Trimethyl-6-aza-bicyclo[3.2.1]octane-6-carbonyl)-indol-1-ylmethyl]-benzoic acid 7-12 4-[5-(1,3,3-Trimethyl-6-aza-bicyclo[3.2.1]octane-6-carbonyl)-indol-1-ylmethyl]-benzoic acid methyl ester 7-13 4-[5-(1,3,3-Trimethyl-6-aza-bicyclo[3.2.1]octane-6-carbonyl)-indol-1-ylmethyl]-benzoic acid 7-14 3-[5-(4-Aza-tricyclo[4.3.1.1*3,8*]undecane-4-carbonyl)-indol-1-yl]-propionic acid ethyl ester 7-15 3-[5-(4-Aza-tricyclo[4.3.1.1*3,8*]undecane-4-carbonyl)-indol-1-yl]-propionic acid 8 5-(1,3,3-Trimethyl-6-aza-bicyclo[3.2.1]octane-6-carbonyl)-1H-indole-2-carboxylic acid ethyl ester 9 5-(1,3,3-Trimethyl-6-aza-bicyclo[3.2.1]octane-6-carbonyl)-1H-indole-2-carboxylic acid N-Methoxy-N-methyl-3-[5-(1,3,3-trimethyl-6-aza-bicyclo[3.2.1]octane-6-carbonyl)-indol-1-yl]-propionamide N-Ethoxy-3-[5-(1,3,3-trimethyl-6-aza-bicyclo[3.2.1]octane-6-carbonyl)-indol-1-yl]-propionamide N-Hydroxy-3-[5-(1,3,3-trimethyl-6-aza-bicyclo[3.2.1]octane-6-carbonyl)-indol-1-yl]-propionamide {1-[2-(2H-Tetrazol-5-yl)-ethyl]-1H-indol-5-yl}-(1,3,3-trimethyl-6-aza-bicyclo[3.2.1]oct-6-yl)-methanone {1-[2-(3-Cyclopropyl-[1,2,4]oxadiazol-5-yl)-ethyl]-1H-indol-5-yl}-(1,3,3-trimethyl-6-aza-bicyclo[3.2.1]oct-6-yl)-methanone {1-[2-(3-Methyl-[1,2,4]oxadiazol-5-yl)-ethyl]-1H-indol-5-yl}-(1,3,3-trimethyl-6-aza-bicyclo[3.2.1]oct-6-yl)-methanone N-(1H-Tetrazol-5-yl)-3-[5-(1,3,3-trimethyl-6-aza-bicyclo[3.2.1]octane-6-carbonyl)-indol-1-yl]-propionamide {1-[2-(2-Methyl-2H-tetrazol-5-yl)-ethyl]-1H-indol-5-yl}-(1,3,3-trimethyl-6-aza-bicyclo[3.2.1]oct-6-yl)-methanone {1-[2-(1-Methyl-1H-tetrazol-5-yl)-ethyl]-1H-indol-5-yl}-(1,3,3-trimethyl-6-aza-bicyclo[3.2.1]oct-6-yl)-methanone {1-[2-(5-Methyl-[1,2,4]oxadiazol-3-yl)-ethyl]-1H-indol-5-yl}-(1,3,3-trimethyl-6-aza-bicyclo[3.2.1]oct-6-yl)-methanone or a salt thereof with a pharmaceutically acceptable acid or base, or any optical isomer or mixture of optical isomers, including a racemic mixture, or any tautomeric forms.

[10] In another embodiment, the present invention provides for the novel preparation of a pharmaceutical composition for the treatment of conditions, disorders, or diseases wherein a modulation or an inhibition of the activity of 11βHSD1 is beneficial.

[11] In another embodiment, the present invention provides for the novel preparation of a pharmaceutical composition, wherein: the conditions, disorders, and diseases that are influenced by intracellular glucocorticoid levels.

[12] In another embodiment, the present invention provides for the novel preparation of a pharmaceutical composition, wherein: the conditions, disorders, or diseases are selected from metabolic syndrome, insulin resistance, dyslipidemia, hypertension, obesity, type 2 diabetes, impaired glucose tolerance (IGT), impaired fasting glucose (IFG), the progression from IGT to type 2 diabetes, the progression of the metabolic syndrome into type 2 diabetes, diabetic late complications, neurodegenerative and psychiatric disorders, and the adverse effects of glucocorticoid receptor agonist treatment or therapy.

[13] In another embodiment, the present invention provides for the novel preparation of a pharmaceutical composition, wherein: the pharmaceutical composition is suitable for a route of administration selected from oral, nasal, buccal, transdermal, pulmonal, and parenteral.

[14] In another embodiment, the present invention provides a novel method for the treatment of conditions, disorders, or diseases wherein a modulation or an inhibition of the activity of 11βHSD1 is beneficial, the method comprising administering to a subject in need thereof an effective amount of a compound of the present invention.

[15] In another embodiment, the present invention provides a novel method wherein the conditions, disorders, and diseases that are influenced by intracellular glucocorticoid levels.

[16] In another embodiment, the present invention provides a novel method wherein the conditions, disorders, or diseases are selected from metabolic syndrome, insulin resistance, dyslipidemia, hypertension, obesity, type 2 diabetes, impaired glucose tolerance (IGT), impaired fasting glucose (IFG), progression from IGT to type 2 diabetes, progression of metabolic syndrome into type 2 diabetes, diabetic late complications, neurodegenerative and psychiatric disorders, and the adverse effects of glucocorticoid receptor agonist treatment or therapy.

[17] In another embodiment, the present invention provides a novel method wherein the administering is via a route selected from oral, nasal, buccal, transdermal, pulmonal, and parenteral.

[18] In another embodiment, the present invention provides for a novel compound of formula I:

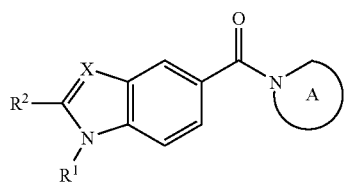

I wherein:

X is selected from $CR^5$ and nitrogen;

$R^1$ is selected from H and $C_1$-$C_6$alkyl-$R^6$, wherein the alkyl group is substituted with 0-3 $R^7$;

$R^2$ is selected from hydrogen, halo, $C_1$-$C_6$alkyl, and —C(=O)$R^{13}$;

alternatively, $R^1$ and $R^2$ are, independently,

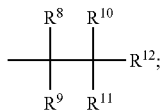

Ring A is a saturated or partially saturated bicyclic or tricyclic ring consisting of the shown nitrogen, 4-10 carbon atoms, and 0-2 additional heteroatoms selected from nitrogen, oxygen, and sulphur;

Ring A is substituted with 0-3 groups selected from $C_1$-$C_8$alkyl, halo, hydroxy, oxo, cyano, $C_1$-$C_6$alkyloxy, $C_1$-$C_6$alkyloxy$C_1$-$C_6$alkylene, and $C_1$-$C_6$alkylcarbonyl, wherein each alkyl/alkylene group is substituted with 0-3 $R^{14}$;

$R^5$ is selected from hydrogen, $C_1$-$C_6$alkyl, —C(=O)$R^{13}$, and cyano;

$R^6$ is selected from cyano, $C_3$-$C_{10}$cycloalkyl, 3-10 membered hetcycloalkyl, aryl, hetaryl, —C(=O)$R^{13}$, —S(=O)$_n$$R^{13}$, —S(=O)$_n$$NR^{18}R^{19}$, —N($R^{18}$)S(=O)$_n$$R^{13}$, —N($R^{23}$)C(=Y)$NR^{18}R^{19}$, —C(=$NR^{15}$)$NR^{15}$, —N($R^{18}$)C(=O)$R^{13}$, —N($R^{18}$)C(=O)—$C_3$-$C_{10}$cycloalkyl, —N($R^{18}$)C(=O)-3-10 membered hetcycloalkyl, —N($R^{18}$)C(=O)-aryl, —N($R^{18}$)C(=O)-hetaryl, wherein the cycloalkyl, hetcycloalkyl, aryl, and hetaryl groups are substituted with 0-3 $R^{16}$;

$R^7$ is selected from halo, hydroxy, oxo, cyano, and $C_1$-$C_8$alkyl;

$R^8$, $R^9$, $R^{10}$ and $R^{11}$ are each independently selected from hydrogen, $C_1$-$C_8$alkyl, F, trihalomethyl, trihalomethoxy, hydroxy, and $C_1$-$C_6$alkyloxy, wherein the $C_1$-$C_8$alkyl and $C_1$-$C_6$alkyloxy are substituted with 0-3 $R^{17}$;

alternatively, $R^3$ and $R^9$ together with the carbon atom to which they are attached form a saturated or partially saturated ring consisting of the carbon atom shown, 2-5 additional carbon atoms, and 0-2 heteroatoms selected from nitrogen, oxygen, and sulphur, wherein this ring is substituted with 0-3 groups selected from halo, trihalomethyl, $C_1$-$C_6$alkyl, aryl, hetaryl, aryl$C_1$-$C_6$alkylene, hetaryl$C_1$-$C_6$alkylene, hydroxy, oxo, $C_1$-$C_6$alkyloxy, aryloxy, aryl$C_1$-$C_6$alkyloxy or hetaryl$C_1$-$C_6$alkyloxy;

alternatively, $R^{10}$ and $R^{11}$ together with the carbon atom to which they are attached form a saturated or partially saturated ring consisting of the carbon atom shown, 2-5 additional carbon atoms, and 0-2 heteroatoms selected from nitrogen, oxygen, and sulphur, wherein this ring is substituted with 0-3 groups selected from halo, trihalomethyl, $C_1$-$C_6$alkyl, aryl, hetaryl, aryl$C_1$-$C_6$alkylene, hetaryl$C_1$-$C_6$alkylene, hydroxy, oxo, $C_1$-$C_6$alkyloxy, aryloxy, aryl$C_1$-$C_6$alkyloxy or hetaryl$C_1$-$C_6$alkyloxy;

alternatively, $R^8$ and $R^{10}$ together with the two carbon atoms to which they are attached form a saturated or partially saturated ring consisting of the two shown carbon atoms, 1-4 additional carbon atoms, and 0-2 heteroatoms selected from nitrogen, oxygen, and sulphur, wherein this ring is substituted with 0-3 groups selected from halo, trihalomethyl, $C_1$-$C_6$alkyl, aryl, hetaryl, aryl$C_1$-$C_6$alkylene, hetaryl$C_1$-$C_6$alkylene, hydroxy, oxo, $C_1$-$C_6$alkyloxy, aryloxy, aryl$C_1$-$C_6$alkyloxy, and hetaryl$C_1$-$C_6$alkyloxy;

$R^{12}$ is selected from H, OH, $NR^{18}R^{19}$, $C_3$-$C_{10}$cycloalkyl, 3-10 membered hetcycloalkyl, —C(=O)$R^{13}$, —S(=O)$_n$$R^{13}$, S(=O)$_n$$NR^{18}R^{19}$, —N($R^{18}$)S(=O)$_n$$R^{13}$, and —C(=$NR^{15}$)$NR^{16}$; wherein the cycloalkyl and hetcycloalkyl groups are substituted with 0-3 $R^{17}$;

$R^{13}$ is selected from OH, $C_1$-$C_8$alkyl, $C_1$-$C_8$alkyloxy, $C_1$-$C_8$alkyloxy$C_1$-$C_4$alkylene, aryl, hetaryl, aryloxy, hetaryloxy, and $NR^{18}R^{19}$;

$R^{14}$ is selected from halo, hydroxy, oxo, and cyano;

$R^{15}$ and $R^{16}$ are independently selected from H, $C_1$-$C_8$alkyl, 3-10 membered cycloalkyl, halo, OH, cyano, —C(=O)$R^{13}$, —S(=O)$_n$$R^{13}$, S(=O)$_n$$NR^{18}R^{19}$, —N($R^{18}$)S(=O)$_n$$R^{13}$, aryl, and hetaryl, wherein the alkyl and cycloalkyl groups are substituted with 0-3 $R^{20}$;

$R^{17}$ is selected from halo, OH, oxo, nitro, cyano, —C(=O)$R^{18}$, —S(=O)$_n$$R^{13}$, S(=O)$_n$$NR^{18}R^{19}$, —N($R^{18}$)S(=O)$_n$$R^{13}$, $NR^{18}R^{19}$, $C_1$-$C_8$alkyl, $C_1$-$C_6$alkyloxy, and aryloxy;

$R^{18}$ and $R^{19}$ are independently selected from H, $C_1$-$C_8$alkyl, $C_1$-$C_8$alkyloxy, aryl, hetaryl, aryl$C_1$-$C_6$alkylene, and hetaryl$C_1$-$C_6$alkylene, wherein the alkyl/alkylene, aryl, and hetaryl groups are independently substituted with 0-3 $R^{20}$;

alternatively, $R^{18}$ and $R^{19}$, together with the nitrogen atom to which they are attached, form a saturated or partially saturated monocyclic, bicyclic, or tricyclic ring consisting of the shown nitrogen, 4-10 carbon atoms, and 0-2 additional heteroatoms selected from nitrogen, oxygen, and sulfur, wherein this ring is substituted with 0-3 $C_1$-$C_8$alkyl, aryl, hetaryl, aryl$C_1$-$C_6$alkylene, hetaryl$C_1$-$C_6$alkylene, hydroxy, oxo, $C_1$-$C_6$alkyloxy, aryl$C_1$-$C_6$alkyloxy, hetaryl$C_1$-$C_6$alkyloxy, $C_1$-$C_6$alkyloxy$C_1$-$C_6$alkyl, $C_1$-$C_6$alkylcarbonyl, arylcarbonyl, hetarylcarbonyl, aryl$C_1$-$C_6$alkylcarbonyl, hetaryl$C_1$-$C_6$alkylcarbonyl, $C_1$-$C_6$alkylcarboxy, arylcarboxy, hetarylcarboxy, aryl$C_1$-$C_6$alkyl-carboxy, and hetaryl$C_1$-$C_6$alkylcarboxy;

$R^{20}$ is selected from H, OH, oxo, halo, cyano, nitro, $C_1$-$C_6$alkyl, $C_1$-$C_6$alkyloxy, $NR^{21}R^{22}$, methylendioxo, dihalomethylendioxo, trihalomethyl, and trihalomethyloxy;

$R^{21}$ and $R^{22}$ are independently selected from H, $C_1$-$C_8$alkyl, and aryl$C_1$-$C_6$alkyl;

$R^{23}$ is selected from H and $C_1$-$C_6$alkyl;

n is selected from 0, 1, and 2;

Y is selected from O and S;

or a salt thereof with a pharmaceutically acceptable acid or base, or any optical isomer or mixture of optical isomers, including a racemic mixture, or any tautomeric forms.

[19] In another embodiment, the present invention provides the novel compound of formula I, wherein:

$R^1$ is selected from H and $C_1$-$C_4$alkyl-$R^6$, wherein the alkyl group is substituted with 0-1 $R^7$;

$R^2$ is selected from hydrogen, $C_1$-$C_6$alkyl, and —C(=O)$R^{13}$;

alternatively, $R^1$ and $R^2$ are, independently,

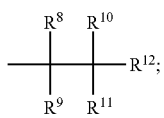

Ring A is a saturated or partially saturated bicyclic or tricyclic ring consisting of the shown nitrogen and 7-10 carbon atoms;

Ring A is substituted with 0-3 groups selected from $C_1$-$C_4$alkyl, halo, hydroxy, and $C_1$-$C_6$alkyloxy;

$R^5$ is selected from hydrogen and $C_1$-$C_4$alkyl;

$R^6$ is selected from cyano, $C_3$-$C_6$cycloalkyl, 3-6 membered hetcycloalkyl, aryl, hetaryl, —C(=O)$R^{13}$, S(=O)$_n$$R^{13}$, —S(=O)$_n$NR$^{18}$R$^{19}$, —N(R$^{18}$)S(=O)$_n$R$^{13}$, —N(R$^{23}$)C(=Y)NR$^{18}$R$^{19}$, —C(=NR$^{15}$)NR$^{15}$, —N(R$^{18}$)C(=O)R$^{13}$, —N(R$^{18}$)C(=O)—$C_3$-$C_6$cycloalkyl, —N(R$^{18}$)-3-6 membered hetcycloalkyl, —N(R$^{18}$)C(=O)-aryl, —N(R$^{18}$)C(=O)-hetaryl, wherein the cycloalkyl, hetcycloalkyl, aryl, and hetaryl groups are substituted with 0-3 $R^{16}$;

$R^7$ is selected from halo and $C_1$-$C_4$alkyl;

$R^8$, $R^9$, $R^{10}$ and $R^{11}$ are each independently selected from hydrogen and $C_1$-$C_4$alkyl;

alternatively, $R^8$ and $R^{10}$ together with the two carbon atoms to which they are attached form a saturated or partially saturated ring consisting of the two shown carbon atoms and 1-4 additional carbon atoms, wherein this ring is substituted with 0-1 groups selected from halo, trihalomethyl, hydroxyl, and $C_1$-$C_6$alkyl;

$R^{12}$ is selected from H, OH, and NR$^{18}$R$^{19}$;

$R^{13}$ is selected from OH, $C_1$-$C_4$alkyl, $C_1$-$C_4$alkyloxy, $C_1$-$C_4$alkyloxy$C_1$-$C_4$alkylene, aryl, hetaryl, aryloxy, hetaryloxy, and NR$^{18}$R$^{19}$;

$R^{15}$ and $R^{16}$ are independently selected from H, $C_1$-$C_4$alkyl, 3-6 membered cycloalkyl, halo, OH, cyano, —C(=O)$R^{13}$, —S(=O)$_n$R$^{13}$, S(=O)$_n$NR$^{18}$R$^{19}$, —N(R$^{18}$)S(=O)$_n$R$^{13}$, aryl, and hetaryl, wherein the alkyl and cycloalkyl groups are substituted with 0-1 $R^{20}$;

$R^{18}$ and $R^{19}$ are independently selected from H, $C_1$-$C_4$alkyl, $C_1$-$C_4$alkyloxy, aryl, hetaryl, aryl$C_1$-$C_4$alkylene, and hetaryl$C_1$-$C_4$alkylene, wherein the alkyl/alkylene, aryl, and hetaryl groups are independently substituted with 0-1 $R^{20}$;

alternatively, $R^{18}$ and $R^{19}$, together with the nitrogen atom to which they are attached, form a saturated or partially saturated monocyclic, bicyclic, or tricyclic ring consisting of the shown nitrogen, 4-5 carbon atoms, and 0-1 additional heteroatoms selected from nitrogen, oxygen, and sulfur, wherein this ring is substituted with 0-1 $C_1$-$C_4$alkyl, aryl, hetaryl, aryl$C_1$-$C_4$alkylene, hetaryl$C_1$-$C_4$alkylene, hydroxy, and $C_1$-$C_4$alkyloxy;

$R^{20}$ is selected from H, OH, oxo, halo, cyano, nitro, $C_1$-$C_4$alkyl, $C_1$-$C_4$alkyloxy, NR$^{21}$R$^{22}$, trihalomethyl, and trihalomethyloxy;

$R^{21}$ and $R^{22}$ are independently selected from H, $C_1$-$C_4$alkyl, and aryl$C_1$-$C_4$alkyl;

$R^{23}$ is selected from H and $C_1$-$C_6$alkyl;

n is selected from 0, 1, and 2; and,

Y is selected from O and S.

[20] In another embodiment, the present invention provides the novel compounds of formula IA:

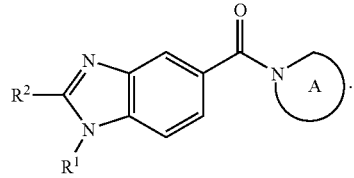

IA

[21] In another embodiment, the present invention provides the novel compounds of formula IB:

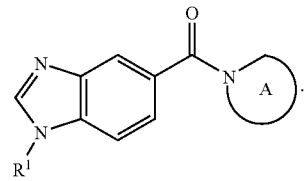

IB

[22] In another embodiment, the present invention provides the novel compounds of formula IC:

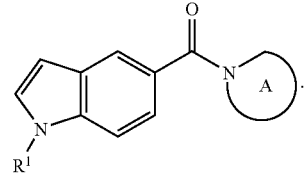

IC

[23] In another embodiment, the present invention provides the novel compounds of formula ID:

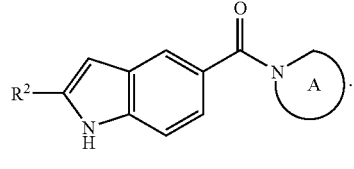

ID

[24] In another embodiment, the present invention provides the novel compounds of formula I, wherein:

Ring A is selected from:

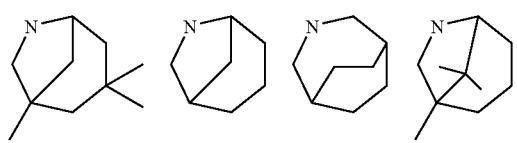

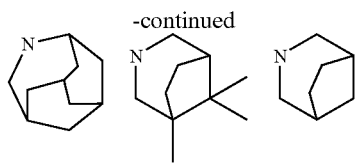

Ring A is substituted with 0-2 $R^{24}$; and,
$R^{24}$ is selected from $C_1$-$C_8$alkyl, halo, hydroxy, oxo, cyano, and $C_1$-$C_6$alkyloxy.

[25] In another embodiment, the present invention provides the novel compounds of formula I, wherein:
Ring A is

[26] In another embodiment, the present invention provides the novel compounds of formula I, selected from the group:
1 Furan-2-carboxylic acid {2-[5-(1,3,3-trimethyl-6-aza-bicyclo[3.2.1]octane-6-carbonyl)-benzoimidazol-1-yl]-ethyl}-amide
1-1 1-Acetyl-piperidine-4-carboxylic acid {2-[5-(1,3,3-trimethyl-6-aza-bicyclo[3.2.1]octane-6-carbonyl)-benzoimidazol-1-yl]-ethyl}-amide
1-2 2-Methoxy-N-{2-[5-(1,3,3-trimethyl-6-aza-bicyclo[3.2.1]octane-6-carbonyl)benzoimidazol-1-yl]-ethyl}-acetamide
1-3 N-{2-[5-(1,3,3-Trimethyl-6-aza-bicyclo[3.2.1]octane-6-carbonyl)benzoimidazol-1-yl]-ethyl}-isonicotinamide
1-4 N-{2-[5-(1,3,3-Trimethyl-6-aza-bicyclo[3.2.1]octane-6-carbonyl)benzoimidazol-1-yl]-ethyl}-acetamide
1-5 {2-[5-(1,3,3-Trimethyl-6-aza-bicyclo[3.2.1]octane-6-carbonyl)-benzoimidazol-1-yl]-ethyl}-carbamic acid tert-butyl ester
1-6 Isoxazole-5-carboxylic acid {2-[5-(1,3,3-trimethyl-6-aza-bicyclo[3.2.1]octane-6-carbonyl)-benzoimidazol-1-yl]-ethyl}-amide
1-7 N-{2-[5-(1,3,3-Trimethyl-6-aza-bicyclo[3.2.1]octane-6-carbonyl)benzoimidazol-1-yl]-ethyl}-benzamide
2 3-[2-Ethyl-5-(1,3,3-trimethyl-6-aza-bicyclo[3.2.1]octane-6-carbonyl)benzimidazol-1-yl]-propionic acid ethyl ester
3 3-[2-Ethyl-5-(1,3,3-trimethyl-6-aza-bicyclo[3.2.1]octane-6-carbonyl)benzimidazol-1-yl]-propionic acid
4 2-[5-(1,3,3-Trimethyl-6-aza-bicyclo[3.2.1]octane-6-carbonyl)-1H-benzimidazol-2-yl]-cyclopropanecarboxylic acid ethyl ester
5 2-[5-(1,3,3-Trimethyl-6-aza-bicyclo[3.2.1]octane-6-carbonyl)-1H-benzimidazol-2-yl]-cyclopropanecarboxylic acid
5-1 3-[2-Methyl-5-(1,3,3-trimethyl-6-aza-bicyclo[3.2.1]octane-6-carbonyl)benzimidazol-1-yl]-propionic acid ethyl ester
5-2 2-[1-Ethyl-5-(1,3,3-trimethyl-6-aza-bicyclo[3.2.1]octane-6-carbonyl)-1H-benzimidazol-2-yl]-cyclopropanecarboxylic acid ethyl ester
5-3 3-[2-Methyl-5-(1,3,3-trimethyl-6-aza-bicyclo[3.2.1]octane-6-carbonyl)benzimidazol-1-yl]-propionic acid
5-4 2-[1-Ethyl-5-(1,3,3-trimethyl-6-aza-bicyclo[3.2.1]octane-6-carbonyl)-1H-benzimidazol-2-yl]-cyclopropanecarboxylic acid
6 3-[5-(1,3,3-Trimethyl-6-aza-bicyclo[3.2.1]octane-6-carbonyl)-indol-1-yl]-propionic acid ethyl ester
7 3-[5-(1,3,3-Trimethyl-6-aza-bicyclo[3.2.1]octane-6-carbonyl)-indol-1-yl]-propionic acid
7-1 [5-(1,3,3-Trimethyl-6-aza-bicyclo[3.2.1]octane-6-carbonyl)-indol-1-yl]-acetic acid tert-butyl ester
7-2 [5-(1,3,3-Trimethyl-6-aza-bicyclo[3.2.1]octane-6-carbonyl)-indol-1-yl]-acetic acid
7-3 1-Morpholin-4-yl-3-[5-(1,3,3-trimethyl-6-aza-bicyclo[3.2.1]octane-6-carbonyl)indol-1-yl]-propan-1-one
7-4 1-Morpholin-4-yl-2-[5-(1,3,3-trimethyl-6-aza-bicyclo[3.2.1]octane-6-carbonyl)indol-1-yl]-ethanone
7-5 2,2-Dimethyl-3-[5-(1,3,3-trimethyl-6-aza-bicyclo[3.2.1]octane-6-carbonyl)indol-1-yl]-propionic acid ethyl ester
7-6 2,2-Dimethyl-3-[5-(1,3,3-trimethyl-6-aza-bicyclo[3.2.1]octane-6-carbonyl)indol-1-yl]-propionic acid
7-7 2-Methyl-3-[5-(1,3,3-trimethyl-6-aza-bicyclo[3.2.1]octane-6-carbonyl)-indol-1-yl]-propionic acid methyl ester
7-8 3-[5-(1,3,3-Trimethyl-6-aza-bicyclo[3.2.1]octane-6-carbonyl)-indol-1-yl]-butyric acid methyl ester
7-9 3-[5-(1,3,3-Trimethyl-6-aza-bicyclo[3.2.1]octane-6-carbonyl)-indol-1-yl]-butyric acid
7-10 2-Methyl-3-[5-(1,3,3-trimethyl-6-aza-bicyclo[3.2.1]octane-6-carbonyl)-indol-1-yl]-propionic acid
7-11 3-[5-(1,3,3-Trimethyl-6-aza-bicyclo[3.2.1]octane-6-carbonyl)-indol-1-ylmethyl]-benzoic acid
7-12 4-[5-(1,3,3-Trimethyl-6-aza-bicyclo[3.2.1]octane-6-carbonyl)-indol-1-ylmethyl]-benzoic acid methyl ester
7-13 4-[5-(1,3,3-Trimethyl-6-aza-bicyclo[3.2.1]octane-6-carbonyl)-indol-1-ylmethyl]-benzoic acid
7-14 3-[5-(4-Aza-tricyclo[4.3.1.1*3,8*]undecane-4-carbonyl)-indol-1-yl]-propionic acid ethyl ester
7-15 3-[5-(4-Aza-tricyclo[4.3.1.1*3,8*]undecane-4-carbonyl)-indol-1-yl]-propionic acid
8 5-(1,3,3-Trimethyl-6-aza-bicyclo[3.2.1]octane-6-carbonyl)-1H-indole-2-carboxylic acid ethyl ester
9 5-(1,3,3-Trimethyl-6-aza-bicyclo[3.2.1]octane-6-carbonyl)-1H-indole-2-carboxylic acid
N-Methoxy-N-methyl-3-[5-(1,3,3-trimethyl-6-aza-bicyclo[3.2.1]octane-6-carbonyl)-indol-1-yl]-propionamide
N-Ethoxy-3-[5-(1,3,3-trimethyl-6-aza-bicyclo[3.2.1]octane-6-carbonyl)-indol-1-yl]-propionamide
N-Hydroxy-3-[5-(1,3,3-trimethyl-6-aza-bicyclo[3.2.1]octane-6-carbonyl)-indol-1-yl]-propionamide
{1-[2-(2H-Tetrazol-5-yl)-ethyl]-1H-indol-5-yl}-(1,3,3-trimethyl-6-aza-bicyclo[3.2.1]oct-6-yl)-methanone
{1-[2-(3-Cyclopropyl-[1,2,4]oxadiazol-5-yl)-ethyl]-1H-indol-5-yl}-(1,3,3-trimethyl-6-aza-bicyclo[3.2.1]oct-6-yl)-methanone
{1-[2-(3-Methyl-[1,2,4]oxadiazol-5-yl)-ethyl]-1H-indol-5-yl}-(1,3,3-trimethyl-6-aza-bicyclo[3.2.1]oct-6-yl)-methanone
N-(1H-Tetrazol-5-yl)-3-[5-(1,3,3-trimethyl-6-aza-bicyclo[3.2.1]octane-6-carbonyl)-indol-1-yl]-propionamide
{1-[2-(2-Methyl-2H-tetrazol-5-yl)-ethyl]-1H-indol-5-yl}-(1,3,3-trimethyl-6-aza-bicyclo[3.2.1]oct-6-yl)-methanone
{1-[2-(1-Methyl-1H-tetrazol-5-yl)-ethyl]-1H-indol-5-yl}-(1,3,3-trimethyl-6-aza-bicyclo[3.2.1]oct-6-yl)-methanone
{1-[2-(5-Methyl-[1,2,4]oxadiazol-3-yl)-ethyl]-1H-indol-5-yl}-(1,3,3-trimethyl-6-aza-bicyclo[3.2.1]oct-6-yl)-methanone
or a salt thereof with a pharmaceutically acceptable acid or base, or any optical isomer or mixture of optical isomers, including a racemic mixture, or any tautomeric forms.

In another embodiment, the present invention provides for a novel compound of formula I:

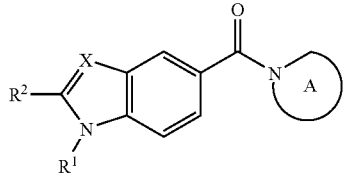

wherein:

X is selected from $CR^5$ and nitrogen;

$R^1$ is selected from $C_1$-$C_6$alkyl-$R^6$, wherein the alkyl group is substituted with 0-3 $R^7$;

$R^2$ is selected from hydrogen, halo, $C_1$-$C_6$alkyl, and —C(=O)$R^{13}$;

alternatively, $R^1$ and $R^2$ are, independently,

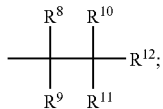

Ring A is a saturated or partially saturated bicyclic or tricyclic ring consisting of the shown nitrogen, 4-10 carbon atoms, and 0-2 additional heteroatoms selected from nitrogen, oxygen, and sulphur;

Ring A is substituted with 0-3 groups selected from $C_1$-$C_8$alkyl, halo, hydroxy, —COOH, —CONR$^{18}$R$^{19}$, —S(=O)$_n$R$^{13}$, —S(=O)$_n$NR$^{18}$R$^{19}$ oxo, cyano, $C_1$-$C_6$alkyloxy, $C_1$-$C_6$alkyloxy$C_1$-$C_6$alkylene, and $C_1$-$C_6$alkylcarbonyl, wherein each alkyl/alkylene group is substituted with 0-3 $R^{14}$;

alternatively,

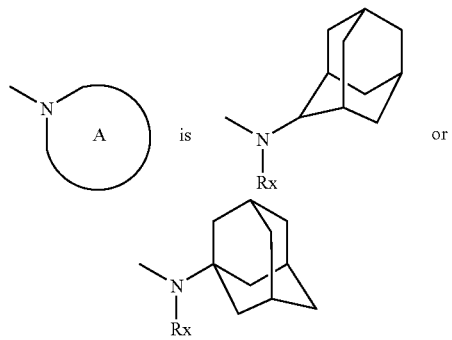

wherein Rx is selected from hydrogen and $C_1$-$C_6$alkyl;

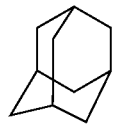

is substituted with 0-3 groups selected from $C_1$-$C_8$alkyl, halo, hydroxy, —COOH, —CONR$^{18}$R$^{19}$, —S(=O)$_n$R$^{13}$, —S(=O)$_n$NR$^{18}$R$^{19}$ oxo, cyano, $C_1$-$C_6$alkyloxy, $C_1$-$C_6$alkyloxy$C_1$-$C_6$alkylene, and $C_1$-$C_6$alkylcarbonyl, wherein each alkyl/alkylene group is substituted with 0-3 $R^{14}$;

$R^5$ is selected from hydrogen, $C_1$-$C_6$alkyl, —C(=O)$R^{13}$, and cyano;

$R^6$ is selected from cyano, aryl, hetaryl, -oxo$C_1$-$C_6$alkyl-S(=O)$_n$R$^{13}$, —C(=O)$R^{13}$, —S(=O)$_n$R$^{13}$, —S(=O)$_n$NR$^{18}$R$^{19}$, —N(R$^{18}$)S(=O)$_n$R$^{13}$, —N(R$^{23}$)C(=Y)NR$^{18}$R$^{19}$, —C(=NR$^{15}$)NR$^{15}$, —N(R$^{18}$)C(=O)R$^{13}$, —N(R$^{18}$)C(=O)—C$_3$-C$_{10}$cycloalkyl, —N(R$^{18}$)C(=O)-3-10 membered hetcycloalkyl, wherein the cycloalkyl, hetcycloalkyl, aryl, and hetaryl groups are substituted with 0-3 $R^{16}$;

$R^7$ is selected from $C_1$-$C_6$alkyl, halo, hydroxy, oxo and cyano;

$R^8$, $R^9$, $R^{10}$ and $R^{11}$ are each independently selected from hydrogen, $C_1$-$C_8$alkyl, F, trihalomethyl, trihalomethoxy, hydroxy, and $C_1$-$C_6$alkyloxy, wherein the $C_1$-$C_8$alkyl and $C_1$-$C_6$alkyloxy are substituted with 0-3 $R^{17}$;

alternatively, $R^8$ and $R^9$ together with the carbon atom to which they are attached form a saturated or partially saturated ring consisting of the carbon atom shown, 2-5 additional carbon atoms, and 0-2 heteroatoms selected from nitrogen, oxygen, and sulphur, wherein this ring is substituted with 0-3 groups selected from halo, trihalomethyl, $C_1$-$C_6$alkyl, aryl, hetaryl, aryl$C_1$-$C_6$alkylene, hetaryl$C_1$-$C_6$alkylene, hydroxy, oxo, $C_1$-$C_6$alkyloxy, aryloxy, aryl$C_1$-$C_6$alkyloxy or hetaryl$C_1$-$C_6$alkyloxy;

alternatively, $R^{10}$ and $R^{11}$ together with the carbon atom to which they are attached form a saturated or partially saturated ring consisting of the carbon atom shown, 2-5 additional carbon atoms, and 0-2 heteroatoms selected from nitrogen, oxygen, and sulphur, wherein this ring is substituted with 0-3 groups selected from halo, trihalomethyl, $C_1$-$C_6$alkyl, aryl, hetaryl, aryl$C_1$-$C_6$alkylene, hetaryl$C_1$-$C_6$alkylene, hydroxy, oxo, $C_1$-$C_6$alkyloxy, aryloxy, aryl$C_1$-$C_6$alkyloxy or hetaryl$C_1$-$C_6$alkyloxy;

alternatively, $R^8$ and $R^{10}$ together with the two carbon atoms to which they are attached form a saturated or partially saturated ring consisting of the two shown carbon atoms, 1-4 additional carbon atoms, and 0-2 heteroatoms selected from nitrogen, oxygen, and sulphur, wherein this ring is substituted with 0-3 groups selected from halo, trihalomethyl, $C_1$-$C_6$alkyl, aryl, hetaryl, aryl$C_1$-$C_6$alkylene, hetaryl$C_1$-$C_6$alkylene, hydroxy, oxo, $C_1$-$C_6$alkyloxy, aryloxy, aryl$C_1$-$C_6$alkyloxy, and hetaryl$C_1$-$C_6$alkyloxy;

$R^{12}$ is selected from H, OH, NR$^{18}$R$^{19}$, C$_3$-C$_{10}$cycloalkyl, 3-10 membered hetcycloalkyl, —C(=O)R$^{13}$, —S(=O)$_n$R$^{13}$, —S(=O)$_n$NR$^{18}$R$^{19}$, —N(R$^{18}$)S(=O)$_n$R$^{13}$, and —C(=NR$^{15}$)NR$^{16}$; wherein the cycloalkyl and hetcycloalkyl groups are substituted with 0-3 $R^{17}$;

$R^{13}$ is selected from OH, $C_1$-$C_8$alkyl, $C_1$-$C_8$alkyloxy, $C_1$-$C_8$alkyloxy$C_1$-$C_4$alkylene, aryl, hetaryl, aryloxy, hetaryloxy, and NR$^{18}$R$^{19}$;

$R^{14}$ is selected from halo, hydroxy, oxo, and cyano;

$R^{15}$ and $R^{16}$ are independently selected from H, $C_1$-$C_8$alkyl, 3-10 membered cycloalkyl, halo, OH, cyano, —C(=O)R$^{13}$, —S(=O)$_n$R$^{13}$, S(=O)$_n$NR$^{18}$R$^{19}$, —N(R$^{18}$)S(=O)$_n$R$^{13}$, aryl, and hetaryl, wherein the alkyl and cycloalkyl groups are substituted with 0-3 $R^{20}$;

$R^{17}$ is selected from halo, OH, oxo, nitro, cyano, —C(=O)R$^{18}$, —S(=O)$_n$R$^{13}$—S(=O)$_n$NR$^{18}$R$^{19}$, —N(R$^{18}$)S(=O)$_n$R$^{13}$, NR$^{18}$R$^{19}$, $C_1$-$C_8$alkyl, $C_1$-$C_6$alkyloxy, and aryloxy;

$R^{18}$ and $R^{19}$ are independently selected from H, $C_1$-$C_8$alkyl, $C_1$-$C_8$alkyloxy, aryl, hetaryl, aryl$C_1$-$C_6$alkylene, and hetaryl$C_1$-$C_6$alkylene, wherein the alkyl/alkylene, aryl, and hetaryl groups are independently substituted with 0-3 $R^{20}$;

alternatively, $R^{18}$ and $R^{19}$, together with the nitrogen atom to which they are attached, form a saturated or partially saturated monocyclic, bicyclic, or tricyclic ring consisting of the shown nitrogen, 4-10 carbon atoms, and 0-2 additional heteroatoms selected from nitrogen, oxygen, and sulfur, wherein this ring is substituted with 0-3 $C_1$-$C_8$alkyl, aryl, hetaryl, aryl$C_1$-$C_6$alkylene, hetaryl$C_1$-$C_6$alkylene, hydroxy, oxo, $C_1$-$C_6$alkyloxy, aryl$C_1$-$C_6$alkyloxy, hetaryl$C_1$-$C_6$alkyloxy, $C_1$-$C_6$alkyloxy$C_1$-$C_6$alkyl, $C_1$-$C_6$alkylcarbonyl, arylcarbonyl, hetarylcarbonyl, aryl$C_1$-$C_6$alkylcarbonyl, hetaryl$C_1$-$C_6$alkylcarbonyl, $C_1$-$C_6$alkylcarboxy, arylcarboxy, hetarylcarboxy, aryl$C_1$-$C_6$alkyl-carboxy, and hetaryl$C_1$-$C_6$alkylcarboxy;

$R^{20}$ is selected from H, OH, oxo, halo, cyano, nitro, $C_1$-$C_6$alkyl, $C_1$-$C_6$alkyloxy, $NR^{21}R^{22}$, methylendioxo, dihalomethylendioxo, trihalomethyl, and trihalomethyloxy;

$R^{21}$ and $R^{22}$ are independently selected from H, $C_1$-$C_8$alkyl, and aryl$C_1$-$C_6$alkyl;

$R^{23}$ is selected from H and $C_1$-$C_6$alkyl;

n is selected from 0, 1, and 2;

Y is selected from O and S;

or a salt thereof with a pharmaceutically acceptable acid or base, or any optical isomer or mixture of optical isomers, including a racemic mixture, or any tautomeric forms.

In another embodiment, the present invention provides for a novel compound of formula I:

I wherein:

X is selected from $CR^5$ and nitrogen;

$R^1$ is selected from $C_1$-$C_6$alkyl-$R^6$, wherein the alkyl group is substituted with 0-3 $R^7$;

$R^2$ is selected from hydrogen, halo, $C_1$-$C_6$alkyl, and —C(=O)$R^{13}$;

alternatively, $R^1$ and $R^2$ are, independently,

Ring A is a saturated or partially saturated bicyclic or tricyclic ring consisting of the shown nitrogen, 4-10 carbon atoms, and 0-2 additional heteroatoms selected from nitrogen, oxygen, and sulphur;

Ring A is substituted with 0-3 groups selected from $C_1$-$C_8$alkyl, halo, hydroxy, —COOH, —CONR$^{18}$R$^{19}$, —S(=O)$_n$R$^{13}$, —S(=O)$_n$NR$^{18}$R$^{19}$ oxo, cyano, $C_1$-$C_6$alkyloxy, $C_1$-$C_6$alkyloxy$C_1$-$C_6$alkylene, and $C_1$-$C_6$alkylcarbonyl, wherein each alkyl/alkylene group is substituted with 0-3 $R^{14}$;

alternatively,

A is or wherein Rx is selected from hydrogen and $C_1$-$C_6$alkyl;

is substituted with 0-3 groups selected from $C_1$-$C_8$alkyl, halo, hydroxy, —COOH, —CONR$^{18}$R$^{19}$, —S(=O)$_n$R$^{13}$—S(=O)$_n$NR$^{18}$R$^{19}$ oxo, cyano, $C_1$-$C_6$alkyloxy, $C_1$-$C_6$alkyloxy$C_1$-$C_6$alkylene, and $C_1$-$C_6$alkylcarbonyl, wherein each alkyl/alkylene group is substituted with 0-3 $R^{14}$;

$R^5$ is selected from hydrogen, $C_1$-$C_6$alkyl, —C(=O)$R^{13}$, and cyano;

$R^6$ is selected from cyano, aryl, hetaryl, -oxo$C_1$-$C_6$alkyl-S(=O)$_n$R$^{13}$, —C(=O)R$^{18}$, —S(=O)$_n$R$^{13}$, —S(=O)$_n$NR$^{18}$R$^{19}$, —N(R$^{18}$)S(=O)$_n$R$^{13}$, —N(R$^{23}$)C(=Y)NR$^{18}$R$^{19}$, —C(=NR$^{15}$)NR$^{15}$, —N(R$^{18}$)C(=O)R$^{13}$, —N(R$^{18}$)C(=O)—C$_3$-C$_{10}$cycloalkyl, —N(R$^{18}$)C(=O)-3-10 membered hetcycloalkyl, wherein the cycloalkyl, hetcycloalkyl, aryl, and hetaryl groups are substituted with 0-3 $R^{16}$;

$R^7$ is selected from $C_1$-$C_6$alkyl, halo, hydroxy, oxo and cyano;

$R^8$, $R^9$, $R^{10}$ and $R^{11}$ are each independently selected from hydrogen, $C_1$-$C_8$alkyl, F, trihalomethyl, trihalomethoxy, hydroxy, and $C_1$-$C_6$alkyloxy, wherein the $C_1$-$C_8$alkyl and $C_1$-$C_6$alkyloxy are substituted with 0-3 $R^{17}$;

alternatively, $R^8$ and $R^9$ together with the carbon atom to which they are attached form a saturated or partially saturated ring consisting of the carbon atom shown, 2-5 additional carbon atoms, and 0-2 heteroatoms selected from nitrogen, oxygen, and sulphur, wherein this ring is substituted with 0-3 groups selected from halo, trihalomethyl, $C_1$-$C_6$alkyl, aryl, hetaryl, aryl$C_1$-$C_6$alkylene, hetaryl$C_1$-$C_6$alkylene, hydroxy, oxo, $C_1$-$C_6$alkyloxy, aryloxy, aryl$C_1$-$C_6$alkyloxy or hetaryl$C_1$-$C_6$alkyloxy;

alternatively, $R^{10}$ and $R^{11}$ together with the carbon atom to which they are attached form a saturated or partially saturated ring consisting of the carbon atom shown, 2-5 additional carbon atoms, and 0-2 heteroatoms selected from nitrogen, oxygen, and sulphur, wherein this ring is substituted with 0-3 groups selected from halo, trihalomethyl, $C_1$-$C_6$alkyl, aryl, hetaryl, aryl$C_1$-$C_6$alkylene, hetaryl$C_1$-$C_6$alkylene, hydroxy, oxo, $C_1$-$C_6$alkyloxy, aryloxy, aryl$C_1$-$C_6$alkyloxy or hetaryl$C_1$-$C_6$alkyloxy;

alternatively, $R^8$ and $R^{10}$ together with the two carbon atoms to which they are attached form a saturated or partially saturated ring consisting of the two shown carbon atoms, 1-4 additional carbon atoms, and 0-2 heteroatoms selected from nitrogen, oxygen, and sulphur, wherein this ring is substituted with 0-3 groups selected from halo, trihalomethyl, $C_1$-$C_6$alkyl, aryl, hetaryl, aryl$C_1$-$C_6$alkylene, hetaryl$C_1$-$C_6$alkylene, hydroxy, oxo, $C_1$-$C_6$alkyloxy, aryloxy, aryl$C_1$-$C_6$alkyloxy, and hetaryl$C_1$-$C_6$alkyloxy;

$R^{12}$ is selected from H, OH, NR$^{18}$R$^{19}$, $C_3$-$C_{10}$cycloalkyl, 3-10 membered hetcycloalkyl, —C(=O)R$^{13}$, —S(=O)$_n$ R$^{13}$, —S(=O)$_n$NR$^{18}$R$^{19}$, —N(R$^{18}$)S(=O)$_n$R$^{13}$, and —C(=NR$^{15}$)NR$^{16}$; wherein the cycloalkyl and hetcycloalkyl groups are substituted with 0-3 R$^{17}$;

R$^{13}$ is selected from OH, C$_1$-C$_8$alkyl, C$_1$-C$_8$alkyloxy, C$_1$-C$_8$alkyloxyC$_1$-C$_4$alkylene, aryl, hetaryl, aryloxy, hetaryloxy, and NR$^{18}$R$^{19}$;

R$^{14}$ is selected from halo, hydroxy, oxo, and cyano;

R$^{15}$ and R$^{16}$ are independently selected from H, C$_1$-C$_8$alkyl, 3-10 membered cycloalkyl, halo, OH, cyano, —C(=O)R$^{13}$, —S(=O)$_n$R$^{13}$, S(=O)$_n$NR$^{18}$R$^{19}$, —N(R$^{18}$)S(=O)$_n$R$^{13}$, aryl, and hetaryl, wherein the alkyl and cycloalkyl groups are substituted with 0-3 R$^{20}$;

R$^{17}$ is selected from halo, OH, oxo, nitro, cyano, —C(=O)R$^{18}$, —S(=O)$_n$R$^{13}$—S(=O)$_n$NR$^{18}$R$^{19}$, —N(R$^{18}$)S(=O)$_n$R$^{13}$, NR$^{18}$R$^{19}$, C$_1$-C$_8$alkyl, C$_1$-C$_6$alkyloxy, and aryloxy;

R$^{18}$ and R$^{19}$ are independently selected from H, C$_1$-C$_8$alkyl, C$_1$-C$_8$alkyloxy, aryl, hetaryl, arylC$_1$-C$_6$alkylene, and hetarylC$_1$-C$_6$alkylene, wherein the alkyl/alkylene, aryl, and hetaryl groups are independently substituted with 0-3 R$^{20}$;

alternatively, R$^{18}$ and R$^{19}$, together with the nitrogen atom to which they are attached, form a saturated or partially saturated monocyclic, bicyclic, or tricyclic ring consisting of the shown nitrogen, 4-10 carbon atoms, and 0-2 additional heteroatoms selected from nitrogen, oxygen, and sulfur, wherein this ring is substituted with 0-3 C$_1$-C$_8$alkyl, aryl, hetaryl, arylC$_1$-C$_6$alkylene, hetarylC$_1$-C$_6$alkylene, hydroxy, oxo, C$_1$-C$_6$alkyloxy, arylC$_1$-C$_6$alkyloxy, hetarylC$_1$-C$_6$alkyloxy, C$_1$-C$_6$alkyloxyC$_1$-C$_6$alkyl, C$_1$-C$_6$alkylcarbonyl, arylcarbonyl, hetarylcarbonyl, arylC$_1$-C$_6$alkylcarbonyl, hetarylC$_1$-C$_6$alkylcarbonyl, C$_1$-C$_6$alkylcarboxy, arylcarboxy, hetarylcarboxy, arylC$_1$-C$_6$alkyl-carboxy, and hetarylC$_1$-C$_6$alkylcarboxy;

R$^{20}$ is selected from H, OH, oxo, halo, cyano, nitro, C$_1$-C$_6$alkyl, C$_1$-C$_6$alkyloxy, NR$^{21}$R$^{22}$, methylendioxo, dihalomethylendioxo, trihalomethyl, and trihalomethyloxy;

R$^{21}$ and R$^{22}$ are independently selected from H, C$_1$-C$_8$alkyl, and arylC$_1$-C$_6$alkyl;

R$^{23}$ is selected from H and C$_1$-C$_6$alkyl;

n is selected from 0, 1, and 2;

Y is selected from O and S;

provided that when X is CR$^5$, then R$^6$, is —C(=O)R$^{13}$ wherein R$^{13}$ is OH;

or a salt thereof with a pharmaceutically acceptable acid or base, or any optical isomer or mixture of optical isomers, including a racemic mixture, or any tautomeric forms.

In another embodiment, the present invention provides for a novel compound of formula I, wherein:

X is selected from CR$^5$ and nitrogen;

R$^1$ is selected from C$_1$-C$_6$alkyl-R$^6$, wherein the alkyl group is substituted with 0-3 R$^7$;

R$^2$ is selected from hydrogen, halo, C$_1$-C$_6$alkyl, and —C(=O)R$^{13}$;

alternatively, R$^1$ and R$^2$ are, independently,

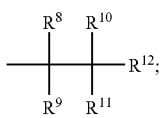

Ring A is a saturated or partially saturated bicyclic or tricyclic ring consisting of the shown nitrogen, 4-10 carbon atoms, and 0-2 additional heteroatoms selected from nitrogen, oxygen, and sulphur;

Ring A is substituted with 0-3 groups selected from C$_1$-C$_8$alkyl, halo, hydroxy, —COOH, —CONR$^{18}$R$^{19}$, —S(=O)$_n$R$^{13}$—S(=O)$_n$NR$^{18}$R$^{19}$ oxo, cyano, C$_1$-C$_6$alkyloxy, C$_1$-C$_6$alkyloxyC$_1$-C$_6$alkylene, and C$_1$-C$_6$alkylcarbonyl, wherein each alkyl/alkylene group is substituted with 0-3 R$^{14}$;

alternatively,

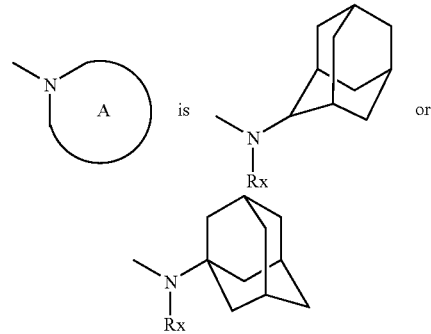

wherein Rx is selected from hydrogen and C$_1$-C$_6$alkyl;

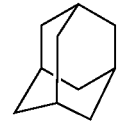

is substituted with 0-3 groups selected from C$_1$-C$_8$alkyl, halo, hydroxy, —COOH, —CONR$^{18}$R$^{19}$, —S(=O)$_n$R$^{13}$, —S(=O)$_n$NR$^{18}$R$^{19}$ oxo, cyano, C$_1$-C$_6$alkyloxy, C$_1$-C$_6$alkyloxyC$_1$-C$_6$alkylene, and C$_1$-C$_6$alkylcarbonyl, wherein each alkyl/alkylene group is substituted with 0-3 R$^{14}$;

R$^5$ is selected from hydrogen, C$_1$-C$_6$alkyl, —C(=O)R$^{13}$, and cyano;

R$^6$ is selected from cyano, aryl, hetaryl, -oxoC$_1$-C$_6$alkyl-S(=O)$_n$R$^{13}$, —C(=O)R$^{18}$, —S(=O)$_n$R$^{13}$, —S(=O)$_n$NR$^{18}$R$^{19}$, —N(R$^{18}$)S(=O)$_n$R$^{13}$, —N(R$^{23}$)C(=Y)NR$^{18}$R$^{19}$, —C(=NR$^{15}$)NR$^{15}$, —N(R$^{18}$)C(=O)R$^{13}$, —N(R$^{18}$)C(=O)—C$_3$-C$_{10}$cycloalkyl, —N(R$^{18}$)C(=O)-3-10 membered hetcycloalkyl, wherein the cycloalkyl, hetcycloalkyl, aryl, and hetaryl groups are substituted with 0-3 R$^{16}$;

R$^7$ is selected from halo, hydroxy, oxo and cyano;

R$^8$, R$^9$, R$^{10}$ and R$^{11}$ are each independently selected from hydrogen, C$_1$-C$_8$alkyl, F, trihalomethyl, trihalomethoxy, hydroxy, and C$_1$-C$_6$alkyloxy, wherein the C$_1$-C$_8$alkyl and C$_1$-C$_6$alkyloxy are substituted with 0-3 R$^{17}$;

alternatively, R$^8$ and R$^9$ together with the carbon atom to which they are attached form a saturated or partially saturated ring consisting of the carbon atom shown, 2-5 additional carbon atoms, and 0-2 heteroatoms selected from nitrogen, oxygen, and sulphur, wherein this ring is substituted with 0-3 groups selected from halo, trihalomethyl, C$_1$-C$_6$alkyl, aryl, hetaryl, arylC$_1$-C$_6$alkylene, hetarylC$_1$-C$_6$alkylene, hydroxy, oxo, C$_1$-C$_6$alkyloxy, aryloxy, arylC$_1$-C$_6$alkyloxy or hetarylC$_1$-C$_6$alkyloxy;

alternatively, R$^{10}$ and R$^{11}$ together with the carbon atom to which they are attached form a saturated or partially saturated ring consisting of the carbon atom shown, 2-5 additional carbon atoms, and 0-2 heteroatoms selected from nitrogen, oxygen, and sulphur, wherein this ring is substituted with 0-3 groups selected from halo, trihalomethyl, $C_1$-$C_6$alkyl, aryl, hetaryl, aryl$C_1$-$C_6$alkylene, hetaryl$C_1$-$C_6$alkylene, hydroxy, oxo, $C_1$-$C_6$alkyloxy, aryloxy, aryl$C_1$-$C_6$alkyloxy or hetaryl$C_1$-$C_6$alkyloxy;

alternatively, $R^8$ and $R^{10}$ together with the two carbon atoms to which they are attached form a saturated or partially saturated ring consisting of the two shown carbon atoms, 1-4 additional carbon atoms, and 0-2 heteroatoms selected from nitrogen, oxygen, and sulphur, wherein this ring is substituted with 0-3 groups selected from halo, trihalomethyl, $C_1$-$C_6$alkyl, aryl, hetaryl, aryl$C_1$-$C_6$alkylene, hetaryl$C_1$-$C_6$alkylene, hydroxy, oxo, $C_1$-$C_6$alkyloxy, aryloxy, aryl$C_1$-$C_6$alkyloxy, and hetaryl$C_1$-$C_6$alkyloxy;

$R^{12}$ is selected from H, OH, $NR^{18}R^{19}$, $C_3$-$C_{10}$cycloalkyl, 3-10 membered hetcycloalkyl, —C(=O)$R^{13}$, —S(=O)$_n R^{13}$, —S(=O)$_n NR^{18}R^{19}$, —N($R^{18}$)S(=O)$_n R^{13}$, and —C(=N$R^{15}$)$NR^{16}$; wherein the cycloalkyl and hetcycloalkyl groups are substituted with 0-3 $R^{17}$;

$R^{13}$ is selected from OH, $C_1$-$C_8$alkyl, $C_1$-$C_8$alkyloxy, $C_1$-$C_8$alkyloxy$C_1$-$C_4$alkylene, aryl, hetaryl, aryloxy, hetaryloxy, and $NR^{18}R^{19}$;

$R^{14}$ is selected from halo, hydroxy, oxo, and cyano;

$R^{15}$ and $R^{16}$ are independently selected from H, $C_1$-$C_8$alkyl, 3-10 membered cycloalkyl, halo, OH, cyano, —C(=O)$R^{13}$, —S(=O)$_n R^{13}$, S(=O)$_n NR^{18}R^{19}$, —N($R^{18}$)S(=O)$_n R^{13}$, aryl, and hetaryl, wherein the alkyl and cycloalkyl groups are substituted with 0-3 $R^{20}$;

$R^{17}$ is selected from halo, OH, oxo, nitro, cyano, —C(=O)$R^{18}$, —S(=O)$_n R^{13}$, —S(=O)$_n NR^{18}R^{19}$, —N($R^{18}$)S(=O)$_n R^{13}$, $NR^{18}R^{19}$, $C_1$-$C_8$alkyl, $C_1$-$C_6$alkyloxy, and aryloxy;

$R^{18}$ and $R^{19}$ are independently selected from H, $C_1$-$C_8$alkyl, $C_1$-$C_8$alkyloxy, aryl, hetaryl, aryl$C_1$-$C_6$alkylene, and hetaryl$C_1$-$C_6$alkylene, wherein the alkyl/alkylene, aryl, and hetaryl groups are independently substituted with 0-3 $R^{20}$;

alternatively, $R^{18}$ and $R^{19}$, together with the nitrogen atom to which they are attached, form a saturated or partially saturated monocyclic, bicyclic, or tricyclic ring consisting of the shown nitrogen, 4-10 carbon atoms, and 0-2 additional heteroatoms selected from nitrogen, oxygen, and sulfur, wherein this ring is substituted with 0-3 $C_1$-$C_8$alkyl, aryl, hetaryl, aryl$C_1$-$C_6$alkylene, hetaryl$C_1$-$C_6$alkylene, hydroxy, oxo, $C_1$-$C_6$alkyloxy, aryl$C_1$-$C_6$alkyloxy, hetaryl$C_1$-$C_6$alkyloxy, $C_1$-$C_6$alkyloxy$C_1$-$C_6$alkyl, $C_1$-$C_6$alkylcarbonyl, arylcarbonyl, hetarylcarbonyl, aryl$C_1$-$C_6$alkylcarbonyl, hetaryl$C_1$-$C_6$alkylcarbonyl, $C_1$-$C_6$alkylcarboxy, arylcarboxy, hetarylcarboxy, aryl$C_1$-$C_6$alkyl-carboxy, and hetaryl$C_1$-$C_6$alkylcarboxy;

$R^{20}$ is selected from H, OH, oxo, halo, cyano, nitro, $C_1$-$C_6$alkyl, $C_1$-$C_6$alkyloxy, $NR^{21}R^{22}$, methylendioxo, dihalomethylendioxo, trihalomethyl, and trihalomethyloxy;

$R^{21}$ and $R^{22}$ are independently selected from H, $C_1$-$C_8$alkyl, and aryl$C_1$-$C_6$alkyl;

$R^{23}$ is selected from H and $C_1$-$C_6$alkyl;

n is selected from 0, 1, and 2;

Y is selected from O and S;

provided that when X is $CR^5$, then $R^6$, is —C(=O)$R^{13}$ wherein $R^{13}$ is OH;

or a salt thereof with a pharmaceutically acceptable acid or base, or any optical isomer or mixture of optical isomers, including a racemic mixture, or any tautomeric forms.

In another embodiment, the present invention provides for a novel compound of formula I, wherein $R^1$ is $C_1$-$C_4$alkyl-$R^6$, wherein the alkyl group is substituted with 0-1 $R^7$;

$R^2$ is selected from hydrogen, $C_1$-$C_6$alkyl, and —C(=O)$R^{13}$;

alternatively, $R^1$ and $R^2$ are, independently,

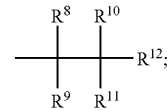

Ring A is a saturated or partially saturated bicyclic or tricyclic ring consisting of the shown nitrogen and 7-10 carbon atoms;

Ring A is substituted with 0-3 groups selected from $C_1$-$C_4$alkyl, halo, hydroxy, oxo, —COOH, —CONR$^{18}$R$^{19}$, —S(=O)$_n R^{13}$, —S(=O)$_n NR^{18}R^{19}$ and $C_1$-$C_6$alkyloxy;

alternatively,

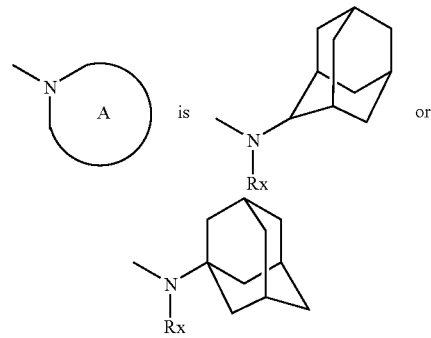

wherein Rx is selected from hydrogen and $C_1$-$C_6$alkyl;

is substituted with 0-3 groups selected from $C_1$-$C_8$alkyl, halo, hydroxy, —COOH, —CONR$^{18}$R$^{19}$, —S(=O)$_n R^{13}$, —S(=O)$_n NR^{18}R^{19}$ oxo, cyano, $C_1$-$C_6$alkyloxy, $C_1$-$C_6$alkyloxy$C_1$-$C_6$alkylene, and $C_1$-$C_6$alkylcarbonyl, wherein each alkyl/alkylene group is substituted with 0-3 $R^{14}$;

$R^5$ is selected from hydrogen and $C_1$-$C_4$alkyl;

$R^6$ is selected from cyano, aryl, hetaryl, -oxo$C_1$-$C_6$alkyl-S(=O)$_n R^{13}$, —C(=O)$R^{18}$, —S(=O)$_n R^{13}$, —S(=O)$_n NR^{18}R^{19}$, —N($R^{18}$)S(=O)$_n R^{13}$, —N($R^{23}$)C(=Y)$NR^{18}R^{19}$, —C(=N$R^{15}$)$NR^{15}$, —N($R^{18}$)C(=O)$R^{13}$, —N($R^{18}$)C(=O)—$C_3$-$C_6$cycloalkyl, —N($R^{18}$)C(=O)-3-6 membered hetcycloalkyl, wherein the cycloalkyl, hetcycloalkyl, aryl, and hetaryl groups are substituted with 0-3 $R^{16}$;

$R^7$ is selected from halo;

$R^8$, $R^9$, $R^{10}$ and $R^{11}$ are each independently selected from hydrogen and $C_1$-$C_4$alkyl;

alternatively, $R^8$ and $R^{10}$ together with the two carbon atoms to which they are attached form a saturated or partially saturated ring consisting of the two shown carbon atoms and 1-4 additional carbon atoms, wherein this ring is substituted with 0-1 groups selected from halo, trihalomethyl, hydroxyl, and $C_1$-$C_6$alkyl;

$R^{12}$ is selected from H, OH, and $NR^{18}R^{19}$;

$R^{13}$ is selected from OH, $C_1$-$C_4$alkyl, $C_1$-$C_4$alkyloxy, $C_1$-$C_4$alkyloxy$C_1$-$C_4$alkylene, aryl, hetaryl, aryloxy, hetaryloxy, and $NR^{18}R^{19}$;

$R^{15}$ and $R^{16}$ are independently selected from H, $C_1$-$C_4$alkyl, 3-6 membered cycloalkyl, halo, OH, cyano, —C(=O)$R^{13}$, —S(=O)$_n R^{13}$, —S(=O)$_n NR^{18}R^{19}$, —N($R^{18}$)S(=O)$_n R^{13}$, aryl, and hetaryl, wherein the alkyl and cycloalkyl groups are substituted with 0-1 $R^{20}$;

$R^{18}$ and $R^{19}$ are independently selected from H, $C_1$-$C_4$alkyl, $C_1$-$C_4$alkyloxy, aryl, hetaryl, aryl$C_1$-$C_4$alkylene, and hetaryl$C_1$-$C_4$alkylene, wherein the alkyl/alkylene, aryl, and hetaryl groups are independently substituted with 0-1 $R^{20}$;

alternatively, $R^{18}$ and $R^{19}$, together with the nitrogen atom to which they are attached, form a saturated or partially saturated monocyclic, bicyclic, or tricyclic ring consisting of the shown nitrogen, 4-5 carbon atoms, and 0-1 additional heteroatoms selected from nitrogen, oxygen, and sulfur, wherein this ring is substituted with 0-1 $C_1$-$C_4$alkyl, aryl, hetaryl, aryl$C_1$-$C_4$alkylene, hetaryl$C_1$-$C_4$alkylene, hydroxy, and $C_1$-$C_4$alkyloxy;

$R^{20}$ is selected from H, OH, oxo, halo, cyano, nitro, $C_1$-$C_4$alkyl, $C_1$-$C_4$alkyloxy, $NR^{21}R^{22}$, trihalomethyl, and trihalomethyloxy;

$R^{21}$ and $R^{22}$ are independently selected from H, $C_1$-$C_4$alkyl, and aryl$C_1$-$C_4$alkyl;

$R^{23}$ is selected from H and $C_1$-$C_6$alkyl;

n is selected from 0, 1, and 2; and,

Y is selected from O and S;

provided that when X is $CR^5$, then $R^6$, is —C(=O)$R^{18}$ wherein $R^{18}$ is OH;

or a salt thereof with a pharmaceutically acceptable acid or base, or any optical isomer or mixture of optical isomers, including a racemic mixture, or any tautomeric forms.

In another embodiment, the present invention provides for a novel compound of formula IA:

IA

In another embodiment, the present invention provides for a novel compound of formula IB:

IB

In another embodiment, the present invention provides for a novel compound of formula IC:

IC

In another embodiment, the present invention provides for a novel compound of formula ID:

ID

In another embodiment, the present invention provides for a novel compound of formula I wherein $R^6$ is selected from aryl, hetaryl, —C(=O)$R^{18}$, —S(=O)$_n R^{13}$, —S(=O)$_n NR^{18}R^{19}$, —N($R^{18}$)S(=O)$R^{13}$, —N($R^2$)C(=Y)$NR^{18}R^{19}$, —C(=$NR^{15}$)$NR^{15}$, —N($R^{18}$)C(=O)-aryl, or —N($R^{18}$)C(=O)-hetaryl, wherein the aryl, and hetaryl groups are substituted with 0-3 $R^{16}$.

In another embodiment, the present invention provides for a novel compound of formula I wherein $R^6$ is selected from aryl, hetaryl, -oxo$C_1$-$C_6$alkyl-S(=O)$_n R^{13}$, —C(=O)$R^{18}$, —S(=O)$_n R^{13}$, —S(=O)$_n NR^{18}R^{19}$, —N($R^{18}$)S(=O)$_n R^{13}$, —N($R^{23}$)C(=Y)$NR^{18}R^{19}$ or —C(=$NR^{15}$)$NR^{15}$; wherein the aryl, and hetaryl groups are substituted with 0-3 $R^{16}$.

In another embodiment, the present invention provides for a novel compound of formula I, wherein $R^6$ is selected from —C(=O)$R^{18}$, —S(=O)$_n R^{13}$—S(=O)$_n NR^{18}R^{19}$, —N($R^{18}$)S(=O)$_n R^{13}$, —N($R^{23}$)C(=Y)$NR^{18}R^{19}$ or —C(=$NR^{15}$)$NR^{15}$.

In another embodiment, the present invention provides for a novel compound of formula I wherein $R^6$ is selected from —C(=O)$R^{13}$, —S(=O)$_n R^{13}$, —S(=O)$_n NR^{18}R^{19}$ or —N($R^{23}$)C(=Y)$NR^{18}R^{19}$.

In another embodiment, the present invention provides for a novel compound of formula I, wherein $R^6$ is selected from —N($R^{23}$)C(=Y)$NR^{18}R^{19}$.

In another embodiment, the present invention provides for a novel compound of formula I, wherein $R^7$ is $C_1$-$C_6$alkyl.

In another embodiment, the present invention provides for a novel compound of formula I, wherein $R^7$ is halo.

In another embodiment, the present invention provides for a novel compound of formula I, wherein $R^7$ is hydroxy.

In another embodiment, the present invention provides for a novel compound of formula I, wherein $R^7$ is oxo.

In another embodiment, the present invention provides for a novel compound of formula I, wherein $R^7$ is cyano.

In another embodiment, the present invention provides for a novel compound of formula I, wherein Y is oxygen (O).

In another embodiment, the present invention provides for a novel compound of formula I, wherein Ring A is a saturated or partially saturated bicyclic or tricyclic ring consisting of the shown nitrogen, 4-10 carbon atoms, and 0-2 additional heteroatoms selected from nitrogen, oxygen, and sulphur;

Ring A is substituted with 0-3 groups selected from C$_1$-C$_8$alkyl, halo, hydroxy, —COOH, —CONR$^{18}$R$^{19}$, —S(=O)$_n$R$^{13}$, —S(=O)$_n$NR$^{18}$R$^{19}$ oxo, cyano, C$_1$-C$_6$alkyloxy, C$_1$-C$_6$alkyloxyC$_1$-C$_6$alkylene, and C$_1$-C$_6$alkylcarbonyl, wherein each alkyl/alkylene group is substituted with 0-3 R$^{14}$.

In another embodiment, the present invention provides for a novel compound of formula I, wherein Ring A is a saturated or partially saturated bicyclic or tricyclic ring consisting of the shown nitrogen, 4-10 carbon atoms, and 1-2 additional heteroatoms selected from nitrogen, oxygen, and sulphur;

Ring A is substituted with 0-3 groups selected from C$_1$-C$_4$alkyl, halo, hydroxy, oxo, —COOH, —CONR$^{18}$R$^{19}$, —S(=O)$_n$R$^{13}$, —S(=O)$_n$NR$^{18}$R$^{19}$ and C$_1$-C$_6$alkyloxy.

In another embodiment, the present invention provides for a novel compound of formula I, wherein Ring A is selected from:

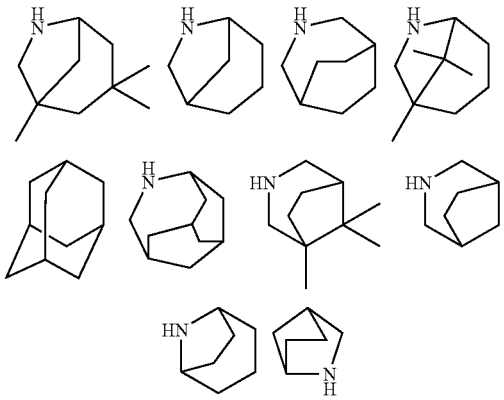

Ring A is substituted with 0-2 groups selected from C$_1$-C$_8$alkyl, halo, hydroxy, oxo, cyano, —COOH, —CONR$^{18}$R$^{19}$, —S(=O)$_n$R$^{13}$, —S(=O)$_n$NR$^{18}$R$^{19}$ and C$_1$-C$_6$alkyloxy.

In another embodiment, the present invention provides for a novel compound of formula I, wherein Ring A is

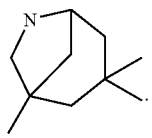

In another embodiment, the present invention provides for a novel compound of formula I wherein Ring A is

In another embodiment, the present invention provides for a novel compound of formula I, wherein Ring A is

In another embodiment, the present invention provides for a novel compound of formula I, wherein Ring A is

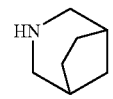

In another embodiment, the present invention provides for a novel compound of formula I, wherein Ring A is

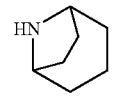

In another embodiment, the present invention provides for a novel compound of formula I, wherein Ring A is

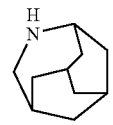

In another embodiment, the present invention provides for a novel compound of formula I, wherein

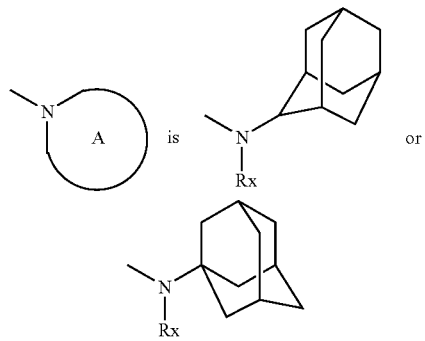

wherein Rx is selected from hydrogen and C$_1$-C$_6$alkyl;

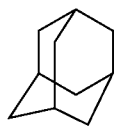

is substituted with 0-3 groups selected from C$_1$-C$_8$alkyl, halo, hydroxy, —COOH, —CONR$^{18}$R$^{19}$, —S(=O)$_n$R$^{13}$, —S(=O)$_n$NR$^{18}$R$^{19}$ oxo, cyano, C$_1$-C$_6$alkyloxy, C$_1$-C$_6$alkyloxyC$_1$-C$_6$alkylene, and C$_1$-C$_6$alkylcarbonyl, wherein each alkyl/alkylene group is substituted with 0-3 R$^{14}$.

In another embodiment, the present invention provides for a novel compound of formula I, wherein

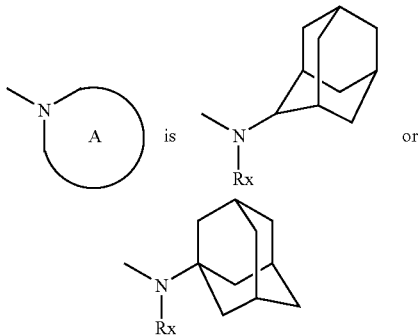

wherein Rx is selected from hydrogen and $C_1$-$C_6$alkyl;

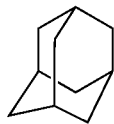

is substituted with 0-3 groups selected from $C_1$-$C_4$alkyl, halo, hydroxy, oxo, —COOH, —CONR$^{18}$R$^{19}$, —S($=$O)$_n$R$^{13}$, —S($=$O)$_n$NR$^{18}$R$^{19}$ and $C_1$-$C_6$alkyloxy.

In another embodiment, the present invention provides for a novel compound,
wherein the compound is of the selected from the group:
Furan-2-carboxylic acid {2-[5-(1,3,3-trimethyl-6-aza-bicyclo[3.2.1]octane-6-carbonyl)benzoimidazol-1-yl]-ethyl}-amide
1-Acetyl-piperidine-4-carboxylic acid {2-[5-(1,3,3-trimethyl-6-aza-bicyclo[3.2.1]octane-6-carbonyl)-benzoimidazol-1-yl]-ethyl}-amide
2-Methoxy-N-{2-[5-(1,3,3-trimethyl-6-aza-bicyclo[3.2.1]octane-6-carbonyl)-benzoimidazol-1-yl]-ethyl}-acetamide
N-{2-[5-(1,3,3-Trimethyl-6-aza-bicyclo[3.2.1]octane-6-carbonyl)-benzoimidazol-1-yl]-ethyl}-isonicotinamide
N-{2-[5-(1,3,3-Trimethyl-6-aza-bicyclo[3.2.1]octane-6-carbonyl)-benzoimidazol-1-yl]-ethyl}-acetamide
{2-[5-(1,3,3-Trimethyl-6-aza-bicyclo[3.2.1]octane-6-carbonyl)-benzoimidazol-1-yl]-ethyl}-carbamic acid tert-butyl ester
Isoxazole-5-carboxylic acid {2-[5-(1,3,3-trimethyl-6-aza-bicyclo[3.2.1]octane-6-carbonyl)benzoimidazol-1-yl]-ethyl}-amide
N-{2-[5-(1,3,3-Trimethyl-6-aza-bicyclo[3.2.1]octane-6-carbonyl)-benzoimidazol-1-yl]-ethyl}-benzamide
3-[2-Ethyl-5-(1,3,3-trimethyl-6-aza-bicyclo[3.2.1]octane-6-carbonyl)-benzimidazol-1-yl]-propionic acid ethyl ester
3-[2-Ethyl-5-(1,3,3-trimethyl-6-aza-bicyclo[3.2.1]octane-6-carbonyl)-benzimidazol-1-yl]-propionic acid
2-[5-(1,3,3-Trimethyl-6-aza-bicyclo[3.2.1]octane-6-carbonyl)-1H-benzimidazol-2-yl]-cyclopropanecarboxylic acid ethyl ester
2-[5-(1,3,3-Trimethyl-6-aza-bicyclo[3.2.1]octane-6-carbonyl)-1H-benzimidazol-2-yl]-cyclopropanecarboxylic acid
3-[2-Methyl-5-(1,3,3-trimethyl-6-aza-bicyclo[3.2.1]octane-6-carbonyl)-benzimidazol-1-yl]-propionic acid ethyl ester
2-[1-Ethyl-5-(1,3,3-trimethyl-6-aza-bicyclo[3.2.1]octane-6-carbonyl)-1H-benzimidazol-2-yl]-cyclopropanecarboxylic acid ethyl ester
3-[2-Methyl-5-(1,3,3-trimethyl-6-aza-bicyclo[3.2.1]octane-6-carbonyl)-benzimidazol-1-yl]-propionic acid
2-[1-Ethyl-5-(1,3,3-trimethyl-6-aza-bicyclo[3.2.1]octane-6-carbonyl)-1H-benzimidazol-2-yl]-cyclopropanecarboxylic acid
3-[5-(1,3,3-Trimethyl-6-aza-bicyclo[3.2.1]octane-6-carbonyl)-indol-1-yl]-propionic acid ethyl ester
3-[5-(1,3,3-Trimethyl-6-aza-bicyclo[3.2.1]octane-6-carbonyl)-indol-1-yl]-propionic acid
[5-(1,3,3-Trimethyl-6-aza-bicyclo[3.2.1]octane-6-carbonyl)-indol-1-yl]-acetic acid tert-butyl ester
[5-(1,3,3-Trimethyl-6-aza-bicyclo[3.2.1]octane-6-carbonyl)-indol-1-yl]-acetic acid
1-Morpholin-4-yl-3-[5-(1,3,3-trimethyl-6-aza-bicyclo[3.2.1]octane-6-carbonyl)-indol-1-yl]-propan-1-one
1-Morpholin-4-yl-2-[5-(1,3,3-trimethyl-6-aza-bicyclo[3.2.1]octane-6-carbonyl)-indol-1-yl]-ethanone
2,2-Dimethyl-3-[5-(1,3,3-trimethyl-6-aza-bicyclo[3.2.1]octane-6-carbonyl)-indol-1-yl]-propionic acid ethyl ester
2,2-Dimethyl-3-[5-(1,3,3-trimethyl-6-aza-bicyclo[3.2.1]octane-6-carbonyl)-indol-1-yl]-propionic acid
2-Methyl-3-[5-(1,3,3-trimethyl-6-aza-bicyclo[3.2.1]octane-6-carbonyl)-indol-1-yl]-propionic acid methyl ester
3-[5-(1,3,3-Trimethyl-6-aza-bicyclo[3.2.1]octane-6-carbonyl)-indol-1-yl]-butyric acid methyl ester
3-[5-(1,3,3-Trimethyl-6-aza-bicyclo[3.2.1]octane-6-carbonyl)-indol-1-yl]-butyric acid
2-Methyl-3-[5-(1,3,3-trimethyl-6-aza-bicyclo[3.2.1]octane-6-carbonyl)-indol-1-yl]-propionic acid
3-[5-(1,3,3-Trimethyl-6-aza-bicyclo[3.2.1]octane-6-carbonyl)-indol-1-ylmethyl]-benzoic acid
4-[5-(1,3,3-Trimethyl-6-aza-bicyclo[3.2.1]octane-6-carbonyl)-indol-1-ylmethyl]-benzoic acid methyl ester
4-[5-(1,3,3-Trimethyl-6-aza-bicyclo[3.2.1]octane-6-carbonyl)-indol-1-ylmethyl]-benzoic acid
3-[5-(4-Aza-tricyclo[4.3.1.1*3,8*]undecane-4-carbonyl)-indol-1-yl]-propionic acid ethyl ester
3-[5-(4-Aza-tricyclo[4.3.1.1*3,8*]undecane-4-carbonyl)-indol-1-yl]-propionic acid
5-(1,3,3-Trimethyl-6-aza-bicyclo[3.2.1]octane-6-carbonyl)-1H-indole-2-carboxylic acid ethyl ester
5-(1,3,3-Trimethyl-6-aza-bicyclo[3.2.1]octane-6-carbonyl)-1H-indole-2-carboxylic acid
[1-(2-Methanesulfonylmethoxy-ethyl)-1H-benzoimidazol-5-yl]-(octahydro-quinolin-1-yl)methanone
(3-Hydroxy-8-aza-bicyclo[3.2.1]oct-8-yl)-[1-(2-methanesulfonylmethoxy-ethyl)-1H-benzoimidazol-5-yl]-methanone
trans-1-(2-Methanesulfonyl-methoxy-ethyl)-1H-benzoimidazole-5-carboxylic acid (5-hydroxy-adamantan-2-yl)-amide
Cis-1-(2-Methanesulfonyl-methoxy-ethyl)-1H-benzoimidazole-5-carboxylic acid (5-hydroxy-adamantan-2-yl)-amide
(3-Hydroxy-8-aza-bicyclo[3.2.1]oct-8-yl)-[1-(2-methanesulfonylmethoxy-ethyl)-1H-benzoimidazol-5-yl]-methanone
1-(2-Methanesulfonyl-ethyl)-1H-benzoimidazole-5-carboxylic acid (5-hydroxy-adamantan-2-yl)-amide
(3-Hydroxy-8-aza-bicyclo[3.2.1]oct-8-yl)-[1-(2-methanesulfonyl-ethyl)-1H-benzoimidazol-5-yl]-methanone
(3-Hydroxy-8-aza-bicyclo[3.2.1]oct-8-yl)-[1-(2-methanesulfonyl-ethyl)-1H-benzoimidazol-5-yl]-methanone

[1-(2-Methanesulfonyl-ethyl)-1H-benzoimidazol-5-yl]-(octahydro-quinolin-1-yl)-methanone
1-(2-Methanesulfonyl-ethyl)-1H-benzoimidazole-5-carboxylic acid (5-hydroxy-adamantan-2-yl)-amide
(3-Hydroxy-8-aza-bicyclo[3.2.1]oct-8-yl)-{1-[2-(1H-tetrazol-5-yl)-ethyl]-1H-benzoimidazol-5-yl}-methanone
(Octahydro-quinolin-1-yl)-{1-[2-(1H-tetrazol-5-yl)-ethyl]-1H-benzoimidazol-5-yl}-methanone
Trans-1-[2-(1H-Tetrazol-5-yl)-ethyl]-1H-benzoimidazole-5-carboxylic acid (5-hydroxy-adamantan-2-yl)-amide
Cis-1-[2-(1H-Tetrazol-5-yl)-ethyl]-1H-benzoimidazole-5-carboxylic acid (5-hydroxy-adamantan-2-yl)-amide
3-Hydroxy-pyrrolidine-1-carboxylic acid {2-[5-(3-hydroxy-8-aza-bicyclo[3.2.1]octane-8-carbonyl)-benzoimidazol-1-yl]-ethyl}-amide
4-Hydroxy-piperidine-1-carboxylic acid {2-[5-(octahydro-quinoline-1-carbonyl)benzoimidazol-1-yl]-ethyl}-amide
1-{2-[(4-Hydroxy-piperidine-1-carbonyl)-amino]-ethyl}-1H-benzoimidazole-5-carboxylic acid (5-hydroxy-adamantan-2-yl)-amide
1-{2-[(1,1-Dioxo-thiomorpholine-4-carbonyl)-amino]-ethyl}-1H-benzoimidazole-5-carboxylic acid (5-hydroxy-adamantan-2-yl)-amide
1,1-Dioxo-thiomorpholine-4-carboxylic acid {2-[5-(3-hydroxy-8-aza-bicyclo[3.2.1]octane-8-carbonyl)-benzoimidazol-1-yl]-ethyl}-amide
Cis-1-{2-[(morpholine-4-carbonyl)-amino]-ethyl}-1H-benzo-imidazole-5-carboxylic acid (5-hydroxy-adamantan-2-yl)-amide
Trans-1-{2-[(Morpholine-4-carbonyl)-amino]-ethyl}-1H-benzo-imidazole-5-carboxylic
Cis-morpholine-4-carboxylic acid {2-[5-(octahydro-quinoline-1-carbonyl)-benzoimidazol-1-yl]-ethyl}-amide
Trans-morpholine-4-carboxylic acid {2-[5-(octahydro-quinoline-1-carbonyl)-benzoimidazol-1-yl]-ethyl}-amide
Morpholine-4-carboxylic acid {2-[5-(3-hydroxy-8-aza-bicyclo-[3.2.1]octane-8-carbonyl)benzoimidazol-1-yl]-ethyl}-amide
1,1-Dioxo-thiomorpholine-4-carboxylic acid {2-[5-(octahydro-quinoline-1-carbonyl)-benzoimidazol-1-yl]-ethyl}-amide
3-Hydroxy-pyrrolidine-1-carboxylic acid {2-[5-(octahydro-quinoline-1-carbonyl)-benzoimidazol-1-yl]-ethyl}-amide
1-{2-[5-(Octahydro-quinoline-1-carbonyl)-benzoimidazol-1-yl]-ethylcarbamoyl}-piperidine-4-carboxylic acid
3-Hydroxy-pyrrolidine-1-carboxylic acid {2-[5-(3-hydroxy-8-aza-bicyclo[3.2.1]octane-8-carbonyl)-benzoimidazol-1-yl]-ethyl}-amide
Cis-4-hydroxy-piperidine-1-carboxylic acid {2-[5-(octahydro-quinoline-1-carbonyl)-benzoimidazol-1-yl]-ethyl}-amide
Trans-4-hydroxy-piperidine-1-carboxylic acid {2-[5-(octahydro-quinoline-1-carbonyl)benzoimidazol-1-yl]-ethyl}-amide
Endo-4-hydroxy-piperidine-1-carboxylic acid {2-[5-(3-hydroxy-8-aza-bicyclo[3.2.1]octane-8-carbonyl)-benzoimidazol-1-yl]-ethyl}-amide
Exo-4-hydroxy-piperidine-1-carboxylic acid {2-[5-(3-hydroxy-8-aza-bicyclo[3.2.1]octane-8-carbonyl)-benzoimidazol-1-yl]-ethyl}-amide
1-{2-[(1,1-Dioxo-thiomorpholine-4-carbonyl)-amino]-ethyl}-1H-benzoimidazole-5-carboxylic acid (5-hydroxy-adamantan-2-yl)-amide
1,1-Dioxo-thiomorpholine-4-carboxylic acid {2-[5-(3-hydroxy-8-aza-bicyclo[3.2.1]-octane-8-carbonyl)-benzoimidazol-1-yl]-ethyl}-amide
1-{2-[(4-Hydroxy-piperidine-1-carbonyl)-amino]-ethyl}-1H-benzoimidazole-5-carboxylic acid (5-hydroxy-adamantan-2-yl)-amide
1-{2-[(3-Hydroxy-pyrrolidine-1-carbonyl)-amino]-ethyl}-1H-benzoimidazole-5-carboxylic acid (5-hydroxy-adamantan-2-yl)-amide
Morpholine-4-carboxylic acid {2-[5-(3-hydroxy-8-aza-bicyclo-[3.2.1]octane-8-carbonyl)benzoimidazol-1-yl]-ethyl}-amide
Cis-1-{2-[5-(5-hydroxy-adamantan-2-ylcarbamoyl)-benzoimidazol-1-yl]-ethylcarbamoyl}-piperidine-4-carboxylic acid
Trans-1-{2-[5-(5-hydroxy-adamantan-2-ylcarbamoyl)-benzoimidazol-1-yl]-ethylcarbamoyl}-piperidine-4-carboxylic acid
1-{2-[5-(3-Hydroxy-8-aza-bicyclo[3.2.1]octane-8-carbonyl)-benzoimidazol-1-yl]-ethylcarbamoyl}-piperidine-4-carboxylic acid
N-Methoxy-N-methyl-3-[5-(1,3,3-trimethyl-6-aza-bicyclo[3.2.1]octane-6-carbonyl)-indol-1-yl]-propionamide
N-Ethoxy-3-[5-(1,3,3-trimethyl-6-aza-bicyclo[3.2.1]octane-6-carbonyl)-indol-1-yl]-propionamide
N-Hydroxy-3-[5-(1,3,3-trimethyl-6-aza-bicyclo[3.2.1]octane-6-carbonyl)-indol-1-yl]-propionamide
{1-[2-(2H-Tetrazol-5-yl)-ethyl]-1H-indol-5-yl}-(1,3,3-trimethyl-6-aza-bicyclo[3.2.1]oct-6-yl)methanone
{1-[2-(3-Cyclopropyl-[1,2,4]oxadiazol-5-yl)-ethyl]-1H-indol-5-yl}-(1,3,3-trimethyl-6-aza-bicyclo[3.2.1]oct-6-yl)-methanone
{1-[2-(3-Methyl-[1,2,4]oxadiazol-5-yl)-ethyl]-1H-indol-5-yl}-(1,3,3-trimethyl-6-aza-bicyclo[3.2.1]oct-6-yl)-methanone
N-(1H-Tetrazol-5-yl)-3-[5-(1,3,3-trimethyl-6-aza-bicyclo[3.2.1]octane-6-carbonyl)-indol-1-yl]-propionamide
{1-[2-(2-Methyl-2H-tetrazol-5-yl)-ethyl]-1H-indol-5-yl}-(1,3,3-trimethyl-6-aza-bicyclo[3.2.1]oct-6-yl)-methanone
{1-[2-(1-Methyl-1H-tetrazol-5-yl)-ethyl]-1H-indol-5-yl}-(1,3,3-trimethyl-6-aza-bicyclo[3.2.1]oct-6-yl)-methanone
{1-[2-(5-Methyl-[1,2,4]oxadiazol-3-yl)-ethyl]-1H-indol-5-yl}-(1,3,3-trimethyl-6-aza-bicyclo[3.2.1]oct-6-yl)-methanone;
or a salt thereof with a pharmaceutically acceptable acid or base, or any optical isomer or mixture of optical isomers, including a racemic mixture, or any tautomeric forms.

In another embodiment, the present invention provides for a novel compound of formula I, which is an agent useful for the treatment of conditions, disorders, or diseases wherein a modulation or an inhibition of the activity of 11βHSD1 is beneficial.

In another embodiment, the present invention provides for a use of a compound of formula I, for the preparation of a pharmaceutical composition for the treatment of conditions, disorders, or diseases wherein a modulation or an inhibition of the activity of 11βHSD1 is beneficial.

In another embodiment, the present invention provides for a use of a compound of formula I for the preparation of a pharmaceutical composition for the treatment of conditions, disorders, or diseases, wherein the conditions, disorders, and diseases are influenced by intracellular glucocorticoid levels.

In another embodiment, the present invention provides for a use of a compound of formula I for the preparation of a pharmaceutical composition for the treatment of conditions, disorders, or diseases, wherein the conditions, disorders, or diseases are selected from metabolic syndrome, insulin resistance, dyslipidemia, hypertension, obesity, type 2 diabetes, impaired glucose tolerance (IGT), impaired fasting glucose (IFG), the progression from IGT to type 2 diabetes, the progression of the metabolic syndrome into type 2 diabetes, diabetic late complications, neurodegenerative and psychiatric disorders, and the adverse effects of glucocorticoid receptor agonist treatment or therapy.

In another embodiment, the present invention provides for a method for the treatment of conditions, disorders, or diseases wherein a modulation or an inhibition of the activity of 11βHSD1 is beneficial, the method comprising administering to a subject in need thereof an effective amount of a compound of formula I.

In another embodiment, the present invention provides for a method for the treatment of conditions, disorders or diseases, wherein the conditions, disorders, and diseases are influenced by intracellular glucocorticoid levels, the method comprising administering to a subject in need thereof an effective amount of a compound of formula I.

In another embodiment, the present invention provides for a method for the treatment of conditions, disorders or diseases, wherein the conditions, disorders or diseases are selected from metabolic syndrome, insulin resistance, dyslipidemia, hypertension, obesity, type 2 diabetes, impaired glucose tolerance (IGT), impaired fasting glucose (IFG), progression from IGT to type 2 diabetes, progression of metabolic syndrome into type 2 diabetes, diabetic late complications, neurodegenerative and psychiatric disorders, and the adverse effects of glucocorticoid receptor agonist treatment or therapy.

[27] In another embodiment, the present invention provides a novel compound, which is an agent useful for the treatment of conditions, disorders, or diseases wherein a modulation or an inhibition of the activity of 11βHSD1 is beneficial.

[28] In another embodiment, the present invention provides a novel method wherein the conditions, disorders, and diseases that are influenced by intracellular glucocorticoid levels.

[29] In another embodiment, the present invention provides a novel method wherein the conditions, disorders, or diseases are selected from metabolic syndrome, insulin resistance, dyslipidemia, hypertension, obesity, type 2 diabetes, impaired glucose tolerance (IGT), impaired fasting glucose (IFG), progression from IGT to type 2 diabetes, progression of metabolic syndrome into type 2 diabetes, diabetic late complications, neurodegenerative and psychiatric disorders, and the adverse effects of glucocorticoid receptor agonist treatment or therapy.

[30] In another embodiment, the present invention provides a novel method pharmaceutical composition comprising, as an active ingredient, at least one compound according of the present invention together with one or more pharmaceutically acceptable carriers or excipients.

[31] In another embodiment, the present invention provides a novel pharmaceutical composition, which is suitable for oral, nasal, buccal, transdermal, pulmonal, or parenteral administration.

The compounds of the present invention may have asymmetric centers and may occur as racemates, racemic mixtures, and as individual enantiomers or diastereoisomers, with all isomeric forms being included in the present invention as well as mixtures thereof.

The present invention also encompasses pharmaceutically acceptable salts of the present compounds. Such salts include pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, and nitric acids. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, and ketoglutarates. Further examples of pharmaceutically acceptable inorganic or organic acid addition salts include the pharmaceutically acceptable salts listed in J. Pharm. Sci., 66, 2 (1977), which is incorporated herein by reference. Examples of metal salts include lithium, sodium, potassium, barium, calcium, magnesium, zinc, and calcium salts. Examples of amines and organic amines include ammonium, methylamine, dimethylamine, trimethylamine, ethylamine, diethylamine, propylamine, butylamine, tetramethylamine, ethanolamine, diethanolamine, triethanolamine, meglumine, ethylenediamine, choline, N,N'-dibenzylethylenediamine, N-benzylphenylethylamine, N-methyl-D-glucamine, and guanidine. Examples of cationic amino acids include lysine, arginine, and histidine.

Further, some of the compounds of the present invention may form solvates with water or common organic solvents. Such solvates are encompassed within the scope of the invention.

The pharmaceutically acceptable salts are prepared by reacting a compound of the present invention with 1 to 4 equivalents of a base such as sodium hydroxide, sodium methoxide, sodium hydride, potassium tert-butoxide, calcium hydroxide, and magnesium hydroxide, in solvents such as ether, THF, methanol, tert-butanol, dioxane, and isopropanol, ethanol. Mixtures of solvents may be used. Organic bases such as lysine, arginine, diethanolamine, choline, guandine and their derivatives etc. may also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid salicylic acid, hydroxynaphthoic acid, ascorbic acid, palmitic acid, succinic acid, benzoic acid, benzenesulfonic acid, and tartaric acid in solvents such as ethyl acetate, ether, alcohols, acetone, THF, and dioxane. Mixture of solvents may also be used.

The stereoisomers of the compounds forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, enzymatic resolution, resolving the diastereomeric salts formed with chiral acids such as mandelic acid, camphorsulfonic acid, tartaric acid, and lactic acid, wherever applicable or chiral bases such as brucine, (R)- or (S)-phenylethylamine, cinchona alkaloids and their derivatives. Commonly used methods are compiled by Jaques et al. in "Enantiomers, Racemates and Resolution" (Wiley Interscience, 1981). More specifically the compound of the present invention may be converted to a 1:1 mixture of diastereomeric amides by treating with chiral amines, aminoacids, aminoalcohols derived from aminoacids; conventional reaction conditions may be employed to convert acid into an amide; the diastereomers may be separated either by fractional crystallization or chromatography and the stereoisomers of compound of formula I may be prepared by hydrolysing the pure diastereomeric amide.

Various polymorphs of the compounds forming part of this invention may be prepared by crystallization of said compounds under different conditions. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, ir spectroscopy, differential scanning calorimetry, powder X-ray diffraction or such other techniques.

The invention also encompasses prodrugs of the present compounds, which on administration undergo chemical conversion by metabolic processes before becoming active pharmacological substances. In general, such prodrugs will be functional derivatives of the present compounds, which are readily convertible in vivo into the required compound of the present invention. Conventional procedures for the selection and preparation of suitable prodrug derivatives are described, for example, in "Design of Prodrugs", ed. H. Bundgaard, Elsevier, 1985.

It is a well known problem in drug discovery that compounds, such as enzyme inhibitors, may be very potent and selective in biochemical assays, yet be inactive in vivo. This lack of so-called bioavailability may be ascribed to a number of different factors such as lack of or poor absorption in the gut, first pass metabolism in the liver and/or poor uptake in cells. Although the factors determining bioavailability are not completely understood, there are many examples in the scientific literature—well known to those skilled in the art—of how to modify compounds, which are potent and selective in biochemical assays but show low or no activity in vivo, into drugs that are biologically active.

It is within the scope of the invention to modify the compounds of the present invention, termed the 'original compound', by attaching chemical groups that will improve the bioavailability of said compounds in such a way that the uptake in cells or mammals is facilitated.

Examples of said modifications, which are not intended in any way to limit the scope of the invention, include changing of one or more carboxy groups to esters (for instance methyl esters, ethyl esters, tert-butyl, acetoxymethyl, pivaloyloxymethyl esters or other acyloxymethyl esters). Compounds of the invention, original compounds, such modified by attaching chemical groups are termed 'modified compounds'.

The invention also encompasses active metabolites of the present compounds.

The compounds according to the invention alter, and more specifically, reduce the level of active intracellular glucocorticoid and are accordingly useful for the treatment of conditions, disorders, and diseases in which such a modulation or reduction is beneficial.

Accordingly, the present compounds may be applicable for the treatment of the metabolic syndrome, insulin resistance, dyslipidemia, hypertension, obesity, type 2 diabetes, impaired glucose tolerance (IGT), impaired fasting glucose (IFG), Latent Autoimmune Diabetes in the Adult (LADA), type 1 diabetes, diabetic late complications including cardiovascular diseases, cardiovascular disorders, disorders of lipid metabolism, neurodegenerative and psychiatric disorders, dysregulation of intraocular pressure including glaucoma, immune disorders, inappropriate immune responses, musculo-skeletal disorders, gastrointestinal disorders, polycystic ovarie syndrome (PCOS), reduced hair growth or other diseases, disorders or conditions that are influenced by intracellular glucocorticoid levels, adverse effects of increased blood levels of active endogenous or exogenous glucocorticoid, and any combination thereof, adverse effects of increased plasma levels of endogenous active glucocorticoid, Cushing's disease, Cushing's syndrome, adverse effects of glucocorticoid receptor agonist treatment of autoimmune diseases, adverse effects of glucocorticoid receptor agonist treatment of inflammatory diseases, adverse effects of glucocorticoid receptor agonist treatment of diseases with an inflammatory component, adverse effects of glucocorticoid receptor agonist treatment as a part of cancer chemotherapy, adverse effects of glucocorticoid receptor agonist treatment for surgical/post-surgical or other trauma, adverse effects of glucocorticoid receptor agonist therapy in the context of organ or tissue transplantation or adverse effects of glucocorticoid receptor agonist treatment in other diseases, disorders or conditions where glucocorticoid receptor agonists provide clinically beneficial effects. Also the present compounds may be applicable for the treatment of visceral fat accumulation and insulin resistance in HAART (highly active antiretroviral treatment)-treated patients.

More specifically the present compounds may be applicable for the treatment of the metabolic syndrome, type 2 diabetes, diabetes as a consequence of obesity, insulin resistance, hyperglycemia, prandial hyperglycemia, hyperinsulinemia, inappropriately low insulin secretion, impaired glucose tolerance (IGT), impaired fasting glucose (IFG), increased hepatic glucose production, type 1 diabetes, LADA, pediatric diabetes, dyslipidemia, diabetic dyslipidemia, hyperlipidemia, hypertriglyceridemia, hyperlipoproteinemia, hypercholesterolemia, decreased HDL cholesterol, impaired LDL/HDL ratio, other disorders of lipid metabolism, obesity, visceral obesity, obesity as a consequence of diabetes, increased food intake, hypertension, diabetic late complications, micro-/macroalbuminuria, nephropathy, retinopathy, neuropathy, diabetic ulcers, cardiovascular diseases, arteriosclerosis, atherosclerosis, coronary artery disease, cardiac hypertrophy, myocardial ischemia, heart insufficiency, congestional heart failure, stroke, myocardial infarction, arrhythmia, decreased blood flow, erectile dysfunction (male or female), myopathy, loss of muscle tissue, muscle wasting, muscle catabolism, osteoporosis, decreased linear growth, neurodegenerative and psychiatric disorders, Alzheimers disease, neuronal death, impaired cognitive function, depression, anxiety, eating disorders, appetite regulation, migraine, epilepsy, addiction to chemical substances, disorders of intraocular pressure, glaucoma, polycystic ovary syndrome (PCOS), inappropriate immune responses, inappropriate T helper-1/T helper-2 polarisation, bacterial infections, mycobacterial infections, fungal infections, viral infections, parasitic infestations, suboptimal responses to immunizations, immune dysfunction, partial or complete baldness, or other diseases, disorders or conditions that are influenced by intracellular glucocorticoid levels and any combination thereof, adverse effects of glucocorticoid receptor agonist treatment of allergic-inflammatory diseases such as asthma and atopic dermatitis, adverse effects of glucocorticoid receptor agonist treatment of disorders of the respiratory system e.g., asthma, cystic fibrosis, emphysema, bronchitis, hypersensitivity, pneumonitis, eosinophilic pneumonias, pulmonary fibrosis, adverse effects of glucocorticoid receptor agonist treatment of inflammatory bowel disease such as Crohn's disease and ulcerative colitis; adverse effects of glucocorticoid receptor agonist treatment of disorders of the immune system, connective tissue and joints e.g., reactive arthritis, rheumatoid arthritis, Sjögren's syndrome, systemic lupus erythematosus, lupus nephritis, Henoch-Schönlein purpura, Wegener's granulomatosis, temporal arteritis, systemic sclerosis, vasculitis, sarcoidosis, dermatomyositis-polymyositis, pemphigus vulgaris; adverse effects of glucocorticoid receptor agonist treatment of endocrinological diseases such as hyperthyroidism, hypoaldosteronism, hypopituitarism; adverse effects of glucocorticoid receptor agonist treatment of hematological diseases e.g., hemolytic anemia, thrombocytopenia, paroxysmal nocturnal hemoglobinuria; adverse effects of glucocorticoid receptor agonist treatment of cancer such as spinal cord diseases, neoplastic compression of the spinal cord, brain tumours, acute lymphoblastic leukemia, Hodgkin's disease, chemotherapy-induced nausea, adverse effects of glucocorticoid receptor agonist treatment of diseases of muscle and at the neuro-muscular joint e.g., myasthenia gravis and heriditary myopathies (e.g., Duchenne muscular dystrophy), adverse effects of glucocorticoid receptor agonist treatment in the context of surgery & transplantation e.g., trauma, post-surgical stress, surgical stress, renal transplantation, liver transplantation, lung transplantation, pancreatic islet transplantation, blood stem cell transplantation, bone marrow transplantation, heart transplantation, adrenal gland transplantation, tracheal transplantation, intestinal transplantation, corneal transplantation, skin grafting, keratoplasty, lens implantation and other procedures where immunosuppression with glucocorticoid receptor agonists is beneficial; adverse effects of glucocorticoid receptor agonist treatment of brain absess, nausea/vomiting, infections, hypercalcemia, adrenal hyperplasia, autoimmune hepatitis, spinal cord diseases, saccular aneurysms or adverse effects to glucocorticoid receptor agonist treatment in other diseases, disorders and conditions where glucocorticoid receptor agonists provide clinically beneficial effects.

Accordingly, in a further aspect the invention relates to a compound according to the invention for use as a pharmaceutical composition.

The invention also relates to pharmaceutical compositions comprising, as an active ingredient, at least one compound according to the invention together with one or more pharmaceutically acceptable carriers or diluents.

The pharmaceutical composition is preferably in unit dosage form, comprising from about 0.05 mg/day to about 2000 mg/day, preferably from about 0.1 mg/day to about 1000 mg/day, and more preferably from about 0.5 mg/day to about 500 mg/day of a compound according to the invention.

In another embodiment, the patient is treated with a compound according to the invention for at least about 1 week, for at least about 2 weeks, for at least about 4 weeks, for at least about 2 months or for at least about 4 months.

In yet another embodiment, the pharmaceutical composition is for oral, nasal, buccal, transdermal, pulmonal or parenteral administration.

Furthermore, the invention relates to the use of a compound according to the invention for the preparation of a pharmaceutical composition for the treatment of disorders and diseases wherein a modulation or an inhibition of the activity of 11βHSD1 is beneficial.

The invention also relates to a method for the treatment of disorders and diseases wherein a modulation or an inhibition of the activity of 11βHSD1 is beneficial, the method comprising administering to a subject in need thereof an effective amount of a compound according to the invention.

In a preferred embodiment of the invention the present compounds are used for the preparation of a medicament for the treatment of any diseases and conditions that are influenced by intracellular glucocorticoid levels as mentioned above.

Thus, in a preferred embodiment of the invention the present compounds are used for the preparation of a medicament for the treatment of conditions and disorders where a decreased level of active intracellular glucocorticoid is desirable, such as the conditions and diseases mentioned above.

In yet a preferred embodiment of the invention the present compounds are used for the preparation of a medicament for the treatment of metabolic syndrome, insulin resistance, dyslipidemia, hypertension obesity, type 2 diabetes, impaired glucose tolerance (IGT), impaired fasting glucose (IFG), progression from IGT to type 2 diabetes, progression of the metabolic syndrome into type 2 diabetes, diabetic late complications (e.g., cardiovascular diseases, arteriosclerosis, and atherosclerosis), neurodegenerative and psychiatric disorders, and, the adverse effects of glucocorticoid receptor agonist treatment or therapy.

In another embodiment of the present invention, the route of administration may be any route which effectively transports a compound according to the invention to the appropriate or desired site of action, such as oral, nasal, buccal, transdermal, pulmonal, or parenteral.

In still a further aspect of the invention the present compounds are administered in combination with one or more further active substances in any suitable ratios. Such further active substances may e.g., be selected from antiobesity agents, antidiabetics, agents modifying the lipid metabolism, antihypertensive agents, glucocorticoid receptor agonists, agents for the treatment and/or prevention of complications resulting from or associated with diabetes and agents for the treatment and/or prevention of complications and disorders resulting from or associated with obesity.

Thus, in a further aspect of the invention the present compounds may be administered in combination with one or more antiobesity agents or appetite regulating agents.

Such agents may be selected from the group consisting of CART (cocaine amphetamine regulated transcript) agonists, NPY (neuropeptide Y) antagonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, PPAR (peroxisome proliferator-activated receptor) modulators, RXR (retinoid X receptor) modulators, TR β agonists, AGRP (Agouti related protein) inhibitors, H3 histamine antagonists, opioid antagonists (such as naltrexone), exendin-4, GLP-1 and ciliary neurotrophic factor.

In one embodiment of the invention the antiobesity agent is leptin; dexamphetamine or amphetamine; fenfluramine or dexfenfluramine; sibutramine; orlistat; mazindol or phentermine.

Suitable antidiabetic agents include insulin, insulin analogues and derivatives such as those disclosed in EP 792 290 (Novo Nordisk A/S), e.g., $N^{\epsilon B29}$-tetradecanoyl des (B30) human insulin, EP 214 826 and EP 705 275 (Novo Nordisk A/S), e.g., Asp$^{B28}$ human insulin, U.S. Pat. No. 5,504,188 (Eli Lilly), e.g., Lys$^{B28}$ Pro$^{B29}$ human insulin, EP 368 187 (Aventis), eg Lantus, which are all incorporated herein by reference, GLP-1 (glucagon like peptide-1) and GLP-1 derivatives such as those disclosed in WO 98/08871 to Novo Nordisk A/S, which is incorporated herein by reference as well as orally active hypoglycaemic agents.

The orally active hypoglycaemic agents preferably comprise sulphonylureas, biguanides, meglitinides, glucosidase inhibitors, glucagon antagonists such as those disclosed in WO 99/01423 to Novo Nordisk A/S and Agouron Pharmaceuticals, Inc., GLP-1 agonists, potassium channel openers such as those disclosed in WO 97/26265 and WO 99/03861 to Novo Nordisk A/S which are incorporated herein by reference, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents and antilipidemic agents as PPARα modulators, PPARδ modulators, cholesterol absorption inhibitors, HSL (hormone-sensitive lipase) inhibitors and HMG CoA inhibitors (statins), nicotinic acid, fibrates, anion exchangers, compounds lowering food intake, bile acid resins, RXR agonists and agents acting on the ATP-dependent potassium channel of the β-cells.

In one embodiment, the present compounds are administered in combination with insulin or an insulin analogue or derivative, such as N$^{εB29}$-tetradecanoyl des (B30) human insulin, Asp$^{B28}$ human insulin, Lys$^{B28}$ Pro$^{B29}$ human insulin, Lantus®, or a mix-preparation comprising one or more of these.

In a further embodiment the present compounds are administered in combination with a sulphonylurea e.g., tolbutamide, glibenclamide, glipizide or glicazide.

In another embodiment the present compounds are administered in combination with a biguanide e.g., metformin.

In yet another embodiment the present compounds are administered in combination with a meglitinide e.g., repaglinide or senaglinide.

In still another embodiment the present compounds are administered in combination with a thiazolidinedione e.g., troglitazone, ciglitazone, pioglitazone, rosiglitazone or compounds disclosed in WO 97/41097 such as 5-[[4-[3-Methyl-4-oxo-3,4-dihydro-2-quinazolinyl]methoxy]phenyl-methyl] thiazolidine-2,4-dione or a pharmaceutically acceptable salt thereof, preferably the potassium salt.

In yet another embodiment the present compounds may be administered in combination with the insulin sensitizers disclosed in WO 99/19313 such as (−) 3-[4-[2-Phenoxazin-10-yl)ethoxy]phenyl]-2-ethoxypropanoic acid or a pharmaceutically acceptable salts thereof, preferably the arginine salt.

In a further embodiment the present compounds are administered in combination with an α-glucosidase inhibitor e.g., miglitol or acarbose.

In another embodiment the present compounds are administered in combination with an agent acting on the ATP-dependent potassium channel of the β-cells e.g., tolbutamide, glibenclamide, glipizide, glicazide or repaglinide.

Furthermore, the present compounds may be administered in combination with nateglinide.

In still another embodiment the present compounds are administered in combination with an antihyperlipidemic agent or antilipidemic agent e.g., cholestyramine, colestipol, clofibrate, gemfibrozil, fenofibrate, bezafibrate, tesaglitazar, EML-4156, LY-818, MK-767, atorvastatin, fluvastatin, lovastatin, pravastatin, simvastatin, acipimox, probucol, ezetimibe or dextrothyroxine.

In a further embodiment the present compounds are administered in combination with more than one of the above-mentioned compounds e.g., in combination with a sulphonylurea and metformin, a sulphonylurea and acarbose, repaglinide and metformin, insulin and a sulphonylurea, insulin and metformin, insulin, insulin and lovastatin, etc.

Further, the present compounds may be administered in combination with one or more antihypertensive agents. Examples of antihypertensive agents are β-blockers such as alprenolol, atenolol, timolol, pindolol, propranolol, metoprolol, bisoprololfumerate, esmolol, acebutelol, metoprolol, acebutolol, betaxolol, celiprolol, nebivolol, tertatolol, oxprenolol, amusolalul, carvedilol, labetalol, β2-receptor blockers e.g., S-atenolol, OPC-1085, ACE (angiotensin converting enzyme) inhibitors such as quinapril, lisinopril, enalapril, captopril, benazepril, perindopril, trandolapril, fosinopril, ramipril, cilazapril, delapril, imidapril, moexipril, spirapril, temocapril, zofenopril, S-5590, fasidotril, Hoechst-Marion Roussel: 100240 (EP 00481522), omapatrilat, gemopatrilat and GW-660511, calcium channel blockers such as nifedipine, felodipine, nicardipine, isradipine, nimodipine, diltiazem, amlodipine, nitrendipine, verapamil, lacidipine, lercanidipine, aranidipine, cilnidipine, clevidipine, azelnidipine, barnidipine, efonodipine, iasidipine, iemildipine, iercanidipine, manidipine, nilvadipine, pranidipine, furnidipine, α-blockers such as doxazosin, urapidil, prazosin, terazosin, bunazosin and OPC-28326, diuretics such as thiazides/sulphonamides (e.g., bendroflumetazide, chlorothalidone, hydrochlorothiazide and clopamide), loop-diuretics (e.g., bumetanide, furosemide and torasemide) and potassium sparing diuretics (e.g., amiloride, spironolactone), endothelin ET-A antagonists such as ABT-546, ambrisetan, atrasentan, SB-234551, CI-1034, S-0139 and YM-598, endothelin antagonists e.g., bosentan and J-104133, renin inhibitors such as aliskiren, vasopressin V1 antagonists e.g., OPC-21268, vasopressin V2 antagonists such as tolvaptan, SR-121463 and OPC-31260, B-type natriuretic peptide agonists e.g., Nesiritide, angiotensin II antagonists such as irbesartan, candesartancilexetil, losartan, valsartan, telmisartan, eprosartan, candesartan, CL-329167, eprosartan, iosartan, olmesartan, pratosartan, TA-606, and YM-358, 5-HT2 agonists e.g., fenoldopam and ketanserin, adenosine A1 antagonists such as naftopidil, N-0861 and FK-352, thromboxane A2 antagonists such as KT2-962, endopeptidase inhibitors e.g., ecadotril, nitric oxide agonists such as LP-805, dopamine D1 antagonists e.g., MYD-37, dopamine D2 agonists such as nolomirole, n-3 fatty acids e.g., omacor, prostacyclin agonists such as treprostinil, beraprost, PGE1 agonists e.g., ecraprost, Na+/K+ATPase modulators e.g., PST-2238, Potassium channel activators e.g., KR-30450, vaccines such as PMD-3117, Indapamides, CGRP-unigene, guanylate cyclase stimulators, hydralazines, methyldopa, docarpamine, moxonidine, CoAprovel, MondoBiotech-811.

Further reference can be made to Remington: The Science and Practice of Pharmacy, 19$^{th}$ Edition, Gennaro, Ed., Mack Publishing Co., Easton, Pa., 1995.

Furthermore, the present compounds may be administered in combination with one or more glucocorticoid receptor agonists. Examples of such glucocorticoid receptor agonists are betametasone, dexamethasone, hydrocortisone, methylprednisolone, prednisolone, prednisone, beclomethasone, butixicort, clobetasol, flunisolide, flucatisone (and analogues), mometasone, triamcinolonacetonide, triamcinolonhexacetonide GW-685698, NXC-1015, NXC-1020, NXC-1021, NS-126, P-4112, P-4114, RU-24858 and T-25 series.

It should be understood that any suitable combination of the compounds according to the invention with one or more of the above-mentioned compounds and optionally one or more further pharmacologically active substances are considered to be within the scope of the present invention.

Pharmaceutical Compositions

The compounds of the present invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as hard or soft capsules, tablets, troches, dragees, pills, lozenges, powders and granules. Where appropriate, they can be prepared with coatings such as enteric coatings or they can be formulated so as to provide controlled release of the active ingredient such as sustained or prolonged release according to methods well-known in the art.

Liquid dosage forms for oral administration include solutions, emulsions, suspensions, syrups and elixirs.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. Depot injectable formulations are also contemplated as being within the scope of the present invention.

Other suitable administration forms include suppositories, sprays, ointments, crèmes, gels, inhalants, dermal patches, implants etc.

A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain from 0.05 to about 2000 mg, e.g., from about 0.1 to about 1000 mg, from about 0.5 mg to about 500 mg., from about 1 mg to about 200 mg, e.g., about 100 mg.

For parenteral routes, such as intravenous, intrathecal, intramuscular and similar administration, typically doses are in the order of about half the dose employed for oral administration.

The compounds of this invention are generally utilized as the free substance or as a pharmaceutically acceptable salt thereof. Examples are an acid addition salt of a compound having the utility of a free base and a base addition salt of a compound having the utility of a free acid. The term "pharmaceutically acceptable salts" refers to non-toxic salts of the compounds for use according to the present invention which are generally prepared by reacting the free base with a suitable organic or inorganic acid or by reacting the acid with a suitable organic or inorganic base. When a compound for use according to the present invention, contains a free base such salts are prepared in a conventional manner by treating a solution or suspension of the compound with a chemical equivalent of a pharmaceutically acceptable acid. When a compounds for use according to the present invention, contains a free acid such salts are prepared in a conventional manner by treating a solution or suspension of the compound with a chemical equivalent of a pharmaceutically acceptable base. Physiologically acceptable salts of a compound with a hydroxy group include the anion of said compound in combination with a suitable cation such as sodium or ammonium ion. Other salts which are not pharmaceutically acceptable may be useful in the preparation of compounds for use according to the present invention and these form a further aspect of the present invention.

For parenteral administration, solutions of the present compounds in sterile aqueous solution, aqueous propylene glycol or sesame or peanut oil may be employed. Such aqueous solutions should be suitable buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of suitable carriers are water, salt solutions, alcohols, polyethylene glycols, polyhydroxyethoxylated castor oil, peanut oil, olive oil, syrup, phospholipids, gelatine, lactose, terra alba, sucrose, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavouring agents.

The pharmaceutical compositions formed by combining the compounds of the invention and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable excipient. These formulations may be in the form of powder or granules, as a solution or suspension in an aqueous or non-aqueous liquid, or as an oil-in-water or water-in-oil liquid emulsion.

Compositions intended for oral use may be prepared according to any known method, and such compositions may contain one or more agents selected from the group consisting of sweetening agents, flavouring agents, colouring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatine or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and 4,265,874, incorporated herein by reference, to form osmotic therapeutic tablets for controlled release.

Formulations for oral use may also be presented as hard gelatine capsules where the active ingredient is mixed with an inert solid diluent, for example, calcium carbonate, calcium phosphate or kaolin, or a soft gelatine capsule wherein the active ingredient is mixed with water or an oil medium, for example peanut oil, liquid paraffin, or olive oil.

Aqueous suspensions may contain the active compounds in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavouring, and colouring agents may also be present.

The pharmaceutical compositions comprising a compound for use according to the present invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, preservative and flavouring and colouring agent. The pharmaceutical compositions may be in the form of a sterile injectable aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The compositions may also be in the form of suppositories for rectal administration of the compounds of the present invention. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example.

For topical use, creams, ointments, jellies, solutions of suspensions, etc., containing the compounds of the present invention are contemplated. For the purpose of this application, topical applications shall include mouth washes and gargles.

The compounds for use according to the present invention may also be administered in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines.

In addition, some of the compounds for use according to the present invention may form solvates with water or common organic solvents. Such solvates are also encompassed within the scope of the present invention.

Thus, in a further embodiment, there is provided a pharmaceutical composition comprising a compound for use according to the present invention, or a pharmaceutically acceptable salt, solvate, or prodrug thereof, and one or more pharmaceutically acceptable carriers, excipients, or diluents.

If a solid carrier is used for oral administration, the preparation may be tabletted, placed in a hard gelatine capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

A typical tablet which may be prepared by conventional tabletting techniques may contain:

| Core: | |
|---|---|
| Active compound (as free compound or salt thereof) | 5.0 mg |
| Lactosum PH. Eur. | 67.8 mg |
| Cellulose, microcryst. (Avicel) | 31.4 mg |
| Amberlite ®IRP88* | 1.0 mg |
| Magnesii stearas PH. Eur. | q.s. |
| Coating: | |
| Hydroxypropyl methylcellulose | approx. 9 mg |
| Mywacett 9-40 T** | approx. 0.9 mg |

Polacrillin potassium NF, tablet disintegrant, Rohm and Haas.
**Acylated monoglyceride used as plasticizer for film coating.

The compounds of the invention may be administered to a patient which is a mammal, especially a human in need thereof. Such mammals include also animals, both domestic animals, e.g., household pets, and non-domestic animals such as wildlife.

Any novel feature or combination of features described herein is considered essential to this invention.

The present invention also relate to the below methods of preparing the compounds of the invention.

The present invention is further illustrated in the following representative examples which are, however, not intended to limit the scope of the invention in any way.

EXAMPLES

The following examples and general procedures refer to intermediate compounds and final products for general formula (I) identified above. The preparation of the compounds of general formula (I) of the present invention is described in detail using the following examples. Occasionally, the reaction may not be applicable as described to each compound included within the disclosed scope of the invention. The compounds for which this occurs will be readily recognised by those skilled in the art. In these cases the reactions can be successfully performed by conventional modifications known to those skilled in the art, which is, by appropriate protection of interfering groups, by changing to other conventional reagents, or by routine modification of reaction conditions. Alternatively, other reactions disclosed herein or otherwise conventional will be applicable to the preparation of the corresponding compounds of the invention. In all preparative methods, all starting materials are known or may easily be prepared from known starting materials. The structures of the compounds are confirmed by either elemental analysis or nuclear magnetic resonance (NMR), where peaks assigned to characteristic protons in the title compounds are presented where appropriate. $^1$H NMR shifts ($\delta_H$) are given in parts per million (ppm) down field from tetramethylsilane as internal reference standard. M.p.: is melting point and is given in ° C. and is not corrected. Column chromatography was carried out using the technique described by W. C. Still et al., *J. Org. Chem.* 43:2923 (1978) on Merck silica gel 60 (Art. 9385). HPLC analyses are performed using 5 μm C18 4×250 mm column eluted with various mixtures of water and acetonitrile, flow=1 ml/min, as described in the experimental section.

Microwave oven synthesis: The reaction was heated by microwave irradiation in sealed microwave vessels in a single mode Emrys Optimizer EXP from PersonalChemistry®.

Preparative HPLC: Column: 1.9×15 cm Waters XTerra RP-18. Buffer: linear gradient 5-95% in 15 min, MeCN, 0.1% TFA, flow rate of 15 ml/min. The pooled fractions are either evaporated to dryness in vacuo, or evaporated in vacuo until the MeCN is removed, and then frozen and freeze dried.

Abbreviations
d=day(s)
g=gram(s)
h=hour(s)
Hz=hertz
L=liter(s)
M=molar
mg=milligram(s)
min=minute(s)
mL=milliliter(s)
mmol=millimole(s)
mol=mole(s)
ppm=parts per million
psi=pounds per square inch
ESI=electrospray ionization
m/z=mass to charge ratio
mp=melting point
MS=mass spectrometry
HPLC=high pressure liquid chromatography
RP=reverse phase
HPLC-MS=high pressure liquid chromatography-mass spectrometry
NMR=nuclear magnetic resonance spectroscopy
rt=room temperature
TLC=thin layer chromatography
DCM=dichloromethane, $CH_2Cl_2$, methylenechloride
DIPEA=N,N-diisopropylethylamine
DMF=N,N-dimethylformamide
DMSO=dimethylsulfoxide
EDAC=1-ethyl-3-(3-dimethylaminopropyl)carbodiimide hydrochloride
$Et_2O$=diethyl ether
EtOAc=ethyl acetate
HOBt=1-hydroxybenzotriazole
MeCN=acetonitrile
MeOH=methanol
NMP=N-methylpyrrolidin-2-one
TEA=triethylamine
TFA=trifluoroacetic acid
THF=tetrahydrofuran
$CDCl_3$=deuterio chloroform
$CD_3OD$=tetradeuterio methanol
DMSO-$d_6$=hexadeuterio dimethylsulfoxide Analysis
NMR NMR spectra were recorded at 300 and 400 MHz on a Bruker DRX300, DRX400 or AV400 instrument equipped with 5 mm selective-inverse (SEI, $^1$H and $^{13}$C), 5 mm broadband inverse (BBI, $^1$H, broad-band) and 5 mm quadro nuclear (QNP, $^1$H, $^{13}$C) probeheads, respectively. Shifts (δ) are given in parts per million (ppm) down field from tetramethylsilane as internal reference standard.

HPLC-MS
HPLC-MS Method

The RP-analysis was performed on an Agilent HPLC system (1100 degasser, 1100 pump, 1100 injector and a 1100 DAD) fitted with an Agilent MS detector system Model VL (MW 0-1000) and a S.E.D.E.R.E Model Sedex 55 ELS detector system using a Waters X-terra MS C18 column (5 μm, 3.0 mm×50 mm) with gradient elution, 5% to 95% solvent B (0.05% TFA in acetonitrile) in solvent A (0.05% TFA in water) within 3 min, 2.7 mL/min, temperature 40° C.

Preparative Techniques
HPLC
HPLC Method Z3

The $R^P$-purification was performed on a Gilson system (3 Gilson 306 pumps, Gilson 170 DAD detector and a Gilson 215 liquid handler) using a Waters X-terra $R^P$ (10 μm, 30 mm×150 mm) with gradient elution, 5% to 95% solvent B (0.05% TFA in acetonitrile) in solvent A (0.05% TFA in water) within 15 min, 40 mL/min, detection at 210 nm, temperature rt. The pooled fractions are either evaporated to dryness in vacuo, or evaporated in vacuo until the acetonitrile is removed, and then frozen and freeze dried.

General

The following examples and general procedures refer to intermediate compounds and final products for general formula (I) identified in the specification and in the synthesis schemes. The preparation of the compounds of general formula (I) of the present invention is described in detail using the following examples. Occasionally, the reaction may not be applicable as described to each compound included within the disclosed scope of the invention. The compounds for which this occurs will be readily recognised by those skilled in the art. In these cases the reactions can be successfully performed by conventional modifications known to those skilled in the art, which is, by appropriate protection of interfering groups, by changing to other conventional reagents, or by routine modification of reaction conditions. Alternatively, other reactions disclosed herein or otherwise conventional will be applicable to the preparation of the corresponding compounds of the invention. In all preparative methods, all starting materials are known or may be prepared by a person skilled in the art in analogy with the preparation of similar known compounds or by the General procedures A through D described herein. The structures of the compounds are confirmed by either elemental analysis or nuclear magnetic resonance (NMR), where peaks assigned to characteristic protons in the title compounds are presented where appropriate.

General Procedures

General Procedure (A)

Compounds of the formula (Ia) according to the invention wherein $R^1$, $R^3$, and $R^4$ are as defined for formula (I), with $NR^3R^4$ corresponding to ring A, can be prepared as outlined below:

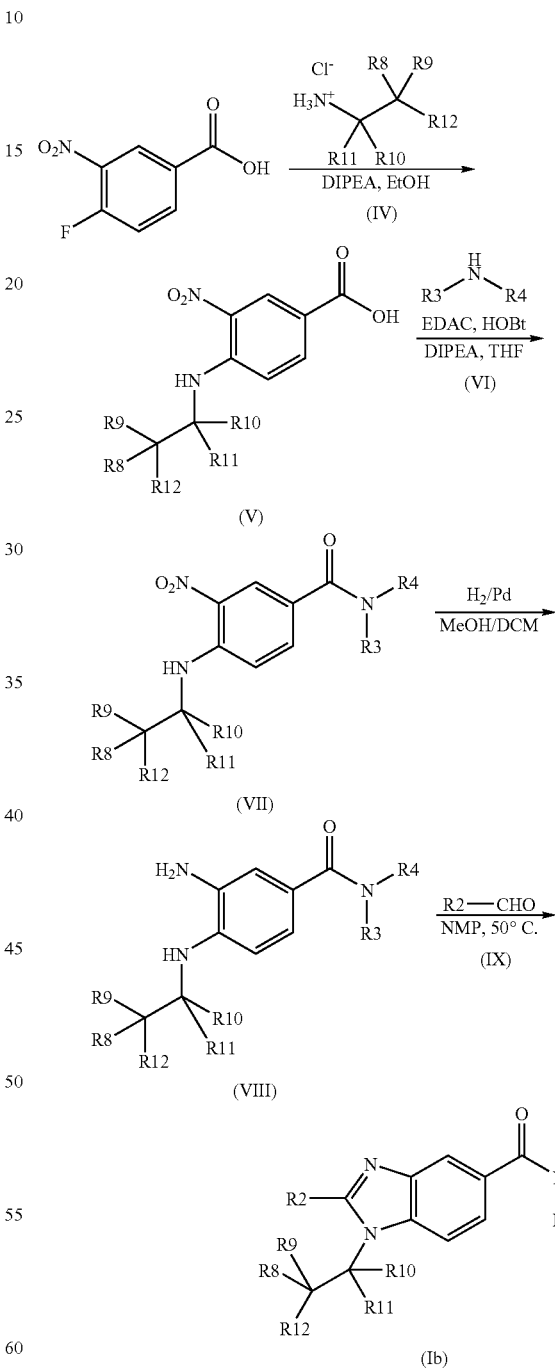

and HOBt) or an activated carboxylic acid of the formula (III) wherein $R^1$ is as defined above. This reaction may be carried out in a suitable solvent (e.g., dichloromethane) in the presence of a base (e.g., DIPEA) at ambient temperature.

General Procedure (B)

Compounds of the formula (Ib) according to the invention wherein $R^2$, $R^3$, $R^4$, $R^8$, $R^9$, $R^{10}$, $R^{11}$, and $R^{12}$ are as defined for formula (I), with $NR^3R^4$ corresponding to ring A, can be prepared as outlined below:

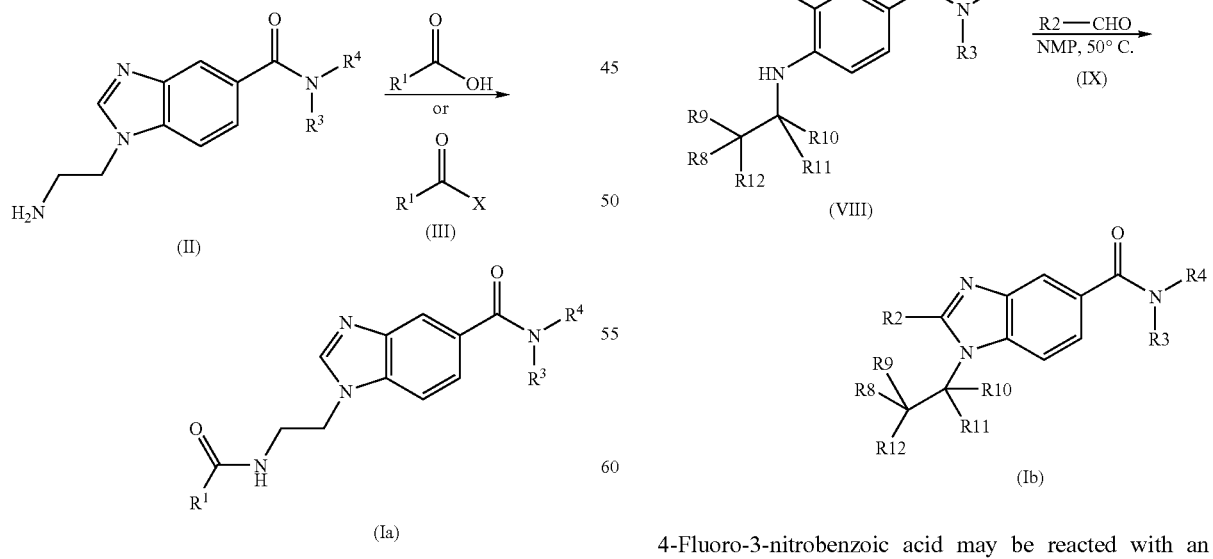

4-Fluoro-3-nitrobenzoic acid may be reacted with an amine of formula (IV) wherein $R^8$, $R^9$, $R^{10}$, $R^{11}$ and $R^{12}$ are as defined above. This reaction may be carried out in a suitable solvent (e.g., ethanol) in the presence of a base (e.g., DIPEA) at ambient temperature forming the secondary aniline of for- A benzimidazole of formula (II) wherein $NR^3R^4$ corresponds to ring A defined above may be reacted with a carboxylic acid in the presence of coupling reagents (e.g., EDAC mula (V). The carboxylic acid of formula (V) then can be activated with HOBT and EDAC and reacted with an amine of the formula (VI) wherein $NR^3R^4$ is ring A as defined above. This reaction may be carried out in a suitable solvent (e.g., THF) in the presence of a base (e.g., DIPEA) at ambient temperature forming the compound of formula (VII). The nitro group of compounds of formula (VII) may be reduced by hydrogen under pressure in a suitable solvent (e.g., methanol/dichloromethane) in presence of a catalyst (e.g., palladium on activated carbon) at ambient temperature to form the diamine of formula (VIII). Compounds of formula (VIII) may be reacted with an aldehyde of formula (IX) wherein $R^2$ is as defined above. This reaction may be carried out in a suitable solvent (e.g., NMP) in the presence of a drying agent (e.g., molecular sieve 4 Å) at 50° C. to form compounds of formula (Ib).

General Procedure (C)

Compounds of the formula (Ic) according to the invention wherein $R^2$, $R^3$, and $R^4$ are as defined for formula (I), with $NR^3R^4$ corresponding to ring A, can be prepared as outlined below:

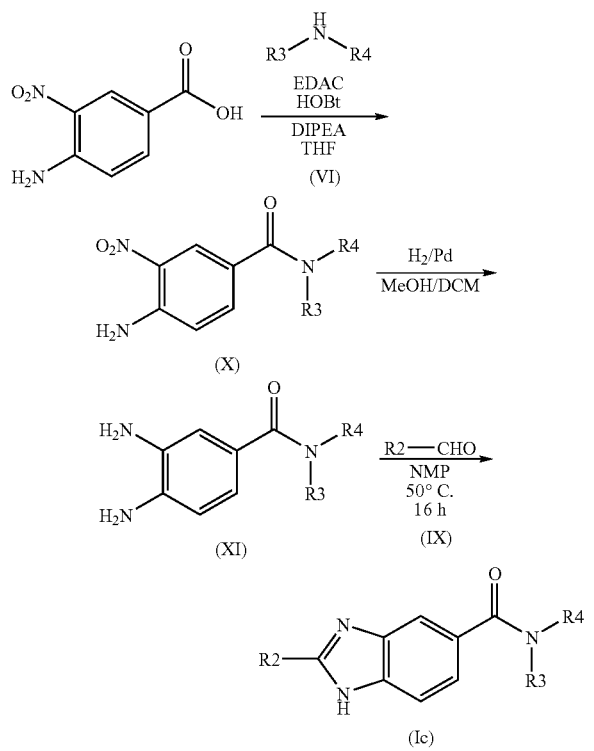

4-Amino-3-nitrobenzoic acid can be activated with HOBT and EDAC and reacted with an amine of the formula (VI) wherein $NR^3R^4$ is ring A as defined above. This reaction may be carried out in a suitable solvent (e.g., THF) in the presence of a base (e.g., DIPEA) at ambient temperature to form the compound of formula (X). The nitro group of the formula (X) may be reduced by hydrogen under pressure in a mixture of methanol and dichloromethane in presence of a catalyst (e.g., palladium on activated carbon) at ambient temperature to form the diamine of the formula (XI). (XI) may be reacted with an aldehyde of the formula (IX) wherein $R^2$ is as defined above. This reaction may be carried out in NMP in the presence of a drying agent (e.g., molecular sieve 4 Å) at 50° C. to form target product (Ic).

General Procedure (D)

Compounds of the formula (Id) according to the invention wherein $R^1$, $R^3$, $R^4$, and $R^5$ are as defined for formula (I), with $NR^3R^4$ corresponding to ring A, can be prepared as outlined below:

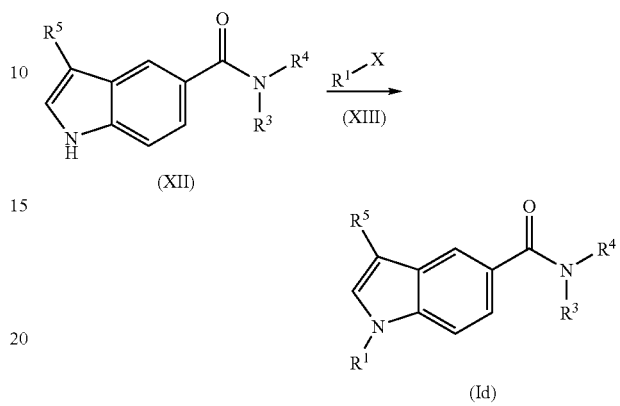

An indole of formula (XII) wherein $R^3$, $R^4$, and $R^5$ are as defined above, with $NR^3R^4$ corresponding to ring A, may be reacted with an alky/benzyl halide of the formula (XIII) wherein $R^1$ is as defined above in the presence of base (e.g., sodium hydride). This reaction may be carried out in a suitable solvent (e.g., DMF) at a temperature of up to reflux.

Example 1

General Procedure (A)

Furan-2-carboxylic acid {2-[5-(1,3,3-trimethyl-6-aza-bicyclo[3.2.1]octane-6-carbonyl)benzoimidazol-1-yl]-ethyl}-amide

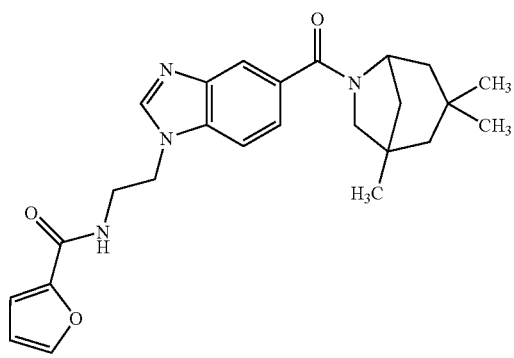

To a solution of 2-furoic acid (37 mg, 0.33 mmol) in dry THF (2 mL) at room temperature under an inert atmosphere of nitrogen were added HOBt (49 mg, 0.36 mmol) and EDAC (82 mg, 0.43 mmol), and the resulting solution was stirred for 30 min. [1-(2-Aminoethyl)-1H-benzoimidazol-5-yl]-(1,3,3-trimethyl-6-aza-bicyclo[3.2.1]oct-6-yl)-methanone trifluoroacetate (150 mg, 0.33 mmol) was added to the solution followed by TEA (0.184 mL, 1.32 mmol), and the reaction mixture was stirred for 16 h at room temperature. The volatiles were evaporated in vacuo and the resulting solid was purified by preparative HPLC, dried in vacuo at 50° C. affording 100 mg (70%) of the title compound as a solid. MS-ESI m/z 435; $^1$H NMR (400 MHz, DMSO-d$_6$) δ 0.88-0.99 (m, 6H), 1.07 (d, 3H), 1.29-1.41 (m, 4H), 1.50-1.52 (m) and 2.10-2.11 (m, 1H), 1.76-1.79 (m, 1H), 3.02 (d), 3.13 (d), 3.32 (d) and 3.47 (d, 2H), 3.69 (t, 2H), 3.87-3.89 (m) and 4.39-4.41 (m, 1H), 4.56 (t, 2H), 6.58 (s, 1H), 6.98 (d, 1H), 7.48 (dd, 1H), 7.77-7.82 (m, 2H), 7.89 (t, 1H), 8.54-8.58 (m, 1H), 9.07 (d, 1H).

The following compounds were synthesised employing a similar method to the one described in Example 1 above:

| Ex. | Structure | MW | IUPAC Name | MS-ESI m/z |
|---|---|---|---|---|
| 1-1 | 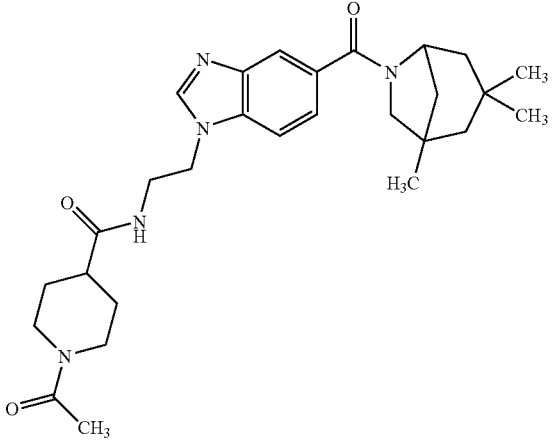 | 493.65 | 1-Acetyl-piperidine-4-carboxylic acid {2-[5-(1,3,3-trimethyl-6-aza-bicyclo-[3.2.1]octane-6-carbonyl)-benzoimidazol-1-yl]-ethyl}-amide | 494 |
| 1-2 | 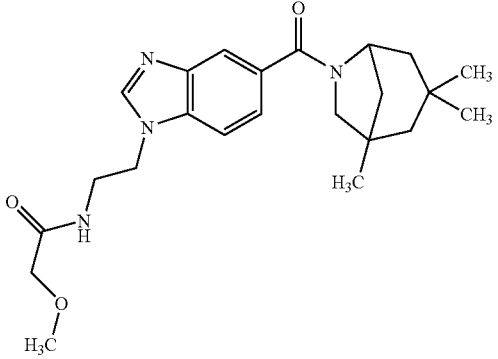 | 412.53 | 2-Methoxy-N-{2-[5-(1,3,3-trimethyl-6-aza-bicyclo-[3.2.1]octane-6-carbonyl)-benzoimidazol-1-yl]-ethyl}-acetamide | 413 |
| 1-3 | 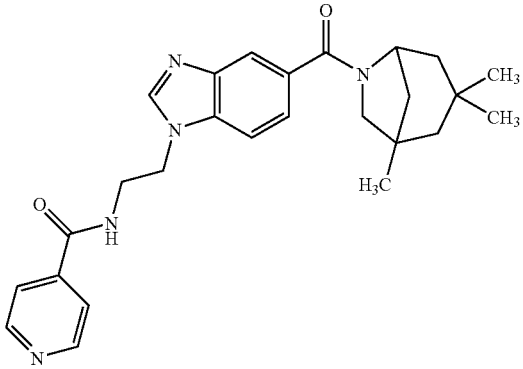 | 445.57 | N-{2-[5-(1,3,3-Trimethyl-6-aza-bicyclo[3.2.1]octane-6-carbonyl)-benzoimidazol-1-yl]-ethyl}-isonicotinamide | 446 |

-continued

| Ex. | Structure | MW | IUPAC Name | MS-ESI m/z |
|---|---|---|---|---|
| 1-4 | 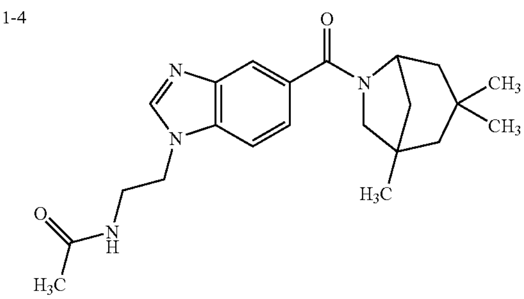 | 382.51 | N-{2-[5-(1,3,3-Trimethyl-6-aza-bicyclo[3.2.1]octane-6-carbonyl)-benzoimidazol-1-yl]-ethyl}-acetamide | 383 |
| 1-5 | 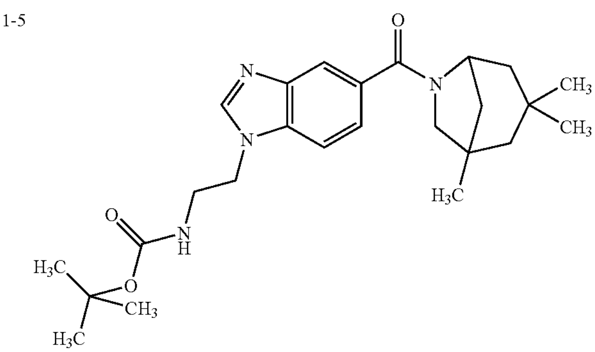 | 440.59 | {2-[5-(1,3,3-Trimethyl-6-aza-bicyclo[3.2.1]octane-6-carbonyl)-benzoimidazol-1-yl]-ethyl}-carbamic acid tert-butyl ester | 441 |
| 1-6 | 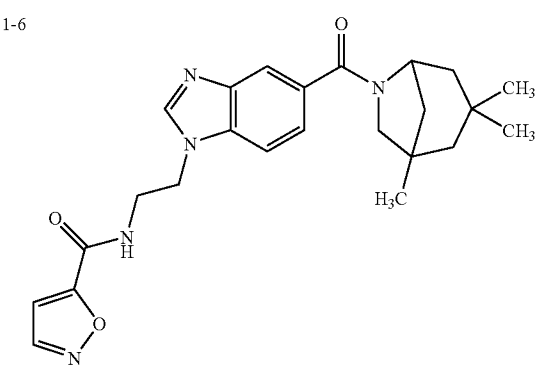 | 435.53 | Isoxazole-5-carboxylic acid {2-[5-(1,3,3-trimethyl-6-aza-bicyclo[3.2.1]octane-6-carbonyl)-benzoimidazol-1-yl]-ethyl}-amide | 436 |
| 1-7 | 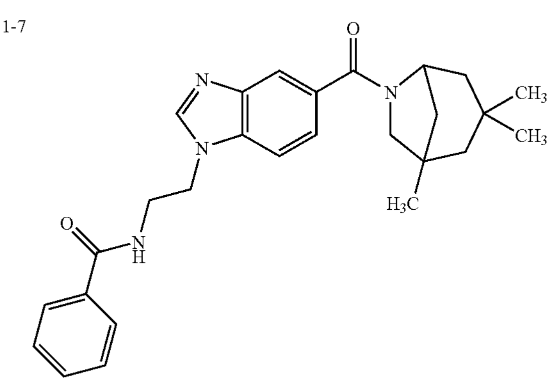 | 444.58 | N-{2-[5-(1,3,3-Trimethyl-6-aza-bicyclo[3.2.1]octane-6-carbonyl)-benzoimidazol-1-yl]-ethyl}-benzamide | 445 |

Example 2

General Procedure (B)

3-[2-Ethyl-5-(1,3,3-trimethyl-6-aza-bicyclo[3.2.1]octane-6-carbonyl)-benzimidazol-1-yl]-propionic Acid Ethyl Ester

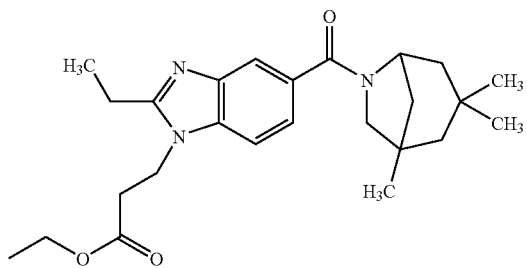

To a solution of 3-[2-amino-4-(1,3,3-trimethyl-6-aza-bicyclo[3.2.1]octane-6-carbonyl)-phenylamino]-propionic acid ethyl ester (250 mg, 0.645 mmol) in dry NMP (10 mL) at room temperature under an inert atmosphere of nitrogen was added approx. 200 mg of molecular sieve 4 Å followed by acetaldehyde (93 uL, 1.29 mmol). The mixture was stirred for 16 hrs at 50° C. The reaction was quenched by the addition of water (100 mL) followed by extraction with diethyl ether (3×100 mL). The combined organic phases were washed with brine (4×200 mL), dried (MgSO$_4$), filtered, and evaporated in vacuo. The resulting oil was purified by preparative HPLC, dried in vacuo at 50° C. affording 104 mg (38%) of the title compound as brown oil. MS-ESI m/z 426; $^1$H NMR (400 MHz, CDCl3) δ 0.88-1.06 (m, 6H), 1.11-1.23 (m, 7H), 1.24-1.28 (m) and 1.55-1.65 (m, 1H), 1.36-1.45 (m, 2H), 1.50 (t, 3H), 1.74-1.81 (m, 1H), 2.23-2.30 (m) and 3.12-3.20 (m, 1H), 2.81 (t, 2H), 2.96 (q, 2H), 3.22-3.35 (m, 1H), 3.32 (dd) and 3.62 (dd, 1H), 4.03-4.07 (m) and 4.63-4.67 (m, 1H), 4.13 (q, 2H), 4.45 (dt, 2H), 7.32-7.46 (m, 2H), 7.84 (d, 1H).

Example 3

3-[2-Ethyl-5-(1,3,3-trimethyl-6-aza-bicyclo[3.2.1]octane-6-carbonyl)-benzimidazol-1-yl]-propionic Acid

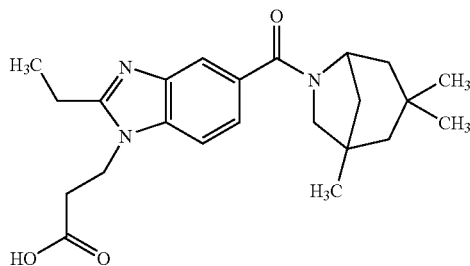

To a solution of 3-[2-ethyl-5-(1,3,3-trimethyl-6-aza-bicyclo[3.2.1]octane-6-carbonyl)benzimidazol-1-yl]-propionic acid ethyl ester (104 mg, 0.244 mmol) in 96% ethanol (5 mL) at room temperature under an inert atmosphere of nitrogen was added 1N NaOH (aq) (0.3 mL, 0.3 mmol). The mixture was stirred for 2 hrs at room temperature. The reaction was quenched by the addition of water (5 mL) and acidified to pH 2 with 1N HCl followed by extraction with diethyl ether (2×10 mL). The combined organic phases were washed with water (2×10 mL), brine (10 mL), dried (MgSO$_4$), filtered, and evaporated in vacuo affording 11 mg (11%) of the title compound as yellow oil. MS-ESI m/z 398; $^1$H NMR (400 MHz, CDCl3) δ 0.83-1.06 (m, 6H), 1.12-1.22 (m, 7H), 1.24-1.28 (m) and 1.46-1.54 (m, 1H), 1.30-1.39 (m, 2H), 1.33 (t, 3H), 1.63-1.74 (m, 1H), 2.22-2.32 (m) and 3.15-3.27 (m, 1H), 2.26 (t, 2H), 2.85 (t, 2H), 3.51 (q, 2H), 7.25-7.35 (m, 2H), 7.56 (d) and 7.74 (d, 1H).

Example 4

General Procedure (C)

2-[5-(1,3,3-Trimethyl-6-aza-bicyclo[3.2.1]octane-6-carbonyl)-1H-benzimidazol-2-yl]-cyclopropanecarboxylic Acid Ethyl Ester

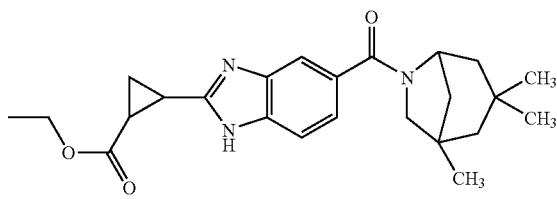

To a solution of (3,4-diaminophenyl)-(1,3,3-trimethyl-6-azabicyclo[3.2.1]oct-6-yl)methanone (500 mg, 1.74 mmol) in dry NMP (25 mL) at room temperature under an inert atmosphere of nitrogen was added approx. 500 mg of molecular sieve 4 Å followed by ethyl 2-formyl-1-cyclopropanecarboxylate (0.51 mL, 3.86 mmol). The mixture was stirred for 16 hrs at 50° C. The reaction was quenched by the addition of water (100 mL) followed by extraction with diethyl ether (3×100 mL). The combined organic phases were washed with water (3×100 mL), brine (100 mL), dried (MgSO$_4$), filtered, and evaporated in vacuo. The resulting oil was purified by preparative HPLC, dried in vacuo at 50° C. affording 60 mg (8%) of the title compound as a solid. MS-ESI m/z 410; $^1$H NMR (400 MHz, CDCl3) δ 0.88-1.06 (m, 6H), 1.07-1.20 (m, 4H), 1.25 (t, 3H), 1.27-1.34 (m) and 1.49-1.66 (m, 3H), 1.36-1.48 (m, 2H), 1.72-1.84 (m, 2H), 2.36-2.48 (m, 1H), 2.66-2.76 (m, 1H), 3.18-3.27 (m, 1H), 3.30 (d) and 3.65 (d, 1H), 4.00-4.06 (m) and 4.57-4.65 (m, 1H), 4.14 (q, 2H), 7.18-7.30 (m, 2H), 7.57 (d, 1H), 10.37 (br s, 1H).

Example 5

2-[5-(1,3,3-Trimethyl-6-aza-bicyclo[3.2.1]octane-6-carbonyl)-1H-benzimidazol-2-yl]-cyclopropanecarboxylic Acid

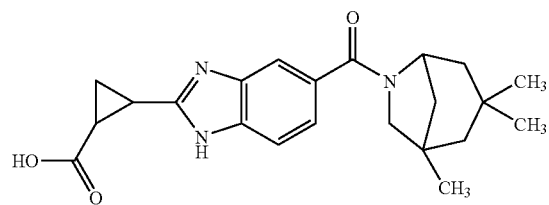

To a solution of 2-[5-(1,3,3-trimethyl-6-aza-bicyclo[3.2.1]octane-6-carbonyl)-1H-benzimidazol-2-yl]-cyclopropanecarboxylic acid ethyl ester (60 mg, 0.147 mmol) in 96% ethanol (3 mL) at room temperature under an inert atmosphere of nitrogen was added 1N NaOH (aq) (0.36 mL, 0.36 mmol). The mixture was stirred for 16 hrs at 50° C. The reaction was quenched by the addition of water (3 mL) and acidified to pH 2 with 1N HCl followed by extraction with diethyl ether (2×5 mL). The combined organic phases were washed with water (2×5 mL), brine (5 mL), dried (MgSO$_4$), filtered, and evaporated in vacuo affording 49 mg (88%) of the title compound as a solid. MS-ESI m/z 382; $^1$H NMR (400 MHz, CDCl3) δ 0.87-1.06 (m, 6H), 1.08-1.20 (m, 4H), 1.30-1.38 (m, 1H), 1.39-1.45 (m) and 1.48-1.64 (m, 3H), 1.70-1.90 (m, 2H), 1.91-2.01 (m, 1H), 2.18-2.30 (m) and 2.43-2.61 (m) and 2.85-3.02 (m, 2H), 3.15 (t) and 3.66 (t, 1H), 3.20-3.34 (m, 1H), 3.88-4.01 (m) and 4.54-4.65 (m, 1H), 7.39-7.50 (m, 1H), 7.69-7.85 (m, 2H).

The following compounds were synthesised employing a similar method to the ones described in Examples 2, 3, 4 and 5 above:

| Ex. | Structure | MW | IUPAC Name | MS-ESI m/z |
|---|---|---|---|---|
| 5-1 | 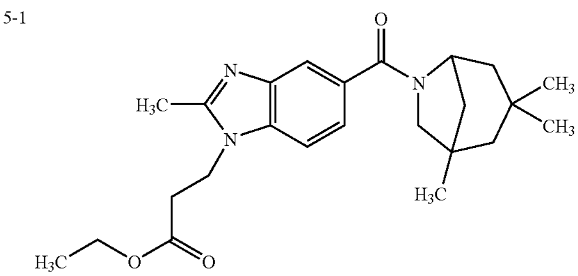 | 411.54 | 3-[2-Methyl-5-(1,3,3-trimethyl-6-aza-bicyclo[3.2.1]octane-6-carbonyl)-benzimidazol-1-yl]-propionic acid ethyl ester | 412 |
| 5-2 | 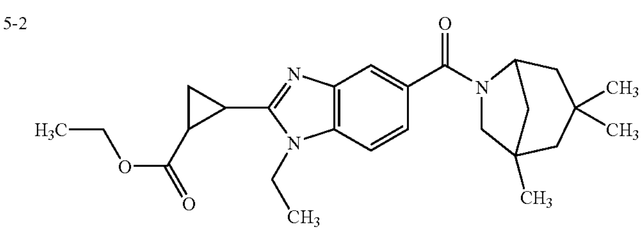 | 437.58 | 2-[1-Ethyl-5-(1,3,3-trimethyl-6-aza-bicyclo-[3.2.1]octane-6-carbonyl)-1H-benzimidazol-2-yl]-cyclopropanecarboxylic acid ethyl ester | 438 |
| 5-3 | 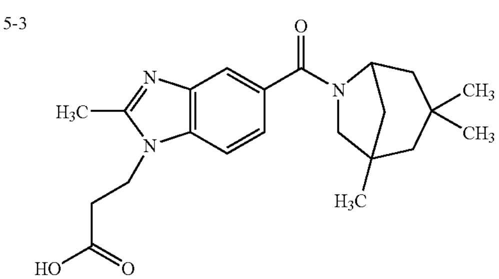 | 383.49 | 3-[2-Methyl-5-(1,3,3-trimethyl-6-aza-bicyclo-[3.2.1]octane-6-carbonyl)-benzimidazol-1-yl]-propionic acid | 384 |
| 5-4 | 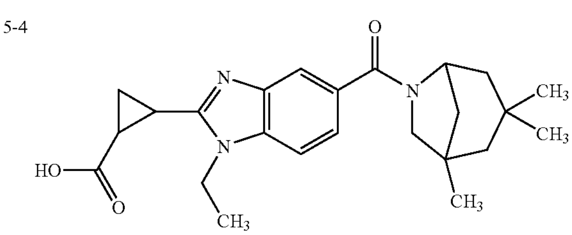 | 409.53 | 2-[1-Ethyl-5-(1,3,3-trimethyl-6-aza-bicyclo-[3.2.1]octane-6-carbonyl)-1H-benzimidazol-2-yl]-cyclopropanecarboxylic acid | 410 |

Example 6

General Procedure (D)

3-[5-(1,3,3-Trimethyl-6-aza-bicyclo[3.2.1]octane-6-carbonyl)-indol-1-yl]-propionic Acid Ethyl Ester

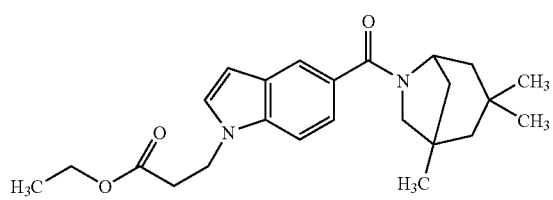

To a solution of (1H-indol-5-yl)-(1,3,3-trimethyl-6-aza-bicyclo[3.2.1]oct-6-yl)methanone (250 mg, 0.84 mmol) in dry DMF (5 mL) at room temperature under an inert atmosphere of nitrogen was added sodium hydride (30 mg, 1.26 mmol, 60% dispersion in oil), and after stirring for 30 min ethyl bromopropionate (168 mg, 0.93 mmol) was added, and the reaction mixture was stirred for 16 h at 60° C. The reaction was quenched by the addition of water (20 mL) followed by extraction with DCM (3×100 mL). The combined organic phases were dried (MgSO$_4$), filtered and evaporated in vacuo. The resulting solid was purified by silica gel chromatography using a mixture of ethyl acetate and heptane (1:1) as eluent. Pure fractions were collected, the solvent evaporated in vacuo and dried in vacuo at 50° C. affording 125 mg (37%) of the title compound as a solid. MS-ESI m/z 397; $^1$H NMR (400 MHz, CDCl$_3$) δ 0.95 (d, 3H), 1.03 (d, 3H), 1.13-1.22 (m, 7H), 1.25-1.43 (m, 2H), 1.45 (s, 1H), 1.62-1.68 (m, 1H), 1.76-1.80 (m, 1H), 2.29-2.33 (m, 1H), 2.82 (t, 2H), 3.28-3.35 (m) and 3.63 (d, 1H), 4.12-4.14 and 4.64-4.66 (m, 1H), 4.11 (q, 2H), 4.47 (t, 2H), 6.52 (d, 1H), 7.18 (d, 1H), 7.32-7.39 (m, 2H), 7.74 (d, 1H).

Example 7

3-[5-(1,3,3-Trimethyl-6-aza-bicyclo[3.2.1]octane-6-carbonyl)-indol-1-yl]-propionic Acid

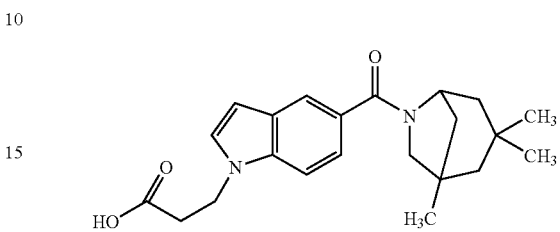

To a solution of 3-[5-(1,3,3-trimethyl-6-aza-bicyclo[3.2.1]octane-6-carbonyl)-indol-1-yl]-propionic acid ethyl ester (80 mg, 0.2 mmol) in ethanol (2 mL) was added 1N aqueous sodium hydroxide solution (2 mL), and the resulting solution stirred for 2 h. The solution was acidified with 1N hydrochloric acid solution before the organic volatiles were removed in vacuo, and the aqueous residues were extracted with DCM (3×5 mL). The combined organic phases were dried (MgSO$_4$), filtered, and evaporated in vacuo. The resulting solid was purified by preparative HPLC, dried in vacuo at 50° C. affording 55 mg (74%) of the title compound as a solid. MS-ESI m/z 369; $^1$H NMR (400 MHz, DMSO-d$_6$) δ 0.94 (d, 3H), 1.04 (d, 3H), 1.13-1.17 (m, 4H), 1.28-1.38 (m, 2H), 1.43-1.45 (m, 1H), 1.60-1.63 (m, 1H), 1.75-1.79 (m, 1H), 2.24-2.32 and 3.25-3.26 (m, 1H), 2.74 (t, 2H), 3.27-3.35 (m) and 3.62-3.65 (m), 1H), 4.08-4.10 and 4.62-4.63 (m, 1H), 4.39 (t, 2H), 6.47-6.48 (m, 1H), 7.17-7.23 (m, 3H), 7.70 (d, 1H).

The following compounds were synthesised employing a similar method to the ones described in examples 6 and 7 above:

| Ex. | Structure | MW | IUPAC Name | MS-ESI m/z |
|---|---|---|---|---|
| 7-1 | 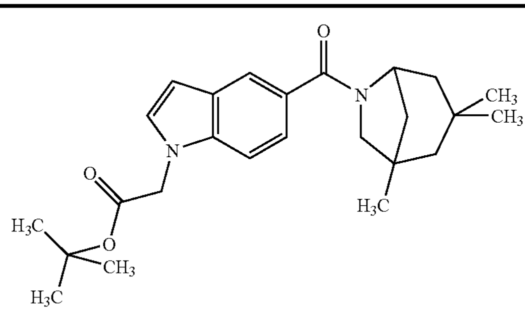 | 410.56 | [5-(1,3,3-Trimethyl-6-aza-bicyclo-[3.2.1]octane-6-carbonyl)-indol-1-yl]-acetic acid tert-butyl ester | 411 |
| 7-2 | 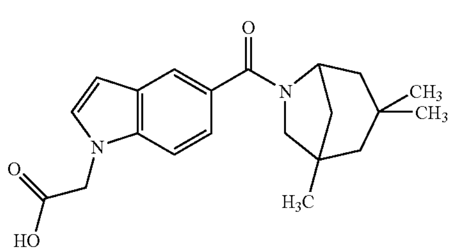 | 354.45 | [5-(1,3,3-Trimethyl-6-aza-bicyclo[3.2.1]octane-6-carbonyl)-indol-1-yl]-acetic acid | 355 |

-continued

| Ex. | Structure | MW | IUPAC Name | MS-ESI m/z |
|---|---|---|---|---|
| 7-3 | 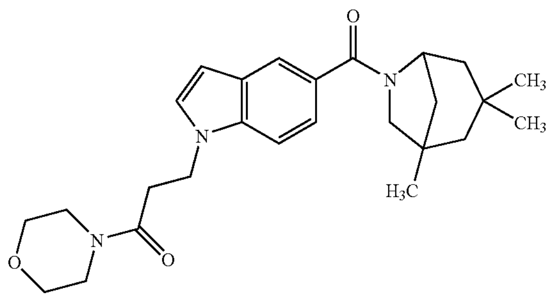 | 437.58 | 1-Morpholin-4-yl-3-[5-(1,3,3-trimethyl-6-aza-bicyclo[3.2.1]octane-6-carbonyl)-indol-1-yl]-propan-1-one | 438 |
| 7-4 | 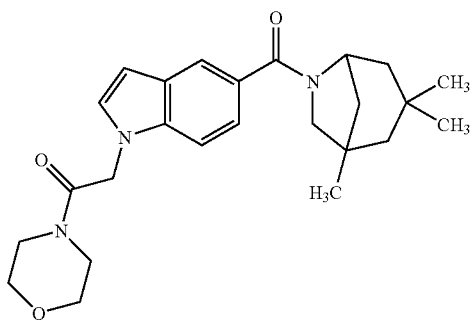 | 423.56 | 1-Morpholin-4-yl-2-[5-(1,3,3-trimethyl-6-aza-bicyclo[3.2.1]octane-6-carbonyl)-indol-1-yl]-ethanone | 424 |
| 7-5 | 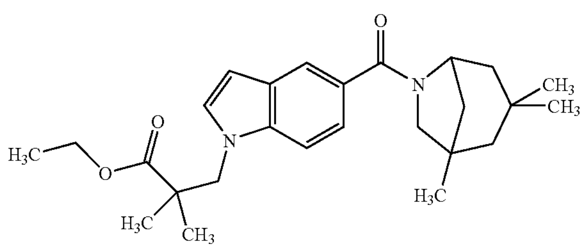 | 424.58 | 2,2-Dimethyl-3-[5-(1,3,3-trimethyl-6-aza-bicyclo[3.2.1]octane-6-carbonyl)-indol-1-yl]-propionic acid ethyl ester | 425 |
| 7-6 | 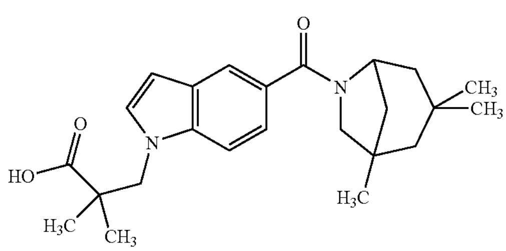 | 396.53 | 2,2-Dimethyl-3-[5-(1,3,3-trimethyl-6-aza-bicyclo[3.2.1]-octane-6-carbonyl)-indol-1-yl]-propionic acid | 397 |
| 7-7 | 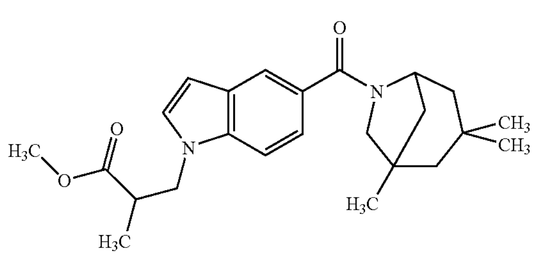 | 396.53 | 2-Methyl-3-[5-(1,3,3-trimethyl-6-aza-bicyclo[3.2.1]octane-6-carbonyl)-indol-1-yl]-propionic acid methyl ester | 397 |

| Ex. | Structure | MW | IUPAC Name | MS-ESI m/z |
|---|---|---|---|---|
| 7-8 | 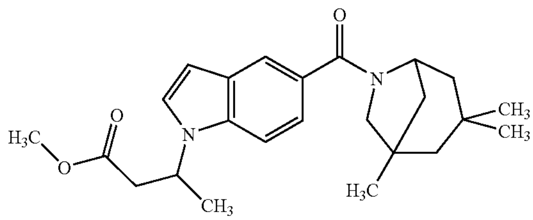 | 396.53 | 3-[5-(1,3,3-Trimethyl-6-aza-bicyclo[3.2.1]octane-6-carbonyl)-indol-1-yl]-butyric acid methyl ester | 397 |
| 7-9 | 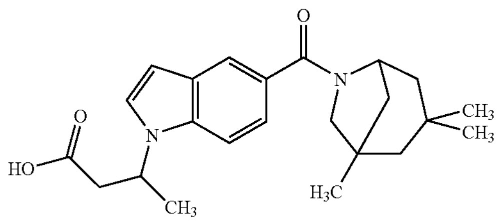 | 382.50 | 3-[5-(1,3,3-Trimethyl-6-aza-bicyclo[3.2.1]octane-6-carbonyl)-indol-1-yl]-butyric acid | 383 |
| 7-10 | 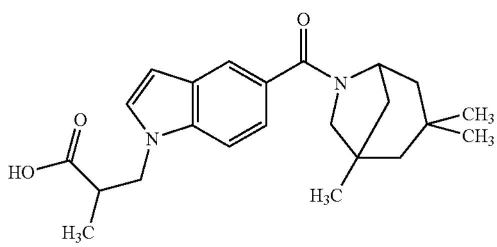 | 382.50 | 2-Methyl-3-[5-(1,3,3-trimethyl-6-aza-bicyclo[3.2.1]octane-6-carbonyl)-indol-1-yl]-propionic acid | 383 |
| 7-11 | 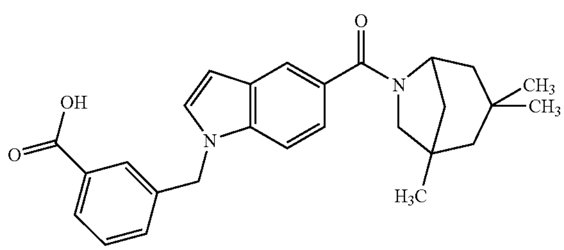 | 430.55 | 3-[5-(1,3,3-Trimethyl-6-aza-bicyclo[3.2.1]octane-6-carbonyl)-indol-1-ylmethyl]-benzoic acid | 431 |
| 7-12 | 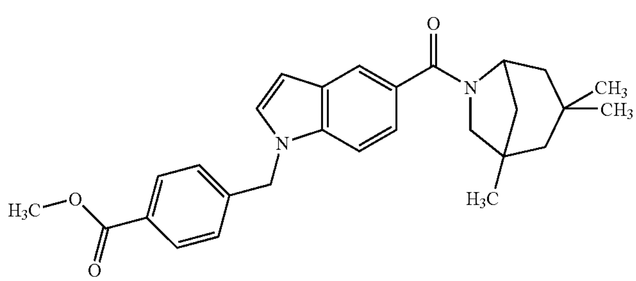 | 444.57 | 4-[5-(1,3,3-Trimethyl-6-aza-bicyclo[3.2.1]octane-6-carbonyl)-indol-1-ylmethyl]-benzoic acid methyl ester | 445 |
| 7-13 | 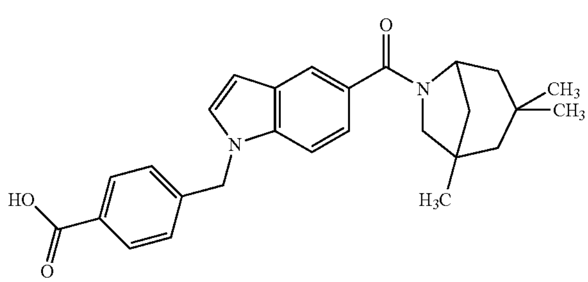 | 430.55 | 4-[5-(1,3,3-Trimethyl-6-aza-bicyclo[3.2.1]octane-6-carbonyl)-indol-1-ylmethyl]-benzoic acid | 431 |

| Ex. | Structure | MW | IUPAC Name | MS-ESI m/z |
|---|---|---|---|---|
| 7-14 | 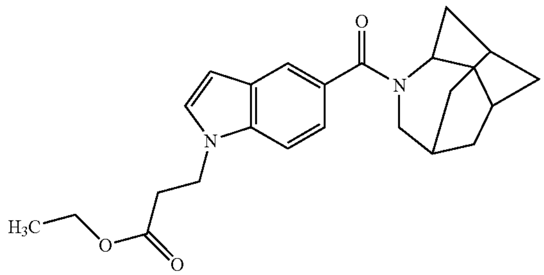 | 394.51 | 3-[5-(4-Aza-tricyclo[4.3.1.1*3,8*]-undecane-4-carbonyl)-indol-1-yl]-propionic acid ethyl ester | 395 |
| 7-15 | 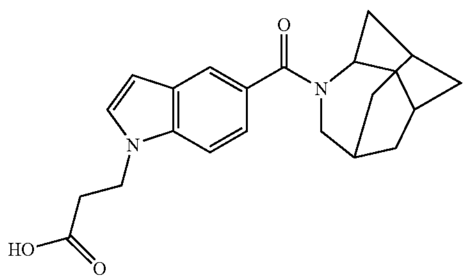 | 366.46 | 3-[5-(4-Aza-tricyclo[4.3.1.1*3,8*]-undecane-4-carbonyl)-indol-1-yl]-propionic acid | 367 |

Example 8

5-(1,3,3-Trimethyl-6-aza-bicyclo[3.2.1]octane-6-carbonyl)-1H-indole-2-carboxylic Acid Ethyl Ester

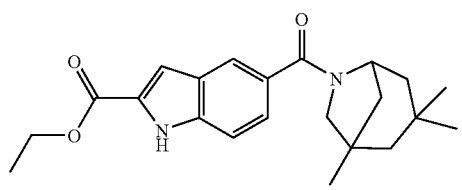

To a solution of 1H-Indole-2,5-dicarboxylic acid 2-ethyl ester (890 mg, 3.8 mmol) in dry DMF (10 mL) at room temperature under an inert atmosphere of nitrogen was added HOBt (570 mg, 4.2 mmol) and EDAC (951 mg, 4.9 mmol), and the resulting solution was stirred for 30 min. 1,3,3-Trimethyl-6-aza-bicyclo[3.2.1]octane hydrochloride (796 mg, 4.2 mmol) was added to the solution followed by DIPEA (1.98 mL, 11.4 mmol), and the reaction mixture was stirred for 16 h at room temperature. The reaction was quenched by the addition of water (20 mL) followed by extraction with DCM (3×50 mL). The combined organic phases were dried (MgSO$_4$), filtered, and evaporated in vacuo. The resulting solid was purified by silica gel chromatography using a mixture of ethyl acetate and heptane (1:2) as eluent. Pure fractions were collected, the solvent evaporated in vacuo and dried in vacuo at 50° C. affording 800 mg (57%) of the title compound as a solid. MS-ESI m/z 369; $^1$H NMR (300 MHz, CDCl$_3$) δ 0.94 (d, 3H), 1.04 (d, 3H), 1.14-1.19 (m, 4H), 1.24-1.29 (m, 2H), 1.39-1.45 (m, 4H), 1.58-1.63 (m, 1H), 1.76-1.79 (m, 1H), 3.25-3.30 (m, 1H), 3.35 (d) and 3.65 (d, 1H), 4.06-4.09 (m) and 4.64-4.67 (m, 1H), 4.42 (q, 2H), 7.27 (s, 1H), 7.39-7.46 (m, 2H), 7.82 (d, 1H), 9.05 (s, 1H).

Example 9

5-(1,3,3-Trimethyl-6-aza-bicyclo[3.2.1]octane-6-carbonyl)-1H-indole-2-carboxylic Acid

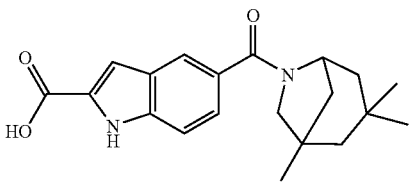

To a solution of 5-(1,3,3-trimethyl-6-aza-bicyclo[3.2.1]octane-6-carbonyl)-1H-indole-2-carboxylic acid ethyl ester (500 mg, 1.35 mmol) in ethanol (10 mL) was added 1N aqueous sodium hydroxide solution (10 mL), and the resulting solution stirred for 16 h. The solution was acidified with 1N hydrochloric acid solution before the organic volatiles were removed in vacuo and the aqueous residues were extracted with DCM (3×5 mL). The combined organic phases were dried (MgSO$_4$), filtered and evaporated in vacuo. The resulting solid was dried in vacuo at 50° C. affording 460 mg (100%) of the title compound as a solid. MS-ESI m/z 341; $^1$H NMR (300 MHz, DMSO-d$_6$) δ 0.88-0.99 (m, 6H), 1.07 (d, 3H), 1.16-1.19 (m, 1H), 1.27-1.50 (m, 4H), 1.74-1.77 (m, 1H), 3.10-3.19 (m, 1H), 3.40-3.48 (m, 1H), 3.99-4.07 (m) and 4.38-4.40 (m, 1H), 7.16 (s, 1H), 7.32-7.37 (m, 1H), 7.42-7.48 (m, 1H), 7.77 (d, 1H), 11.93 (s, 1H), 13.04 (s, 1H).

Example 10

[1-(2-Methanesulfonylmethoxy-ethyl)-1H-benzoimidazol-5-yl]-(octahydro-quinolin-1-yl)-methanone

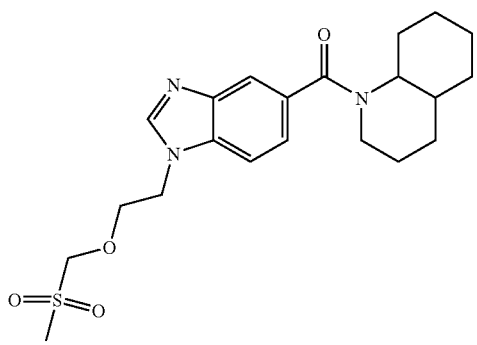

Step-A:

4-(2-Hydroxyethylamino)-3-nitro-benzoic Acid Methyl Ester

4-Fluoro-3-nitro-benzoic acid methyl ester (3 g, 15.64 mmol) was dissolved in DMF (20 ml) and DIPEA (5.8 g, 18.07 mmol) was added. 2-Aminoethanol (1.1 g, 18.07 mmol) was then added slowly by maintaining the temperature <20° C. Stirring continued at ambient temperature for 1 h. After checking the completion of reaction by TLC, the reaction mixture was added onto the ice cold water. The yellow solid which separated out was filtered, washed with cold water and finally washed with hexane affording 3.3 g (92%) of 4-(2-hydroxyethylamino)-3-nitro-benzoic acid methyl ester. $^1$H NMR (300 MHz, CDCl$_3$) δ 3.5 (q, 2H), 3.7 (q, 2H), 3.9 (s, 3H), 5.1 (t, 1H), 7.2 (d, 1H), 8.0 (d, 1H), 8.6 (s, 1H).

Step-B:

3-Amino-4-(2-hydroxy-ethylamino)-benzoic Acid Methyl Ester

To a solution of 4-(2-hydroxy-ethylamino)-3-nitro-benzoic acid methyl ester (3.0 g, 12.4 mmol) in methanol was added 10% Pd/C (800 mg). The mixture was hydrogenated at 1 atmospheric pressure for 2 h. The catalyst was filtered off and the methanol evaporated to give 2.6 g (99%) of 3-amino-4-(2-hydroxyethylamino)-benzoic acid methyl ester.

Step-C:

1-(2-Hydroxyethyl)-1H-benzoimidazole-5-carboxylic Acid Methyl Ester

3-Amino-4-(2-hydroxy-ethylamino)-benzoic acid methyl ester (2.6 g, 12.0 mmol) was dissolved in formic acid (20 mL). The solution was heated at 45° C. for 1 h. After checking the completion of reaction by TLC, formic acid was evaporated at <40° C. under reduced pressure and the resulting solid was recrystallized from EtOAc. The above solid was dissolved in 3N HCl, stirred at ambient temperature for 1 h, basified back with saturated sodium bicarbonate solution and extracted with EtOAc. The organic layer was evaporated to give 2.1 g (78%) of 1-(2-hydroxy-ethyl)-1H-benzoimidazole-5-carboxylic acid methyl ester. MS-ESI m/z 221 (M+1): $^1$H NMR (300 MHz, DMSO-d6) δ 3.7 (q, 2H), 3.9 (s, 3H), 4.3 (t, 3H), 5.0 (t, 1H), 7.7 (d, 1H), 7.9 (dd, 1H), 8.25 (s, 1H), 8.35 (s, 1H)

Step-D:

1-(2-Methylsulfanylmethoxy-ethyl)-1H-benzoimidazole-5-carboxylic Acid Methyl Ester A solution of 1-(2-hydroxyethyl)-1H-benzimidazole-5-carboxylic acid methyl ester (0.5 g. 2.27 mmol) in a mixture of dry THF:DME (25 mL:15 mL) was cooled to 5° C. NaH (0.081 g, 3.4 mmol) was added and stirred for 30 min at the same temperature. A mixture of chloromethyl methyl sulphide (0.285 g, 2.95 mmol) and NaI (0.408 g, 2.95 mmol) was then added slowly followed by TBAI (0.087 g, 0.22 mmol). The reaction was allowed to stir for overnight at ambient temperature. It was then quenched with saturated ammonium chloride solution and extracted with EtOAc. The organic layer was evaporated to give 0.53 g (83%) of 1-(2-methylsulfanylmethoxyethyl)-1H-benzimidazole-5-carboxylic acid methyl ester. $^1$H NMR (300 MHz, CDCl$_3$) δ 1.9 (s, 3H), 3.9 (t, 2H), 3.95 (s, 3H), 4.4 (t, 2H), 4.6 (s, 2H), 7.45 (d, 1H), 8.05 (m, 2H), 8.5 (d, 1H)

Step-E:

1-(2-Methanesulfonylmethoxy-ethyl)-1H-benzoimidazole-5-carboxylic Acid Methyl Ester A solution of 1-(2-methylsulfanylmethoxyethyl)-1H-benzimidazole-5-carboxylic acid methyl ester (3.0 g. 10.7 mmoles) in methanol (30 mL) was cooled to 0° C. and to this was added a solution of oxone (4.88 g, 7.94 mmoles) in water. The solution was stirred at the ambient temperature for 12 h. It was quenched with 5% sodium bicarbonate solution and extracted with EtOAc. Removal of solvent gave 2.0 g (60%) of 1-(2-methane-sulfonylmethoxy-ethyl)-1H-benzoimidazole-5-carboxylic acid methyl ester. MS-ESI m/z 313(M+1): $^1$H NMR (300 MHz, DMSO-d6) δ 2.9 (s, 3H), 4.0 (s, 3H), 4.25 (t, 2H), 4.65 (t, 2H), 4.75 (s, 2H), 7.85 (d, 2H), 8.0 (dd, 1H), 8.35 (s, 1H), 8.5 (s, 1H)

Step-F:

1-(2-Methanesulfonylmethoxy-ethyl)-1H-benzoimidazole-5-carboxylic Acid 1-(2-Methanesulfonylmethoxyethyl)-1-H-benzimidazole-5-carboxylic acid methyl ester (1.0 g, 3.2 mmoles) was dissolved in THF (5 mL). A solution of LiOH (0.38 g, 16 mmol) in water was added and the mixture stirred vigorously for 1 h. The reaction was acidified with 2N HCl to pH 2 at 5-10° C. It was then filtered to give 0.8 g (84%) of 1-(2-methanesulfonylmethoxyethyl)-1H-benzoimidazole-5-carboxylic acid. $^1$H NMR (300 MHz, DMSO-d6) δ 2.9 (s, 3H), 4.2 (t, 2H), 4.5 (t, 2H), 4.65 (s, 2H), 7.75 (d, 1H), 7.9 (dd, 1H), 8.25 (d, 1H), 8.35 (s, 1H), 12.7 (s, 1H)

Step-G:

[1-(2-Methanesulfonylmethoxy-ethyl)-1H-benzoimidazol-5-yl]-(octahydro-quinolin-1-yl)-methanone To a solution of 1-(2-methanesulfonylmethoxyethyl)-1H-benzimidazole-5-carboxylic acid (0.5 g, 1.677 mmol) in DMF (5 mL) was added decahydroquinoline (0.257 g, 1.845 mmol) followed by HOBt (0.25 g, 1.845 mmol) and DIPEA (0.65 g, 5 mmol). The reaction mixture was cooled to 0° C. and EDCl.HCl (0.354 g, 1.845 mmol) was added. It was gradually raised to ambient temperature and stirring continued for 12 h. The solvent was then evaporated, the residue diluted with water (5 mL) and extracted with $CH_2Cl_2$ (3×25 mL). The combined organic phases were washed with brine solution, dried ($Na_2SO_4$) and the solvent evaporated affording the crude amide which was purified by preparative HPLC to give 0.3 g (43%) of [1-(2-methanesulfonylmethoxy-ethyl)-1H-benzimidazol-5-yl]-(octahydroquinolin-1-yl)methanone. MS-ESI m/z 420 (M+1): $^1$H NMR (300 MHz, DMSO-d6) δ 1.1-1.9 (br, 13H), 2.8 (s, 3H), 3.0-3.3 (m, 2H), 4.15 (t, 2H), 4.5 (t, 2H), 4.65 (s, 2H), 7.3 (m, 1H), 7.6 (m, 1H), 7.7 (d, 1H), 8.3 (s, 1H)

The following compounds were synthesised employing a similar method to the ones described in example 10 above:

| Ex. | Structure | MW | IUPAC Name | MS-ESI m/z |
|---|---|---|---|---|
| 10-1 | 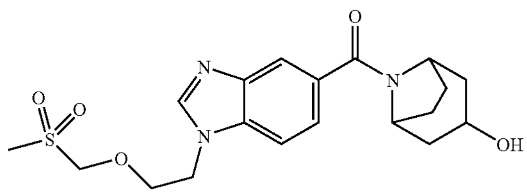 | 407.49 | (3-Hydroxy-8-aza-bicyclo-[3.2.1]oct-8-yl)-[1-(2-methane-sulfonylmethoxy-ethyl)-1H-benzoimidazol-5-yl]-methanone | 408 |
| 10-2 | 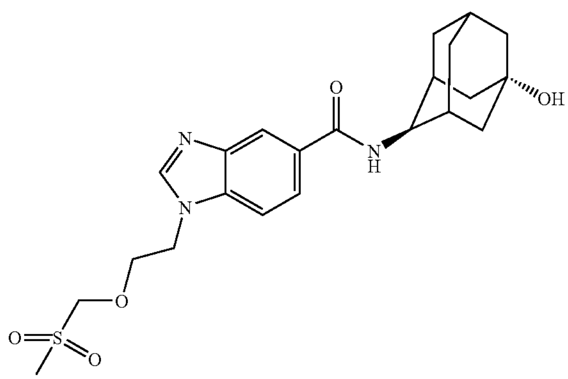 | 447.56 | trans-1-(2-Methanesulfonyl-methoxy-ethyl)-1H-benzo-imidazole-5-carboxylic acid (5-hydroxy-adamantan-2-yl)-amide | 448 |
| 10-3 | 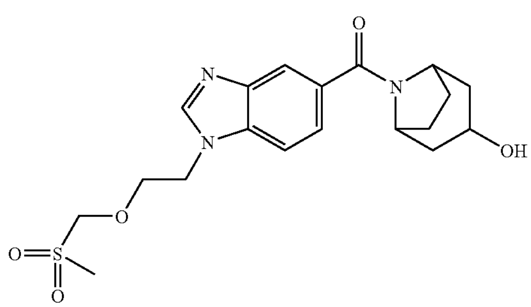 | 447.56 | Cis-1-(2-Methanesulfonyl-methoxy-ethyl)-1H-benzo-imidazole-5-carboxylic acid (5-hydroxy-adamantan-2-yl)-amide | 448 |
| 10-4 | 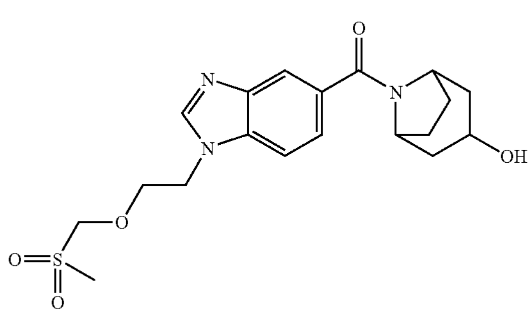 | 407.49 | (3-Hydroxy-8-aza-bicyclo-[3.2.1]oct-8-yl)-[1-(2-methane-sulfonylmethoxy-ethyl)-1H-benzoimidazol-5-yl]-methanone | 408 |

Example 11

1-(2-Methanesulfonyl-ethyl)-1H-benzoimidazole-5-carboxylic Acid (5-hydroxy-adamantan-2-yl)-amide

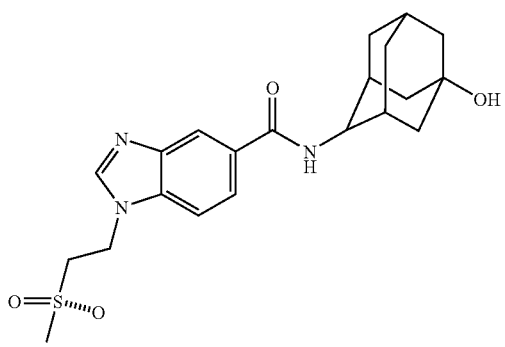

Step A:

2-(2-Methylsulfanylethyl)isoindol-1,3-dione

To a solution of N-bromoethylphthalimide (1 g, 3.953 mmol) in methanol (25 mL), was added NaSMe (0.415 g, 5.929 mmol) under $N_2$ atmosphere at 0° C. The reaction mixture was allowed to stir at ambient temperature for 2 h. The reaction mass was concentrated, diluted with water and extracted with EtOAc (3×25 mL). The organic layer was washed with brine solution and dried over anhydrous $Na_2SO_4$ and concentrated to give 2-(2-Methylsulfanylethyl)isoindol-1,3-dione (0.88 g, 80%). MS-ESI m/z 222 (M+1); $^1$H NMR (300 MHz, CDCl$_3$) δ 7.7 (m, 2H), 7.9 (m, 2H), 3.9 (t, 1H), 2.8 (t, 2H), 2.2 (s, 3H).

Step-B:

2-(2-Methanesulfonyl-ethyl)-isoindole-1,3-dione

To a solution of 2-(2-methylsulfanylethyl)-isoindole-1,3-dione (2.5 g, 11.30 mmol) in acetic acid (10 mL) was added 30% hydrogen peroxide (6 mL) at 0° C. The reaction mixture was brought to room temp and stirred for 2 h. Excess hydrogen peroxide in the reaction mixture was quenched with a saturated solution of sodium sulphite, and the resulting solution extracted with CHCl$_3$. The organic layer was washed with brine, dried over $Na_2SO_4$ and evaporated to give 2-(2-Methanesulfonyl-ethyl)-isoindole-1,3-dione (2.3 g, 83%). $^1$H NMR (300 MHz, CDCl$_3$) δ 7.9 (m, 2H), 7.8 (m, 2H), 4.2 (t, 1H), 3.4 (t, 1H), 3.1 (s, 3H).

Step-C:

2-Methanesulfonyl-ethylamine

Hydrazine hydrate (15 mL) was added to a solution of 2-(2-methanesulfonylethyl)-isoindole-1,3-dione (3.123 g, 12.344 mmol) in a mixture of CHCl$_3$-ethanol (:1) at 0° C. It was then stirred overnight at room temperature. It was filtered and the filtrate concentrated to give 2-Methanesulfonylethylamine (1.2 g, 80%). $^1$H NMR (300 MHz, CDCl$_3$) δ 3.05 (t, 2H), 3.15 (t, 2H), 3.0 (s, 3H).

Step-D:

4-(2-Methanesulfonyl-ethylamino)-3-nitro-benzoic Acid Methyl Ester

To a solution of 2-methanesulfonylethylamine (1.3 g, 10.56 mmol) and DIPEA (3.5 mL, 31.69 mmol) in DMF (15 mL) was added 4-fluoro-3-nitro-benzoic acid methyl ester (1.2 g, 15.84 mmol) in portions. The reaction mixture was allowed to stir for 15 h at room temperature. It was then diluted with water and extracted with EtOAc. The organic layers were washed with water, brine and concentrated to give 4-(2-methanesulfonyl-ethylamino)-3-nitro-benzoic acid methyl ester (83%). $^1$H NMR (300 MHz, CDCl$_3$) δ 8.9 (d, 1H), 8.6 (t, 1H), 8.2 (d, 1H), 6.9 (d, 1H), 4.0 (q, 2H), 3.9 (s, 3H), 3.4 (t, 2H), 3.0 (s, 3H).

Step-E:

1-(2-Methanesulfonyl-ethyl)-1H-benzoimidazole-5-carboxylic Acid Methyl Ester 4-(2-Methanesulfonyl-ethylamino)-3-nitro-benzoic acid methyl ester (1.63 g, 5.40 mmol) was dissolved in methanol, and 10% Pd/C (150 mg) was added to it under $N_2$ atmosphere. The reaction mixture was then hydrogenated at 1 atmospheric pressure at room temp for 2 h. It was filtered through celite and the filtrate concentrated to yield the desired product. The crude material (1.32 g, 4.85 mmol) was taken in formic acid (10 mL) and allowed to stir at 50° C. for 4 h. The reaction mass was concentrated, diluted with water and extracted with EtOAc. The organic layers were washed with saturated NaHCO$_3$, brine, dried over $Na_2SO_4$ and concentrated to give 1-(2-methanesulfonylethyl)-1H-benzoimidazole-5-carboxylic acid methyl ester (77%). $^1$H NMR (300 MHz, DMSO-d$_6$). δ 8.45 (s, 1H), 8.3 (s, 1H), 7.9 (d, 1H), 7.8 (d, 1H), 4.75 (t, 2H), 3.9 (s, 3H), 3.8 (t, 2H), 3.0 (s, 3H).

Step F:

1-(2-Methanesulfonyl-ethyl)-1H-benzoimidazole-5-carboxylic Acid

To a solution of 1-(2-methanesulfonylethyl)-1H-benzoimidazole-5-carboxylic acid methyl ester (0.2 g, 7.09 mmol) in methanol was added LiOH (50 mg) followed by water (1 mL). The reaction mixture was allowed to stir at room temp for 2 h. it was then concentrated to remove methanol and the aqueous layer was acidified with citric acid. The precipitated product was filtered to give 1-(2-Methanesulfonyl-ethyl)-1H-benzoimidazole-5-carboxylic acid (90%). MS-ESI m/z 269 (M+1); $^1$H NMR (300 MHz, DMSO-d$_6$) δ 12.6 (br, 1H), 8.4 (s, 1H), 8.2 (s, 1H), 7.9 (d, 1H), 7.8 (d, 1H), 4.8 (t, 2H), 3.8 (t, 2H), 3.0 (s, 3H).

Step G:

1-(2-Methanesulfonyl-ethyl)-1H-benzoimidazole-5-carboxylic acid (5-hydroxy-adamantan-2-yl)-amide To a solution of 1-(2-methanesulfonylethyl)-1H-benzoimidazole-5-carboxylic acid (0.2 g, 0.74 mmol) in DMF (5 mL) was added HOBt (0.15 g, 0.89 mmol), DIPEA (0.4 mL, 2.23 mmol), 4-aminoadamantan-1-ol (0.15 g 0.89 mmol) and EDCl (0.21 g, 1.11 mmol) successively under $N_2$ atmosphere. The reaction mixture was allowed to stir over night at room temperature. It was diluted with water and extracted with CHCl$_3$. The organic layer was washed with saturated NaHCO$_3$ solution, brine and dried over anhydrous $Na_2SO_4$. Concentration of the organic layer gave 1-(2-methanesulfonylethyl)-1H-benzoimidazole-5-carboxylic acid (5-hydroxy-adamantan-2-yl)-amide (0.05 g). MS-ESI m/z 418 (M+1); $^1$H NMR (300 MHz, CDCl$_3$) δ 8.2 (s, 1H), 8.1 (s, 1H), 7.9 (d, 1H), 7.5 (d, 1H), 6.4 (d, 1H), 4.8 (t, 2H), 4.2 (m, 1H), 3.6 (t, 2H), 2.7 (s, 3H), 2.4 (s, 2H), 2.3 (m, 1H), 1.8 (m, 11H).

The following compounds were synthesised employing a similar method to the ones described in example 11 above:

| Ex. | Structure | MW | IUPAC Name | MS-ESI m/z |
|---|---|---|---|---|
| 11-1 | 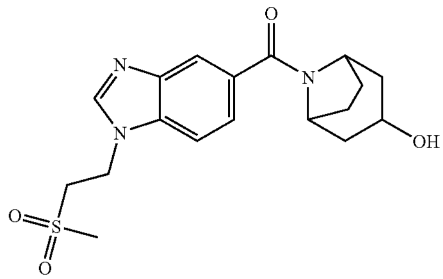 | 377.47 | (3-Hydroxy-8-aza-bicyclo[3.2.1]oct-8-yl)-[1-(2-methanesulfonyl-ethyl)-1H-benzoimidazol-5-yl]-methanone | 378 |
| 11-2 | 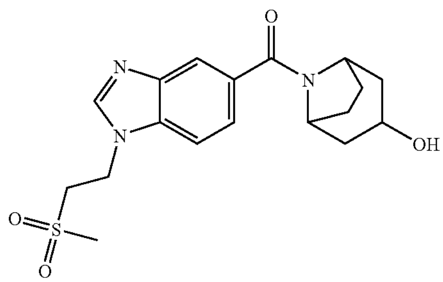 | 377.47 | (3-Hydroxy-8-aza-bicyclo[3.2.1]oct-8-yl)-[1-(2-methanesulfonyl-ethyl)-1H-benzoimidazol-5-yl]-methanone | 378 |
| 11-3 | 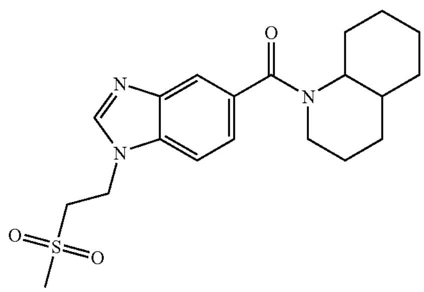 | 389.52 | [1-(2-Methanesulfonyl-ethyl)-1H-benzoimidazol-5-yl]-(octahydro-quinolin-1-yl)-methanone | 390 |
| 11-4 | 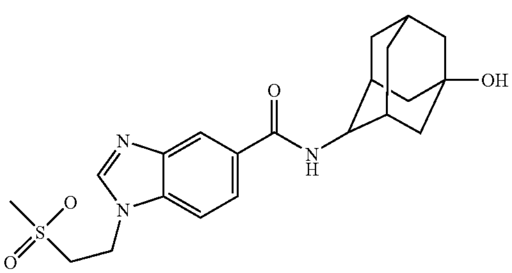 | 417.53 | 1-(2-Methanesulfonyl-ethyl)-1H-benzoimidazole-5-carboxylic acid (5-hydroxy-adamantan-2-yl)-amide | 418 |

Example 12

(3-Hydroxy-8-aza-bicyclo[3.2.1]oct-8-yl)-{1-[2-(1H-tetrazol-5-yl)-ethyl]-1H-benzoimidazol-5-yl}-methanone

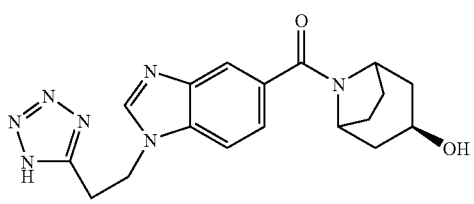

Step-A:

4-(2-Cyano-ethylamino)-3-nitro-benzoic Acid Methyl Ester

To a solution of 4-fluoro-3-nitro-benzoic acid methyl ester (4.95 g, 24.8 mmol) in DMF (25 ml) was added 3-aminopropionitrile fumarate (3.18 g, 12.4 mmol) and DIPEA (15 ml, 84.3 mmol). The mixture was stirred at room temperature for 2 h. The solvent was evaporated under vacuum and the residue diluted with water (50 mL). It was extracted with EtOAc (3×100 mL) and the organic phase washed with brine solution and dried ($Na_2SO_4$). Removal of solvent gave 4-(2-cyanoethylamino)-3-nitro-benzoic acid methyl ester (6.19 g, 98.5%). MS-ESI m/z 250 (M+1); $^1$H NMR (300 MHz, $CDCl_3$) δ 2.8 (t, 2H), 3.8 (m, 2H), 6.9 (d, 1H), 8.2 (m, 1H), 8.5 (t, 1H), 8.9 (s, 1H)

Step-B:

3-Amino-4-(2-cyanoethylamino)-benzoic Acid Methyl Ester

To a solution of ammonium chloride (21.7 g, 406.3 mmol) in water (200 mL) was added 4-(2-cyanoethylamino)-3-nitro-benzoic acid methyl ester (6.1 g, 24.5 mmol) followed by zinc powder (42.8 g, 655.9 mmol). The mixture was heated to 60° C. for 3 h. It was filtered hot and washed with EtOAc. The filtrate was further extracted with EtOAc and the combined organic phase washed with brine solution. The organic layer was evaporated to give 4.1 g (75%) of 3-amino-4-(2-cyano-ethylamino)-benzoic acid methyl ester. MS-ESI m/z 220 (M+1); $^1$H NMR (300 MHz, CDCl$_3$) δ 2.7 (t, 2H), 3.6 (m, 2H), 3.8 (s, 3H), 4.3 (bs, 1H), 6.6 (d, 1H), 7.45 (d, 1H), 7.6 (d, 1H)

Step-C:

1-(2-Cyano-ethyl)-1H-benzoimidazole-5-carboxylic Acid Methyl Ester

To 3-amino-4-(2-cyano-ethylamino)-benzoic acid methyl ester (4.0 g) was added formic acid (25 ml) and the mixture heated to 50° C. for 3 h. It was then concentrated and the residue recrystallised from EtOAc to afford 4.0 g (95%) of 1-(2-cyanoethyl)-1H-benzimidazole-5-carboxylic acid methyl ester. MS-ESI m/z 230 (M+1); $^1$H NMR (300 MHz, CDCl$_3$) δ 2.95 (t, 2H), 4.0 (s, 3H), 4.55 (t, 2H), 7.4 (d, 1H), 8.1 (m, 1H), 8.15 (s, 1H), 8.55 (s, 1H)

Step-D:

1-(2-Cyanoethyl)-1H-benzoimidazole-5-carboxylic Acid

To a solution of 1-(2-cyanoethyl)-1H-benzimidazole-5-carboxylic acid methyl ester (4.0 g, 17.4 mmol) in THF (30 mL) was added LiOH (1.67 g, 69.79 mmol) in water (8 mL) followed by MeOH (2 mL). Stirring continued at the ambient temperature for 1 h. It was then concentrated and acidified with 2N HCl. The solids formed were filtered and dried which afforded 1-(2-cyanoethyl)-1H-benzoimidazole-5-carboxylic acid (3.5 g, 95%). $^1$H NMR (300 MHz, DMSO-d$_6$) δ 3.1 (t, 2H), 4.6 (t, 2H), 7.8 (d, 1H), 7.9 (dd, 1H), 8.25 (d, 1H), 8.42 (s, 1H)

Step-E:

3-[5-(3-Hydroxy-8-aza-bicyclo[3.2.1]octane-8-carbonyl)-benzoimidazol-1-yl]-propionitrile To a solution of 1-(2-cyanoethyl)-1H-benzoimidazole-5-carboxylic acid (0.25 g, 1.16 mmol) in DMF (2.5 mL) was added with stirring HOBt (0.17 g, 1.27 mmol) followed by exo-nortropinol hydrochloride (0.21 g, 1.27 mmol), DIPEA (0.45 g, 3.48 mmol). EDCl.HCl was then added and it was stirred at room temperature for 12 h. The solvent was then evaporated and to the residue diluted with water (5 mL) and extracted with CH$_2$Cl$_2$. The organic phase was washed with brine solution, dried (Na$_2$SO$_4$) and the solvent evaporated. The residue was purified by preparative HPLC which afforded 0.26 g (67%) of 3-[5-(3-Hydroxy-8-aza-bicyclo [3.2.1]octane-8-carbonyl)-benzoimidazol-1-yl]-propionitrile. MS-ESI m/z 325 (M+1).

Step-F:

3-Hydroxy-8-aza-bicyclo[3.2.1]oct-8-yl)-{1-[2-(1H-tetrazol-5-yl)-ethyl]-1H-benzoimidazol-5-yl}-methanone To a solution of 3-[5-(3-Hydroxy-8-aza-bicyclo[3.2.1]octane-8-carbonyl)-benzoimidazol-1-yl]-propionitrile (250 mg, 0.7 mmol) in DMF (5 mL) was added sodium azide (184 mg, 2.83 mmol) and ammonium chloride (152 mg, 2.83 mmol) and heated to 100° C. for 12 h. The solvent was evaporated completely; methanol (20 mL) was added and filtered. The filtrate was concentrated and the residue purified by preparative HPLC to give 36 mg (13%) of 3-hydroxy-8-aza-bicyclo[3.2.1]oct-8-yl)-{1-[2-(1H-tetrazol-5-yl)-ethyl]-1H-benzoimidazol-5-yl}-methanone. MS-ESI m/z 368 (M+1); $^1$H NMR (300 MHz, DMSO-d$_6$) δ 1.3-2.0 (m, 8H), 3.15 (s, 1H), 3.5 (t, 2H), 3.9-4.0 (m, 2H), 4.6 (br, 1H), 4.75 (t, 2H), 7.4 (dd, 1H), 7.6-7.7 (m, 2H), 8.25 (s, 1H).

The following compounds were synthesised employing a similar method to the ones described in example 11 above:

| Ex. | Structure | MW | IUPAC Name | MS-ESI m/z |
|---|---|---|---|---|
| 12-1 | 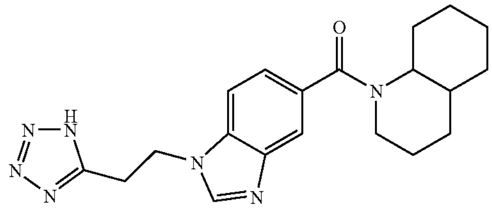 | 379.41 | (Octahydro-quinolin-1-yl)-{1-[2-(1H-tetrazol-5-yl)-ethyl]-1H-benzoimidazol-5-yl}-methanone | 380 |
| 12-2 | 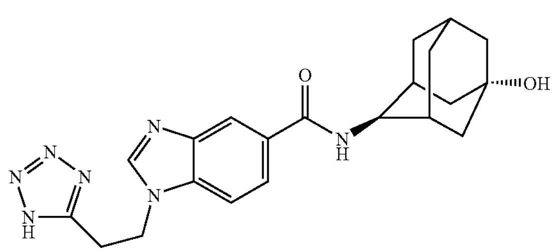 | 407.48 | Trans-1-[2-(1H-Tetrazol-5-yl)-ethyl]-1H-benzoimidazole-5-carboxylic acid (5-hydroxy-adamantan-2-yl)-amide | 355 |

| Ex. | Structure | MW | IUPAC Name | MS-ESI m/z |
|---|---|---|---|---|
| 12-3 | 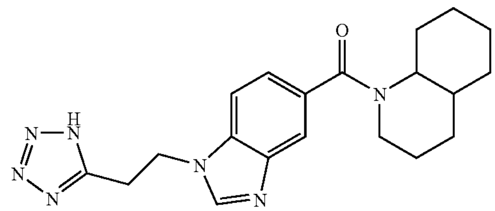 | 477.48 | Cis-1-[2-(1H-Tetrazol-5-yl)-ethyl]-1H-benzoimidazole-5-carboxylic acid (5-hydroxy-adamantan-2-yl)-amide | 438 |

Example 13

3-Hydroxy-pyrrolidine-1-carboxylic acid {2-[5-(3-hydroxy-8-aza-bicyclo[3.2.1]octane-8-carbonyl)-benzoimidazol-1-yl]-ethyl}-amide

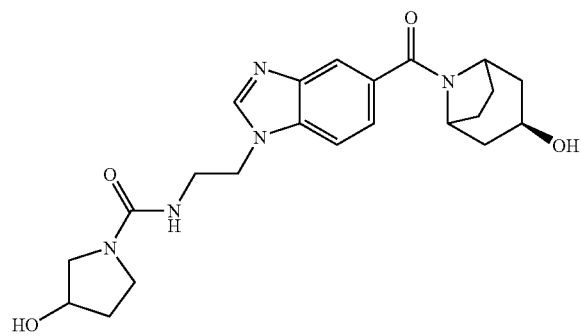

Step-A:

4-Fluoro-3-nitro-benzoic Acid Methyl Ester

To a solution of 4-fluoro-3-nitrobenzoic acid (16.0 g, 0.0864 mol) in dry DMF (100 mL) was added with stirring potassium carbonate (59.0 g, 0.43 mol) followed by methyl iodide (24.5 g, 0.173 mol) and the mixture was stirred for 3 h at ambient temperature. The reaction mixture was diluted with ice water (500 mL), extracted with EtOAc (3×100 mL) and the combined organic phases were washed with water (3×100 mL) and saturated brine solution (100 mL). The organic phase was dried ($Na_2SO_4$) and the solvent evaporated affording 17.0 g (99%) of 4-fluoro-3-nitro-benzoic acid methyl ester.

Step-B:

4-(2-Chloroethylamino)-3-nitro-benzoic Acid Methyl Ester

To a solution of 4-fluoro-3-nitro-benzoic acid methyl ester (10.0 g, 0.0502 mol) in dry DMF (100 mL) was added with stirring potassium carbonate (59.0 g, 0.43 mol) followed by 2-chloroethylamine hydrochloride (8.7 g, 0.075 mol) and the mixture was stirred for 15 h at ambient temperature. The reaction mixture was diluted with ice water (500 mL) and the solid precipitated was filtered, washed with water and dried under vacuum to get a yellow solid (12.7 g, 98%). MS-ESI m/z 259 (M+1).

Step-C:

3-Amino-4-(2-chloroethylamino)-benzoic Acid Methyl Ester

To a solution of 4-(2-chloroethylamino)-3-nitro-benzoic acid methyl ester (12.7 g, 0.0492 mol) in methanol (500 mL) was added 10% Pd/C (1.3 g) under a $N_2$ atmosphere. The reaction mixture was hydrogenated in a Parr apparatus at 3 kg pressure for 2 h. The catalyst was filtered over celite and the filtrate was concentrated affording 11.0 g (98%) of 3-amino-4-(2-chloroethylamino)-benzoic acid methyl ester as a solid.

Step-D:

1-(2-Chloroethyl)-1H-benzimidazole-5-carboxylic Acid Methyl Ester

To 3-amino-4-(2-chloroethylamino)-benzoic acid methyl ester (11.0 g, 0.0482 mol) was added $HCO_2H$ (30 mL) and heated at 100° C. for 1 h. The reaction was cooled to ambient temperature and diluted with ice water (100 mL). The pH of the reaction mixture was adjusted to 7 with $NaHCO_3$ and the solid precipitated was filtered, washed with water and dried under vacuum to get a pale green solid (9.9 g, 86%) of 1-(2-chloroethyl)-1H-benzimidazole-5-carboxylic acid methyl ester. MS-ESI m/z 239 (M+1).

Step-E:

1-(2-Azidoethyl)-1H-benzimidazole-5-carboxylic Acid Methyl Ester

To a solution of 1-(2-chloroethyl)-1H-benzimidazole-5-carboxylic acid methyl ester (9.9 g, 0.0416 mol) in dry DMSO (90 mL) was added with stirring $NaN_3$ (5.4 g, 0.0832 mol) and the mixture was stirred for 15 h at 75° C. The reaction mixture was cooled to ambient temperature and diluted with ice water (500 mL) and the solid precipitated was filtered, washed with water and dried under vacuum affording 9.3 g (91%) of 1-(2-azidoethyl)-1H-benzimidazole-5-carboxylic acid methyl ester as a solid. MS-ESI m/z 246 (M+1); $^1$H NMR (300 MHz, DMSO-$d_6$) δ 3.8 (t, 2H), 3.9 (s, 3H), 4.5 (t, 2H), 7.8 (d, 1H), 7.9 (dd, 1H), 8.25 (s, 1H), 8.4 (s, 1H).

Step-F:

1-(2-Azido-ethyl)-1H-benzimidazole-5-carboxylic Acid

To a solution of 1-(2-azidoethyl)-1H-benzimidazole-5-carboxylic acid methyl ester (5.0 g, 0.0204 mol) in THF/water 1:1 (100 mL) was added with stirring LiOH (0.73 g, 0.0306 mol) and the mixture was stirred for 5 h at ambient temperature. The solvent was evaporated and to the residue was added ice water (100 mL). The pH of the reaction mixture was adjusted to 5 with 1N HCl and the mixture extracted with EtOAc (5×100 mL). The combined organic phases were washed with saturated brine solution (100 mL), dried ($Na_2SO_4$) and the solvent evaporated affording 4.2 g (89%) of 1-(2-azidoethyl)-1H-benzimidazole-5-carboxylic acid as an ash coloured solid. MS-ESI m/z 232 (M+1); $^1$H NMR (300 MHz, DMSO-$d_6$) δ 3.8 (t, 2H), 4.5 (t, 2H), 7.8 (d, 1H), 7.9 (d, 1H), 8.25 (s, 1H), 8.4 (s, 1H).

Step-G:

[1-(2-Azidoethyl)-1H-benzimidazol-5-yl]-(3-hydroxy-8-azabicyclo[3.2.1]oct-8-yl)methanone To a solution of 1-(2-azidoethyl)-1H-benzimidazole-5-carboxylic acid (0.82 g, 0.00357 mol) in dry DMF (8.0 mL) was added with stirring HOBt (0.578 g, 0.00428 mol), DIPEA (1.9 mL, 0.0107 mol), 8-azabicyclo[3.2.1]octan-3-ol (0.5 g, 0.00393 mol) and the mixture was cooled to 0° C. To the resulting mixture was added EDCl (0.82 g, 0.00428 mol) and stirred for 15 h at ambient temperature. The reaction mixture was then diluted with ice water (100 mL), extracted with EtOAc (3×50 mL) and the combined organic phases were washed with water (3×50 mL) and saturated brine solution (50 mL). The organic phase was dried ($Na_2SO_4$) and the solvent evaporated affording (1.1 g, 98%) of [1-(2-azidoethyl)-1H-benzimidazol-5-yl]-(3-hydroxy-8-azabicyclo[3.2.1]oct-8-yl)methanone. MS-ESI m/z 341 (M+1).

Step-H:

[1-(2-Amino-ethyl)-1H-benzoimidazol-5-yl]-(3-hydroxy-8-aza-bicyclo[3.2.1]oct-8-yl)-methanone To a solution of [1-(2-azidoethyl)-1H-benzimidazol-5-yl]-(3-hydroxy-8-aza-bicyclo[3.2.1]oct-8-yl)methanone (1.1 g, 0.0035 mol) in methanol (15 mL) was added 10% Pd/C (0.17 g) and the mixture hydrogenated at 3 kg pressure for 1 h. The catalyst was filtered over celite and the filtrate was concentrated to give [1-(2-aminoethyl)-1H-benzimidazol-5-yl]-(3-hydroxy-8-aza-bicyclo[3.2.1]oct-8-yl)methanone (0.87 g, 86%). MS-ES I m/z 315 (M+1).

Step-I:

3-Hydroxypyrrolidine-1-carboxylic acid {2-[5-(3-hydroxy-8-azabicyclo[3.2.1]octane-8-carbonyl)-benzoimidazol-1-yl]-ethyl}amide A) 3-Hydroxypyrrolidine-1-carbonyl Chloride To a solution of pyrrolidin-3-ol (0.083 g, 0.955 mmol) in dry THF (5 mL) was added DIPEA (0.3 mL, 1.91 mmol) and cooled 0° C. To the resulting mixture was added triphosgene (0.127 g, 0.429 mmol) and the mixture was stirred for 2 h at an ambient temperature.

B) To a solution of [1-(2-aminoethyl)-1H-benzimidazol-5-yl]-(3-hydroxy-8-aza-bicyclo[3.2.1]oct-8-yl)methanone (0.25 g, 0.79 mmol) in dry THF (5 mL) was added DIPEA (0.3 mL, 1.91 mmol) at 0° C. To this reaction mixture was added compound A slowly and stirred for 3 days at an ambient temperature. The solvent was evaporated and the residue purified by preparative HPLC to afford 175 mg (54%) of 3-hydroxy-pyrrolidine-1-carboxylic acid {2-[5-(3-hydroxy-8-aza-bicyclo[3.2.1]octane-8-carbonyl)-benzoimidazol-1-yl]-ethyl}-amide. MS-ESI m/z 428 (M+1); $^1$H-NMR (300 MHz, $CD_3OD$) δ 1.5 (t, 1H), 1.9 (m, 6H), 2.1 (m, 3H), 3.2 (m, 2H), 3.5 (t, 2H), 4.2 (m, 2H), 4.4 (m, 1H), 4.5 (t, 2H), 4.8 (s, 1H), 7.45 (dd, 1H), 7.7 (d, 1H), 7.8 (s, 1H), 8.25 (s, 1H), Example 14

4-Hydroxy-piperidine-1-carboxylic acid {2-[5-(octahydro-quinoline-1-carbonyl)benzoimidazol-1-yl]-ethyl}-amide

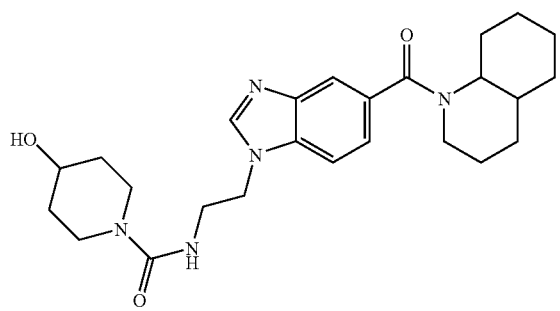

Steps A-F is similar to those used in example 13 above.

Step-G:

[1-(2-azidoethyl)-1H-benzimidazol-5-yl]-(octahydroquinolin-1-yl)methanone

To a solution of 1-(2-azidoethyl)-1H-benzimidazole-5-carboxylic acid (1 g, 0.00433 mol) in dry DMF (7.0 mL) was added with stirring HOBt (0.876 g, 0.00649 mol), DIPEA (2.25 mL, 0.0129 mol), decahydroquinoline (0.902 g, 0.00649 mol) at 0° C. To the resulting mixture was added EDCl (1.24 g, 0.00649 mol) and stirred for 15 h at an ambient temperature. The reaction mixture was diluted with ice water (100 mL) and extracted with EtOAc (3×50 mL). The combined organic phases were washed with water, dried ($Na_2SO_4$) and the solvent evaporated to give [1-(2-azidoethyl)-1H-benzimidazol-5-yl]-(octahydroquinolin-1-yl)methanone (1.5 g, 98%).

Step-H:

[1-(2-Aminoethyl)-1H-benzimidazol-5-yl]-(octahydroquinolin-1-yl)methanone

To a solution of [1-(2-azidoethyl)-1H-benzimidazol-5-yl]-(octahydroquinolin-1-yl)methanone (1.8 g, 0.0051 mol) in methanol (10 mL) was added 10% Pd/C (0.2 g). The reaction mixture was hydrogenated at 3 kg pressure for 2 h. The catalyst was filtered over celite and the filtrate was concentrated to give [1-(2-aminoethyl)-1H-benzimidazol-5-yl]-(octahydroquinolin-1-yl)methanone (1.5 g, 90%).

Step-I:

4-Hydroxypiperidine-1-carboxylic acid {2-[5-(octahydroquinoline-1-carbonyl)benzimidazol-1-yl] ethyl}amide A) 4-Hydroxypiperidine-1-carbonyl Chloride To a solution of piperidin-4-ol (0.074 g, 0.73 mmol) in dry THF (5 mL) was added DIPEA (0.3 mL, 1.91 mmol) at 0° C. To the resulting mixture was added triphosgene (0.076 g, 2.1 mmol) and stirred for 2 h at ambient temperature.

B) To a solution of [1-(2-aminoethyl)-1H-benzimidazol-5-yl]-(octahydroquinolin-1-yl)methanone (0.2 g, 0.613 mmol) in dry THF (5 mL) was added DIPEA (0.3 mL, 1.91 mmol) at 0° C. To this reaction mixture was added compound A slowly and stirred for 2 h at ambient temperature. The solvent was evaporated and the residue purified by preparative HPLC affording cis and trans isomers of 4-hydroxypiperidine-1-carboxylic acid {2-[5-(octahydroquinoline-1-carbonyl)-benzimidazol-1-yl]ethyl}amide.

Isomer I (12 mg): MS-ESI m/z 454 (M+1); $^1$H-NMR (300 MHz, CD$_3$OD) δ 1.30-1.80 (m, 13H), 2.0 (m, 3H), 2.9 (m, 2H), 3.2 (m, 2H), 3.55 (t, 2H), 3.7 (m, 3H), 4.5 (t, 2H), 7.35 (d, 1H), 7.7 (m, 2H), 8.25 (s, 1H). HPLC (VERYPOL.M): tr=7.73 min (95%).

Isomer II (8 mg): MS-ESI m/z 454 (M+1); $^1$H-NMR (300 MHz, CD$_3$OD) δ 1.2 (m, 3H), 1.4 (m, 8H), 1.7 (m, 6H), 3.0 (m, 2H), 3.6 (t, 2H), 3.7 (m, 3H), 4.4 (t, 2H), 7.4 (dd, 1H), 7.65 (d, 1H), 7.7 (s, 1H), 8.3 (s, 1H). HPLC (VERYPOL.M): tr=7.86 min (94%).

Example 15

1-{2-[(4-Hydroxy-piperidine-1-carbonyl)-amino]-ethyl}-1H-benzoimidazole-5-carboxylic Acid (5-hydroxy-adamantan-2-yl)-amide

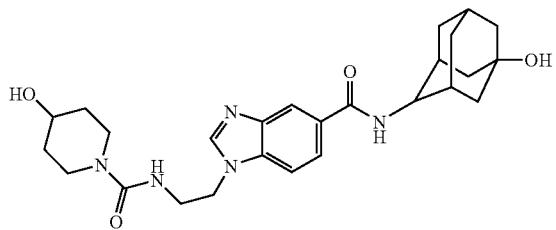

Steps A-F is similar to those used in example 14 above.
Step-G:

1-(2-Azidoethyl)-1H-benzimidazole-5-carboxylic Acid (5-hydroxyadamantan-2-yl)-amide To a solution of 1-(2-azidoethyl)-1H-benzimidazole-5-carboxylic acid (0.65 g, 0.0028 mol) in dry DMF (5.0 mL) was added with stirring HOBt (0.46 g, 0.0034 mol), DIPEA (2.5 mL, 0.014 mol), 4-aminoadamantan-1-ol (0.685 g, 0.0034 mol) at 0° C. To the resulting mixture was added EDCl (0.65 g, 0.0034 mol) and stirred for 15 h at ambient temperature. The reaction mixture was diluted with ice water (100 mL) and extracted with EtOAc (3×50 mL) and the combined organic phases were washed with water, dried (Na$_2$SO$_4$) and the solvent evaporated affording (1.0 g, 93.5%) of 1-(2-azidoethyl)-1H-benzimidazole-5-carboxylic acid (5-hydroxyadamantan-2-yl)-amide. MS-ESI m/z 381 (M+1).
Step-H:

1-[(2-Aminoethyl)-1H-benzimidazole-5-carboxylic Acid (5-hydroxy-adamantan-2-yl)]-amide To a solution of 1-(2-azidoethyl)-1H-benzimidazole-5-carboxylic acid (5-hydroxyadamantan-2-yl)-amide (1.0 g, 0.00263 mol) in methanol (20 mL) was added 10% Pd/C (200 mg). The reaction mixture was hydrogenated at 3 kg pressure for 1 h. The catalyst was filtered over celite and the filtrate was concentrated to give 1-(2-aminoethyl)-1H-benzimidazole-5-carboxylic acid (5-hydroxy-adamantan-2-yl)-amide (0.7 g, 75%).

Step-I:

1-{2-[(4-Hydroxypiperidine-1-carbonyl)-amino]-ethyl}-1H-benzoimidazole-5-carboxylic Acid (5-hydroxy-adamantan-2-yl)-amide To a solution of 1-(2-aminoethyl)-1H-benzimidazole-5-carboxylic acid (5-hydroxy-adamantan-2-yl)-amide (0.35 g, 0.988 mmol) in dry THF (5 mL) was added DIPEA (0.3 mL, 1.91 mmol) at 0° C. To this reaction mixture was added 4-hydroxypiperidine-1-carbonyl chloride slowly and stirred for 2 h at ambient temperature. The solvents were evaporated and the residue purified by preparative HPLC cis and trans isomers of 1-{2-[(4-hydroxypiperidine-1-carbonyl)-amino]-ethyl}-1H-benzoimidazole-5-carboxylic acid (5-hydroxyadamantan-2-yl)amide.

Isomer I (0.008 g): MS-ESI m/z 482 (M+1); $^1$H-NMR (300 MHz, CD$_3$OD): δ 1.4 (m, 3H), 1.6 (d, 3H), 1.8 (m, 9H), 2.0 (d, 2H), 2.2 (s, 1H), 2.4 (s, 2H), 2.9 (m, 2H), 3.5-3.8 (m, 5H), 4.0 (s, 1H), 4.5 (t, 2H), 7.65 (d, 1H), 7.8 (d, 1H), 7.95 (d, 1H), 8.15 (s, 1H), 8.25 (s, 1H). HPLC (VERYPOL.M): tr=6.59 min (95%).

Isomer II (0.022 g): MS-ESI m/z 482 (M+1); $^1$H-NMR (300 MHz, CD$_3$OD): δ 1.4 (m, 3H), 1.5 (d, 2H), 1.8 (m, 5H), 1.9 (d, 2H), 2.1 (d, 2H), 2.2 (brs, 1H), 2.3 (d, 2H), 2.9 (m, 2H), 3.55 (t, 2H), 3.7 (m, 3H), 4.1 (s, 1H), 4.4 (t, 2H), 4.6 (s, 1H), 7.65 (d, 1H), 7.8 (dd, 1H), 8.15 (d, 1H), 8.25 (s, 1H). HPLC (VERYPOL.M): tr=6.12 min (98%).

Example 16

1-{2-[(1,1-Dioxo-thiomorpholine-4-carbonyl)-amino]-ethyl}-1H-benzoimidazole-5-carboxylic Acid (5-hydroxy-adamantan-2-yl)-amide

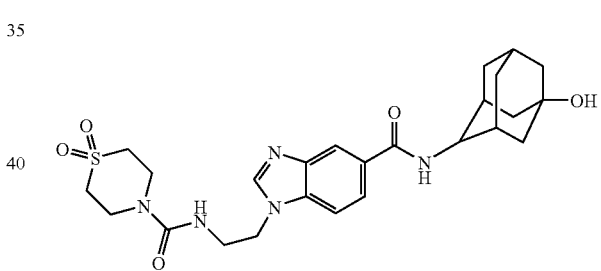

Steps A-F is similar to those used in example 15 above.
Step-I:
A) 1,1-Dioxo-thiomorpholine-4-carbonyl Chloride To a solution of thiomorpholine 1,1-dioxide (0.181 g, 0.00105 mol) in dry THF (5 mL) was added DIPEA (0.3 mL, 0.00191 mol) at 0° C. To the resulting mixture was added triphosgene (0.11 g, 0.00037 mol) and the mixture was stirred for 2 h at ambient temperature.
B) To a solution of 1-(2-aminoethyl)-1H-benzimidazole-5-carboxylic acid (5-hydroxy-adamantan-2-yl)-amide (0.25 g, 0.706 mmol) in dry THF (5 mL) was added DIPEA (0.3 mL, 1.91 mmol) at 0° C. To this reaction mixture was added compound A slowly and stirred for 2 h at ambient temperature. The solvents were evaporated and the residue purified by preparative HPLC affording cis and trans isomers of 1-{2-[(1,1-dioxo-thiomorpholine-4-carbonyl)amino]-ethyl}-1H-benzoimidazole-5-carboxylic acid (5-hydroxy-adamantan-2-yl)-amide.

Isomer I (15 mg): MS-ESI m/z 516 (M+1); $^1$H-NMR (300 MHz, CD$_3$OD) δ 1.5 (d, 2H), 1.8 (d, 4H), 1.9 (d, 2H), 2.1 (m, 3H), 2.3 (s, 2H), 2.7 (t, 4H), 3.6 (t, 2H), 4.1 (s, 1H), 4.5 (t, 2H), 7.6 (d, 1H), 7.8 (d, 1H), 8.2 (s, 1H), 8.35 (s, 1H). HPLC (VERYPOL.M): tr=6.54 min (98%).

Isomer II (17 mg): MS-ESI m/z 516 (M+1); $^1$H-NMR (300 MHz, CD$_3$OD) δ 1.6 (d, 2H), 1.8 (d, 6H), 2.1 (d, 2H), 2.2 (m, 1H), 2.4 (s, 2H), 2.7 (t, 4H), 3.6 (t, 2H), 3.7 (t, 4H), 4.0 (s, 1H), 4.5 (t, 2H), 7.6 (d, 1H), 7.8 (dd, 1H), 8.2 (s, 1H), 8.3 (s, 1H). HPLC (VERYPOL.M): tr=6.84 min (94%).

Example 17

1,1-Dioxo-thiomorpholine-4-carboxylic acid {2-[5-(3-hydroxy-8-aza-bicyclo[3.2.1]octane-8-carbonyl)-benzoimidazol-1-yl]-ethyl}-amide

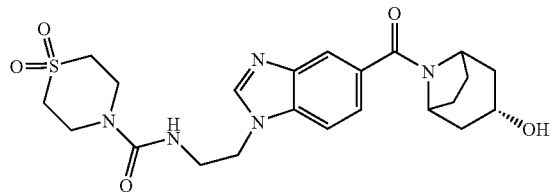

Steps A-F is similar to those used in example 16 above.

Step-I:

To a solution of [1-(2-aminoethyl)-1H-benzimidazol-5-yl]-(3-hydroxy-8-azabicyclo[3.2.1]oct-8-yl)-methanone (0.2 g, 0.636 mmol) in dry THF (5 mL) was added DIPEA (0.3 mL, 1.91 mmol) at 0° C. To this reaction mixture was added 1,1-dioxo-thiomorpholine-4-carbonyl chloride slowly and stirred for 2 h at ambient temperature. The solvents were evaporated and the residue purified by preparative HPLC to afford 1,1-dioxo-thiomorpholine-4-carboxylic acid {2-[5-(3-hydroxy-8-aza-bicyclo[3.2.1]octane-8-carbonyl)-benzoimidazol-1-yl]-ethyl}-amide (0.007 g, 2.3%). MS-ESI m/z 476 (M+1); $^1$H-NMR (300 MHz, CD$_3$OD) δ 1.5 (t, 1H), 1.8 (m, 4H), 2.1 (brs, 3H), 2.8 (s, 4H), 3.6 (t, 2H), 3.8 (s, 4H), 4.2 (m, 2H), 4.5 (t, 2H), 4.7 (s, 1H), 7.5 (d, 1H), 7.7 (d, 1H), 7.85 (s, 1H), 8.3 (s, 1H). HPLC (VERYPOL.M): tr=6.24 min (97%).

The following compounds were synthesised employing a similar method to the ones described in examples 13-17 above:

| Ex. | Structure | MW | IUPAC Name | MS-ESI m/z |
|---|---|---|---|---|
| 17-1 | 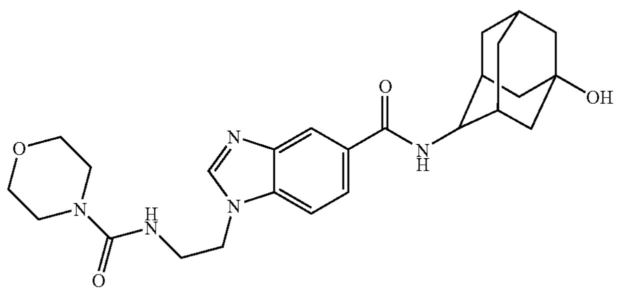 | 467.57 | Cis-1-{2-[(morpholine-4-carbonyl)-amino]-ethyl}-1H-benzo-imidazole-5-carboxylic acid (5-hydroxy-adamantan-2-yl)-amide | 458 |
| 17-2 | 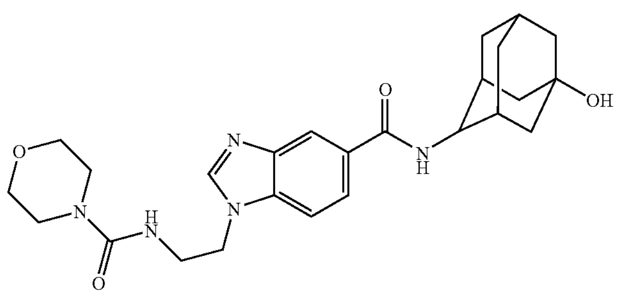 | 467.57 | Trans-1-{2-[(morpholine-4-carbonyl)-amino]-ethyl}-1H-benzo-imidazole-5-carboxylic acid (5-hydroxy-adamantan-2-yl)-amide | 458 |
| 17-3 | 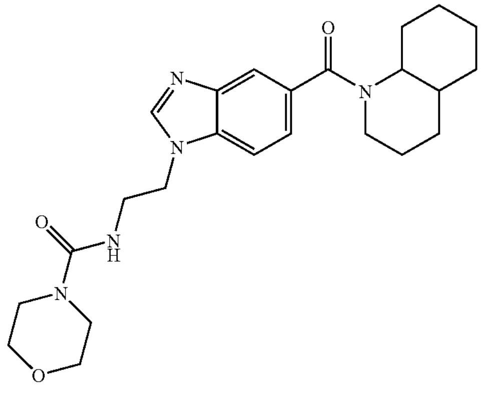 | 439.56 | Cis-morpholine-4-carboxylic acid {2-[5-(octahydro-quinoline-1-carbonyl)-benzoimidazol-1-yl]-ethyl}-amide | 440 |

| Ex. | Structure | MW | IUPAC Name | MS-ESI m/z |
|---|---|---|---|---|
| 17-4 | 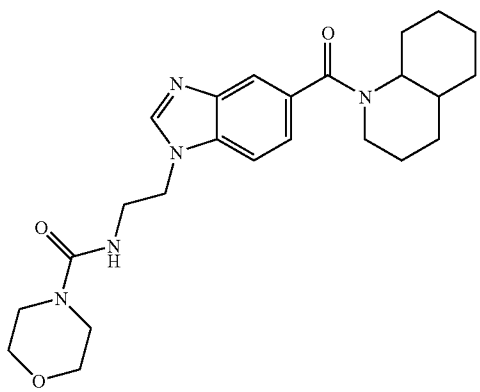 | 439.56 | Trans-morpholine-4-carboxylic acid {2-[5-(octahydro-quinoline-1-carbonyl)-benzoimidazol-1-yl]-ethyl}-amide | 440 |
| 17-5 | 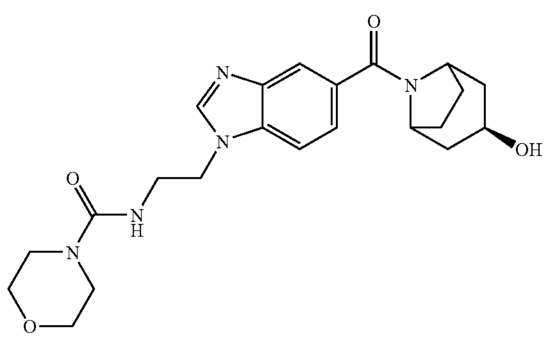 | 427.51 | Morpholine-4-carboxylic acid {2-[5-(3-hydroxy-8-aza-bicyclo-[3.2.1]octane-8-carbonyl)-benzoimidazol-1-yl]-ethyl}-amide | 428 |
| 17-6 | 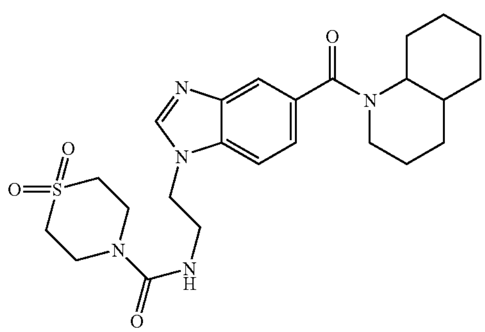 | 487.63 | 1,1-Dioxo-thiomorpholine-4-carboxylic acid {2-[5-(octahydro-quinoline-1-carbonyl)-benzoimidazol-1-yl]-ethyl}-amide | 488 |
| 17-7 | 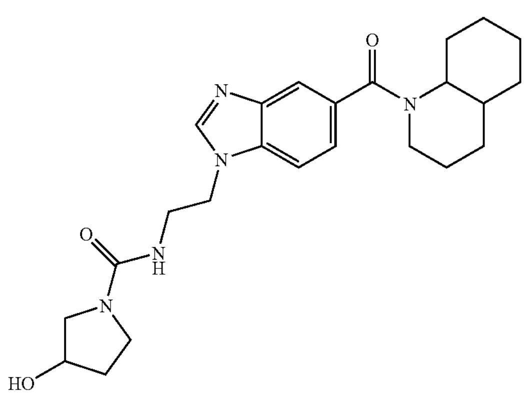 | 439.56 | 3-Hydroxy-pyrrolidine-1-carboxylic acid {2-[5-(octahydro-quinoline-1-carbonyl)-benzoimidazol-1-yl]-ethyl}-amide | 440 |

-continued

| Ex. | Structure | MW | IUPAC Name | MS-ESI m/z |
|---|---|---|---|---|
| 17-8 | 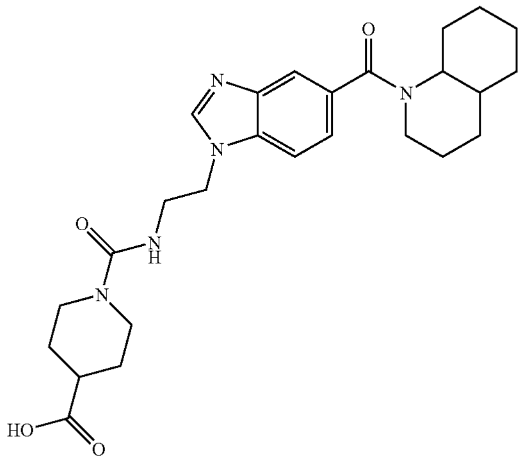 | 481.60 | 1-{2-[5-(Octahydro-quinoline-1-carbonyl)-benzoimidazol-1-yl]-ethylcarbamoyl}-piperidine-4-carboxylic acid | 482 |
| 17-9 | 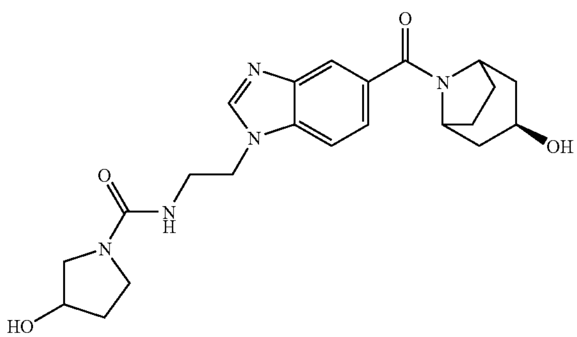 | 427.51 | 3-Hydroxy-pyrrolidine-1-carboxylic acid {2-[5-(3-hydroxy-8-aza-bicyclo[3.2.1]octane-8-carbonyl)-benzoimidazol-1-yl]-ethyl}-amide | 428 |
| 17-10 | 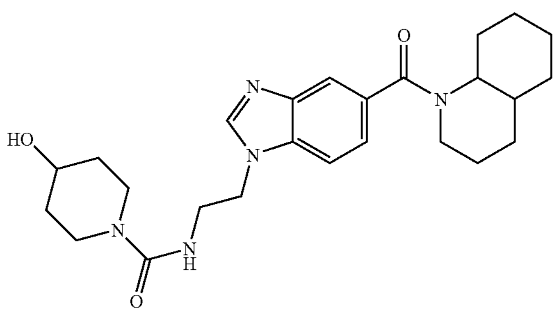 | 453.59 | Cis-4-hydroxy-piperidine-1-carboxylic acid {2-[5-(octahydro-quinoline-1-carbonyl)-benzoimidazol-1-yl]-ethyl}-amide | 454 |
| 17-11 | 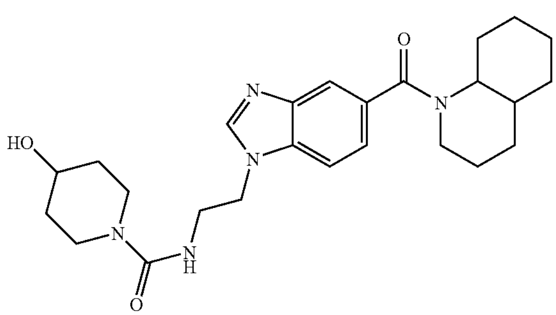 | 453.59 | Trans-4-hydroxy-piperidine-1-carboxylic acid {2-[5-(octahydro-quinoline-1-carbonyl)-benzoimidazol-1-yl]-ethyl}-amide | 454 |

-continued

| Ex. | Structure | MW | IUPAC Name | MS-ESI m/z |
|---|---|---|---|---|
| 17-12 | 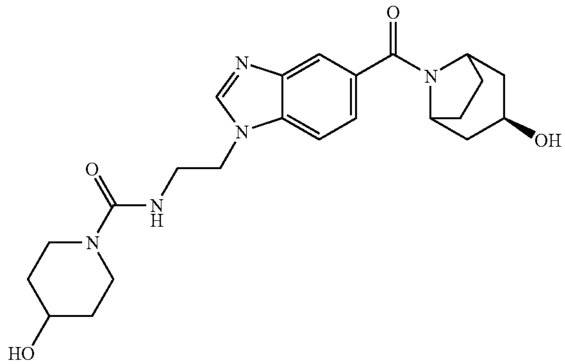 | 441.53 | Endo-4-hydroxy-piperidine-1-carboxylic acid {2-[5-(3-hydroxy-8-aza-bicyclo[3.2.1]octane-8-carbonyl)-benzoimidazol-1-yl]-ethyl}-amide | 442 |
| 17-13 | 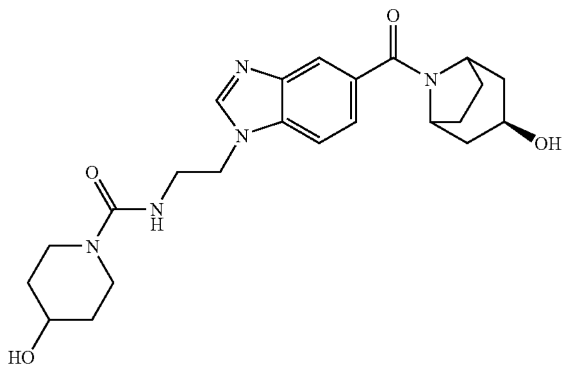 | 441.53 | Exo-4-hydroxy-piperidine-1-carboxylic acid {2-[5-(3-hydroxy-8-aza-bicyclo[3.2.1]octane-8-carbonyl)-benzoimidazol-1-yl]-ethyl}-amide | 442 |
| 17-14 | 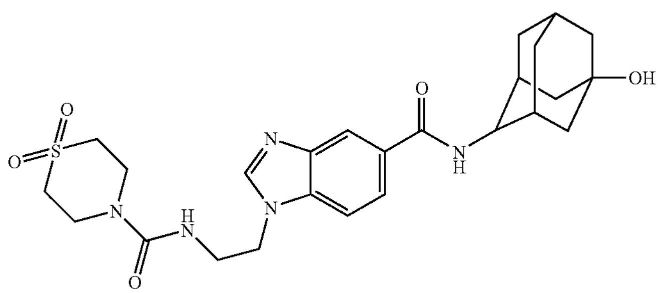 | 515.64 | 1-{2-[(1,1-Dioxo-thiomorpholine-4-carbonyl)-amino]-ethyl}-1H-benzoimidazole-5-carboxylic acid (5-hydroxy-adamantan-2-yl)-amide | 516 |
| 17-15 | 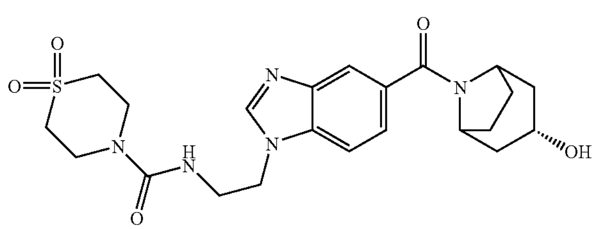 | 475.57 | 1,1-Dioxo-thiomorpholine-4-carboxylic acid {2-[5-(3-hydroxy-8-aza-bicyclo[3.2.1]-octane-8-carbonyl)-benzo-imidazol-1-yl]-ethyl}-amide | 476 |
| 17-16 | 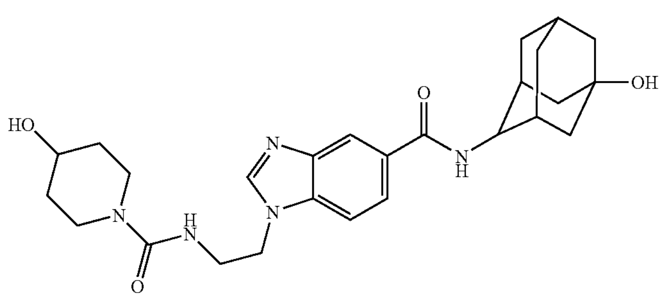 | 481.60 | 1-{2-[(4-Hydroxy-piperidine-1-carbonyl)-amino]-ethyl}-1H-benzoimidazole-5-carboxylic acid (5-hydroxy-adamantan-2-yl)-amide | 482 |

| Ex. | Structure | MW | IUPAC Name | MS-ESI m/z |
|---|---|---|---|---|
| 17-17 | 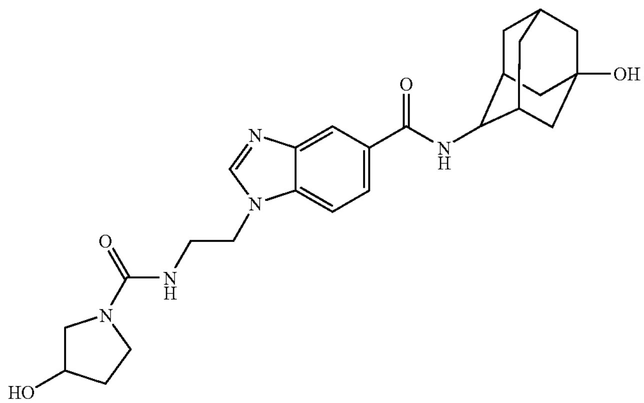 | 467.57 | 1-{2-[(3-Hydroxy-pyrrolidine-1-carbonyl)-amino]-ethyl}-1H-benzoimidazole-5-carboxylic acid (5-hydroxy-adamantan-2-yl)-amide | 468 |
| 17-18 | 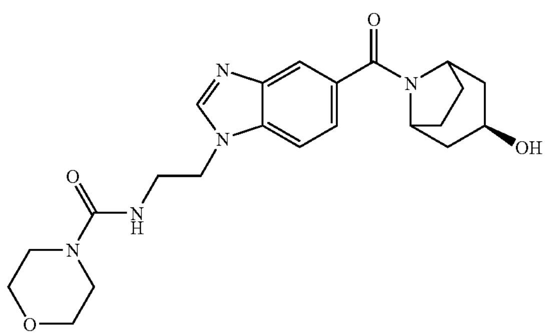 | 427.51 | Morpholine-4-carboxylic acid {2-[5-(3-hydroxy-8-aza-bicyclo-[3.2.1]octane-8-carbonyl)-benzoimidazol-1-yl]-ethyl}-amide | 428 |
| 17-19 | 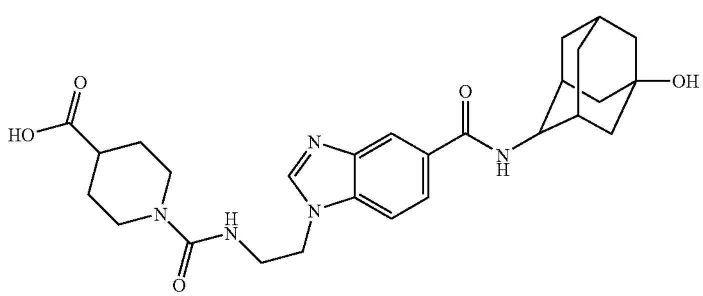 | 509.61 | Cis-1-{2-[5-(5-Hydroxy-adamantan-2-ylcarbamoyl)-benzoimidazol-1-yl]-ethylcarbamoyl}-piperidine-4-carboxylic acid | 510 |
| 17-20 | 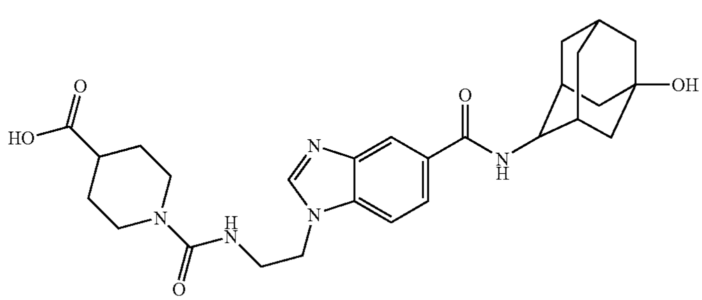 | 509.61 | Trans-1-{2-[5-(5-Hydroxy-adamantan-2-ylcarbamoyl)-benzoimidazol-1-yl]-ethylcarbamoyl}-piperidine-4-carboxylic acid | 510 |

| Ex. | Structure | MW | IUPAC Name | MS-ESI m/z |
|---|---|---|---|---|
| 17-21 | 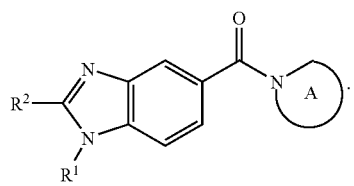 | 469.55 | 1-{2-[5-(3-Hydroxy-8-aza-bicyclo[3.2.1]octane-8-carbonyl)-benzoimidazol-1-yl]-ethyl-carbamoyl}-piperidine-4-carboxylic acid | 470 |

Pharmacological Methods
11βHSD1 Enzyme Assay
Materials 3H-cortisone and anti-rabbit Ig coated scintillation proximity assay (SPA) beads were purchased from Amersham Pharmacia Biotech, β-NADPH was from Sigma and rabbit anti-cortisol antibodies were from Fitzgerald. An extract of yeast transformed with h-11βHSD1 (Hult et al., FEBS Lett., 441, 25 (1998)) was used as the source of enzyme. The test compounds were dissolved in DMSO (10 mM). All dilutions were performed in a buffer containing 50 mM TRIS-HCl (Sigma Chemical Co), 4 mM EDTA (Sigma Chemical Co), 0.1% BSA (Sigma Chemical Co), 0.01% Tween-20 (Sigma Chemical Co) and 0.005% bacitracin (Novo Nordisk A/S), pH=7.4. Optiplate 96 wells plates were supplied by Packard. The amount of 3H-cortisol bound to the SPA beads was measured on TopCount NXT, Packard.

Methods h-11βHSD1, 120 nM 3H-cortisone, 4 mM β-NADPH, antibody (1:200), serial dilutions of test compound and SPA particles (2 mg/well) were added to the wells. The reaction was initiated by mixing the different components and was allowed to proceed under shaking for 60 min at 30° C. The reaction was stopped be the addition of 10 fold excess of a stopping buffer containing 500 μM carbenoxolone and 1 μM cortisone. Data was analysed using GraphPad Prism software.

What is claimed:

1. A compound of Formula IA or a pharmaceutically acceptable salt thereof:

IA wherein:
$R^1$ is —$(CH_2)_2$—$R^6$;
$R^2$ is selected from the group consisting of hydrogen, $C_1$-$C_6$alkyl, and —C(=O)$R^{13}$;

the ring

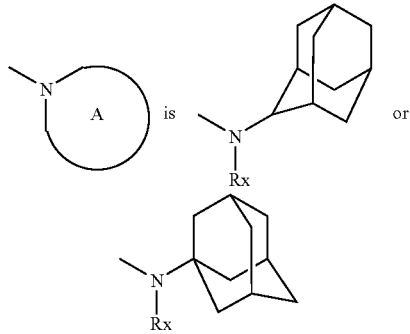

Rx is hydrogen or $C_{1-6}$alkyl, and

is substituted once with —OH;

$R^6$ is selected from the group consisting of cyano, aryl, hetaryl, -oxo$C_1$-$C_6$alkyl-S(=O)$_n R^{13}$, —C(=O)$R^{13}$, —S(=O)$_n R^{13}$, —S(=O)$_n NR^{18}R^{19}$, —N($R^{18}$)S(=O)$_n R^{13}$, —N($R^{23}$)C(=O)NR$^{18}R^{19}$, —C(=N$R^{15}$)NR$^{15}$, —N($R^{18}$)C(=O)$R^{13}$, —N($R^{18}$)C(=O)—$C_3$-$C_6$cycloalkyl, and —N($R^{18}$)C(=O)—(3-6 membered hetcycloalkyl), wherein the cycloalkyl, hetcycloalkyl, aryl, and hetaryl groups are substituted with 0-3 $R^{16}$;

$R^{13}$ is selected from the group consisting of —OH, $C_1$-$C_4$alkyl, $C_1$-$C_4$alkyloxy, $C_1$-$C_4$alkyloxy$C_1$-$C_4$alkylene, aryl, hetaryl, aryloxy, hetaryloxy, and NR$^{18}R^{19}$;

$R^{15}$ and $R^{16}$ are independently selected from the group consisting of H, $C_1$-$C_4$alkyl, 3-6-membered cycloalkyl, halo, OH, cyano, —C(=O)$R^{13}$, —S(=O)$_n R^{13}$, —S(=O)$_n NR^{18}R^{19}$, —N($R^{18}$)S(=O)$_n R^{13}$, aryl, and hetaryl, wherein the alkyl and cycloalkyl groups are substituted with 0-1 $R^{20}$;

R[18] and R[19] are independently selected from the group consisting of H, $C_1$-$C_4$alkyl, $C_1$-$C_4$alkyloxy, aryl, hetaryl, aryl$C_1$-$C_4$alkylene, and hetaryl$C_1$-$C_4$alkylene, wherein the alkyl, alkylene, aryl, and hetaryl groups are independently substituted with 0-1 R[20];

alternatively, R[18] and R[19], together with the nitrogen atom to which they are attached, form a saturated or partially saturated monocyclic, bicyclic, or tricyclic ring consisting of the shown nitrogen, 4-5 carbon atoms, and 0-1 additional heteroatoms selected from the group consisting of nitrogen, oxygen, and sulfur, wherein this ring is substituted 0-1 times with substituents selected from the group consisting of $C_1$-$C_4$alkyl, aryl, hetaryl, aryl$C_1$-$C_4$alkylene, hetaryl$C_1$-$C_4$alkylene, hydroxy, and $C_1$-$C_4$alkyloxy;

R[20] is selected from the group consisting of H, OH, oxo, halo, cyano, nitro, $C_1$-$C_4$alkyl, $C_1$-$C_4$alkyloxy, NR[21]R[22], trihalomethyl, and trihalomethyloxy;

R[21] and R[22] are independently selected from the group consisting of H, $C_1$-$C_4$alkyl, and aryl$C_1$-$C_4$alkyl;

R[23] is selected from the group consisting of H and $C_1$-$C_6$alkyl; and n is 2.

2. The compound of claim 1, wherein $R^2$ is H.

3. The compound of claim 2, wherein the ring

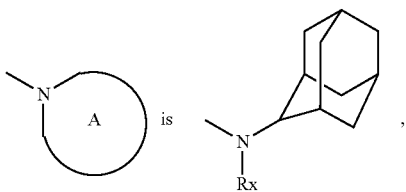

and Rx is hydrogen.

4. A compound selected from the group consisting of:
trans-1-(2-methanesulfonyl-methoxy-ethyl)-1H-benzoimidazole-5-carboxylic acid (5-hydroxy-adamantan-2-yl)-amide;
1-(2-methanesulfonyl-ethyl)-1H-benzoimidazole-5-carboxylic acid (5-hydroxy-adamantan-2-yl)-amide;
trans-1-[2-(1H-tetrazol-5-yl)-ethyl]-1H-benzoimidazole-5-carboxylic acid (5-hydroxy-adamantan-2-yl)-amide;
1-{2-[(4-hydroxy-piperidine-1-carbonyl)-amino]-ethyl}-1H-benzoimidazole-5-carboxylic acid (5-hydroxy-adamantan-2-yl)-amide;
1-{2-[(1,1-dioxo-thiomorpholine-4-carbonyl)-amino]-ethyl}-1H-benzoimidazole-5-carboxylic acid (5-hydroxy-adamantan-2-yl)-amide;
cis-1-{2-[(morpholine-4-carbonyl)-amino]-ethyl}-1H-benzo-imidazole-5-carboxylic acid (5-hydroxy-adamantan-2-yl)-amide;
trans-1-{2-[(morpholine-4-carbonyl)-amino]-ethyl}-1H-benzo-imidazole-5-carboxylic acid (5-hydroxy-adamantan-2-yl)-amide;
1-{2-[(3-hydroxy-pyrrolidine-1-carbonyl)-amino]-ethyl}-1H-benzoimidazole-5-carboxylic acid (5-hydroxy-adamantan-2-yl)-amide;
cis-1-{2-[5-(5-hydroxy-adamantan-2-ylcarbamoyl)-benzoimidazol-1-yl]-ethylcarbamoyl}-piperidine-4-carboxylic acid; and
trans-1-{2-[5-(5-hydroxy-adamantan-2-ylcarbamoyl)-benzoimidazol-1-yl]-ethylcarbamoyl}-piperidine-4-carboxylic acid;
or a pharmaceutically acceptable salt thereof.

5. A pharmaceutical composition comprising a compound of claim 1 and a pharmaceutically acceptable carrier or diluent.

6. A pharmaceutical composition comprising a compound of claim 2 and a pharmaceutically acceptable carrier or diluent.

7. A pharmaceutical composition comprising a compound of claim 3 and a pharmaceutically acceptable carrier or diluent.

8. A pharmaceutical composition comprising a compound of claim 4 and a pharmaceutically acceptable carrier or diluent.

* * * * *